(12) United States Patent
Fedor et al.

(10) Patent No.: US 11,464,960 B2
(45) Date of Patent: Oct. 11, 2022

(54) LOW-PROFILE SINGLE AND DUAL VASCULAR ACCESS DEVICE

(71) Applicant: C. R. Bard, Inc., Murray Hill, NJ (US)

(72) Inventors: Brenda L. Fedor, Holladay, UT (US); Jason R. Stats, Layton, UT (US); Michael A. Randall, Gilbert, AZ (US); Chad C. Van Liere, Phoenix, AZ (US); Jeremy B. Cox, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 754 days.

(21) Appl. No.: 16/382,177

(22) Filed: Apr. 11, 2019

(65) Prior Publication Data

US 2019/0232035 A1    Aug. 1, 2019

Related U.S. Application Data

(63) Continuation-in-part of application No. 15/809,879, filed on Nov. 10, 2017, which is a
(Continued)

(51) Int. Cl.
*A61M 39/02* (2006.01)
*A61M 25/00* (2006.01)
(Continued)

(52) U.S. Cl.
CPC ...... *A61M 39/0247* (2013.01); *A61M 1/3653* (2013.01); *A61M 1/3659* (2014.02);
(Continued)

(58) Field of Classification Search
CPC ............ A61M 39/0247; A61M 1/3653; A61M 1/3659; A61M 25/003; A61M 25/0097;
(Continued)

(56) References Cited

U.S. PATENT DOCUMENTS 3,951,147 A   4/1976  Tucker et al.
4,184,489 A   1/1980  Burd
(Continued)

FOREIGN PATENT DOCUMENTS

CA       1261698 A    9/1989
CA       2318089 A1   7/1999
(Continued)

OTHER PUBLICATIONS

U.S. Appl. No. 14/162,113, filed Jan. 23, 2014 Notice of Allowance dated Aug. 14, 2019.
(Continued)

*Primary Examiner* — Amber R Stiles
(74) *Attorney, Agent, or Firm* — Rutan & Tucker LLP

(57) ABSTRACT

A low-profile access port for subcutaneous implantation within a patient. The access port can include a set of receiving cups which can be placed in fluid communication with a catheter. The set of receiving cups can provide a greater skin surface with which to access the port to avoid repeated penetrations at a single locus, such as during consecutive dialysis treatments. The access port can alternatively include needle penetrable arms or elongate chambers that also have a slim, low profile. The access port can include a needle guide to direct subsequent needle access to different insertion points to permit healing at the previous insertion points. The access port can be formed of a modular construction with a first conduit, a second conduit, and an outer shell. The outer shell can include a proximal portion and a distal portion. The access port can include a stem assembly and a locking member.

7 Claims, 52 Drawing Sheets

Related U.S. Application Data continuation-in-part of application No. 14/162,113, filed on Jan. 23, 2014, now Pat. No. 10,463,845.

(60) Provisional application No. 62/732,928, filed on Sep. 18, 2018, provisional application No. 62/657,662, filed on Apr. 13, 2018, provisional application No. 62/552,681, filed on Aug. 31, 2017, provisional application No. 62/421,131, filed on Nov. 11, 2016, provisional application No. 61/755,913, filed on Jan. 23, 2013.

(51) Int. Cl.
*A61M 25/01* (2006.01)
*A61M 1/36* (2006.01)
*A61M 39/00* (2006.01)

(52) U.S. Cl.
CPC ...... *A61M 25/003* (2013.01); *A61M 25/0097* (2013.01); *A61M 25/0108* (2013.01); *A61M 2025/0031* (2013.01); *A61M 2039/0036* (2013.01); *A61M 2039/0081* (2013.01); *A61M 2039/027* (2013.01); *A61M 2039/0211* (2013.01); *A61M 2039/0232* (2013.01); *A61M 2039/0235* (2013.01); *A61M 2039/0238* (2013.01); *A61M 2039/0258* (2013.01); *A61M 2039/0261* (2013.01); *A61M 2039/0264* (2013.01); *A61M 2039/0273* (2013.01); *A61M 2039/0276* (2013.01); *A61M 2205/3331* (2013.01); *A61M 2205/582* (2013.01); *Y10T 29/49826* (2015.01)

(58) Field of Classification Search
CPC ...... A61M 25/0108; A61M 2025/0031; A61M 2039/0036; A61M 2039/0081; A61M 2039/0211; A61M 2039/0232; A61M 2039/0235; A61M 2039/0238; A61M 2039/0258; A61M 2039/0261; A61M 2039/0264; A61M 2039/027; A61M 2039/0273; A61M 2039/0276; A61M 2205/3331; A61M 2205/582; A61M 1/3661; Y10T 29/49826
See application file for complete search history.

(56) References Cited

U.S. PATENT DOCUMENTS

| | | |
|---|---|---|
| 4,222,374 A | 9/1980 | Sampson et al. |
| 4,400,169 A | 8/1983 | Stephen |
| 4,447,237 A | 5/1984 | Frisch et al. |
| 4,496,349 A | 1/1985 | Cosentino |
| 4,543,088 A | 9/1985 | Bootman et al. |
| 4,559,039 A | 12/1985 | Ash et al. |
| 4,569,675 A | 2/1986 | Prosl et al. |
| 4,673,394 A | 6/1987 | Fenton, Jr. et al. |
| 4,692,146 A | 9/1987 | Hilger |
| 4,695,273 A | 9/1987 | Brown |
| 4,704,103 A | 11/1987 | Stober et al. |
| 4,710,174 A | 12/1987 | Moden et al. |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,778,452 A | 10/1988 | Moden et al. |
| 4,790,826 A | 12/1988 | Elftman |
| 4,802,885 A | 2/1989 | Weeks et al. |
| 4,804,054 A | 2/1989 | Howson et al. |
| 4,820,273 A | 4/1989 | Reinicke |
| 4,861,341 A | 8/1989 | Woodburn |
| 4,886,501 A | 12/1989 | Johnston et al. |
| 4,892,518 A | 1/1990 | Cupp et al. |
| 4,897,081 A | 1/1990 | Poirier et al. |
| 4,904,241 A | 2/1990 | Bark |
| 4,915,690 A | 4/1990 | Cone et al. |
| 4,929,236 A | 5/1990 | Sampson |
| 4,963,133 A | 10/1990 | Whipple |
| 4,978,338 A | 12/1990 | Melsky et al. |
| 5,013,298 A | 5/1991 | Moden et al. |
| 5,041,098 A | 8/1991 | Loiterman et al. |
| 5,045,060 A | 9/1991 | Melsky et al. |
| 5,045,064 A | 9/1991 | Idriss |
| 5,053,013 A | 10/1991 | Ensminger et al. |
| 5,057,084 A | 10/1991 | Ensminger et al. |
| 5,084,015 A | 1/1992 | Moriuchi |
| 5,090,954 A | 2/1992 | Geary |
| 5,108,377 A | 4/1992 | Cone et al. |
| 5,137,529 A | 8/1992 | Watson et al. |
| 5,147,321 A | 9/1992 | Slonina et al. |
| 5,147,483 A | 9/1992 | Melsky et al. |
| 5,158,547 A | 10/1992 | Doan et al. |
| 5,167,633 A | 12/1992 | Mann et al. |
| 5,167,638 A | 12/1992 | Felix et al. |
| 5,171,228 A | 12/1992 | McDonald |
| 5,178,612 A | 1/1993 | Fenton, Jr. |
| 5,180,365 A | 1/1993 | Ensminger et al. |
| 5,185,003 A | 2/1993 | Brethauer |
| 5,201,715 A | 4/1993 | Masters |
| 5,203,771 A | 4/1993 | Melker et al. |
| 5,213,574 A | 5/1993 | Tucker |
| D337,637 S | 7/1993 | Tucker |
| 5,226,879 A | 7/1993 | Ensminger et al. |
| 5,263,930 A | 11/1993 | Ensminger |
| 5,266,071 A | 11/1993 | Elftman |
| 5,281,199 A | 1/1994 | Ensminger et al. |
| 5,281,205 A | 1/1994 | McPherson |
| 5,318,545 A | 6/1994 | Tucker |
| 5,336,194 A | 8/1994 | Polaschegg et al. |
| 5,350,360 A | 9/1994 | Ensminger et al. |
| 5,360,407 A | 11/1994 | Leonard et al. |
| 5,387,192 A | 2/1995 | Glantz et al. |
| 5,395,324 A | 3/1995 | Hinrichs et al. |
| 5,399,168 A | 3/1995 | Wadsworth, Jr. et al. |
| 5,405,325 A | 4/1995 | Labs |
| 5,409,463 A | 4/1995 | Thomas et al. |
| 5,417,656 A | 5/1995 | Ensminger et al. |
| 5,421,814 A | 6/1995 | Geary |
| 5,423,334 A | 6/1995 | Jordan |
| 5,476,451 A | 12/1995 | Ensminger et al. |
| 5,503,630 A | 4/1996 | Ensminger et al. |
| 5,514,103 A | 5/1996 | Srisathapat et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,531,684 A | 7/1996 | Ensminger et al. |
| 5,542,923 A | 8/1996 | Ensminger et al. |
| 5,554,117 A | 9/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,578,070 A | 11/1996 | Utterberg |
| 5,607,393 A | 3/1997 | Ensminger et al. |
| 5,613,945 A | 3/1997 | Cai et al. |
| 5,620,419 A | 4/1997 | Lui et al. |
| 5,632,729 A | 5/1997 | Cai et al. |
| 5,647,855 A | 7/1997 | Trooskin |
| 5,695,490 A | 12/1997 | Flaherty et al. |
| 5,702,363 A | 12/1997 | Flaherty |
| 5,704,915 A | 1/1998 | Melsky et al. |
| 5,713,858 A | 2/1998 | Heruth et al. |
| 5,718,682 A | 2/1998 | Tucker |
| 5,725,507 A | 3/1998 | Petrick |
| 5,741,228 A | 4/1998 | Lambrecht et al. |
| 5,743,873 A | 4/1998 | Cai et al. |
| 5,758,667 A | 6/1998 | Slettenmark |
| 5,769,823 A | 6/1998 | Otto |
| 5,792,104 A | 8/1998 | Speckman et al. |
| 5,810,789 A | 9/1998 | Powers et al. |
| 5,833,654 A | 11/1998 | Powers et al. |

(56) References Cited

U.S. PATENT DOCUMENTS

| | | |
|---|---|---|
| 5,848,989 A | 12/1998 | Villani |
| 5,906,596 A | 5/1999 | Tallarida |
| 5,908,414 A | 6/1999 | Otto et al. |
| 5,913,998 A | 6/1999 | Butler et al. |
| 5,925,017 A | 7/1999 | Kriesel et al. |
| 5,931,829 A | 8/1999 | Burbank et al. |
| 5,944,688 A | 8/1999 | Lois |
| 5,947,953 A | 9/1999 | Ash et al. |
| 5,951,512 A | 9/1999 | Dalton |
| 5,954,687 A | 9/1999 | Baudino |
| 5,954,691 A | 9/1999 | Prosl |
| 5,968,011 A | 10/1999 | Larsen et al. |
| 5,989,206 A | 11/1999 | Prosl et al. |
| 5,989,216 A | 11/1999 | Johnson et al. |
| 5,989,239 A | 11/1999 | Finch et al. |
| 6,007,516 A | 12/1999 | Burbank et al. |
| 6,013,051 A | 1/2000 | Nelson |
| 6,013,058 A | 1/2000 | Prosl et al. |
| 6,022,335 A | 2/2000 | Ramadan |
| 6,039,712 A | 3/2000 | Fogarty et al. |
| 6,042,569 A | 3/2000 | Finch, Jr. et al. |
| 6,053,901 A | 4/2000 | Finch, Jr. et al. |
| 6,056,717 A | 5/2000 | Finch et al. |
| 6,086,555 A | 7/2000 | Eliasen et al. |
| 6,090,067 A | 7/2000 | Carter |
| 6,090,068 A | 7/2000 | Chanut |
| 6,102,884 A | 8/2000 | Squitieri |
| 6,120,492 A | 9/2000 | Finch et al. |
| 6,190,349 B1 | 2/2001 | Ash et al. |
| 6,190,352 B1 | 2/2001 | Haarala et al. |
| 6,206,851 B1 | 3/2001 | Prosl |
| 6,213,973 B1 | 4/2001 | Eliasen et al. |
| D445,175 S | 7/2001 | Bertheas |
| 6,287,293 B1 | 9/2001 | Jones et al. |
| 6,332,874 B1 | 12/2001 | Eliasen et al. |
| 6,350,251 B1 | 2/2002 | Prosl et al. |
| 6,352,521 B1 | 3/2002 | Prosl |
| 6,398,764 B1 | 6/2002 | Finch, Jr. et al. |
| 6,436,084 B1 | 8/2002 | Finch et al. |
| 6,438,397 B1 | 8/2002 | Bosquet et al. |
| 6,459,917 B1 | 10/2002 | Gowda et al. |
| 6,478,783 B1 | 11/2002 | Moorehead |
| 6,482,197 B2 | 11/2002 | Finch et al. |
| 6,494,867 B1 | 12/2002 | Elver et al. |
| 6,506,182 B2 | 1/2003 | Estabrook et al. |
| 6,527,754 B1 | 3/2003 | Tallarida et al. |
| 6,540,717 B2 * | 4/2003 | Sherry .............. A61M 39/0208 604/93.01 |
| 6,582,409 B1 | 6/2003 | Squitieri |
| 6,607,504 B2 | 8/2003 | Haarala et al. |
| 6,620,118 B1 | 9/2003 | Prosl et al. |
| 6,695,832 B2 | 2/2004 | Schon et al. |
| 6,699,218 B2 | 3/2004 | Flaherty et al. |
| 6,719,749 B1 | 4/2004 | Schweikert et al. |
| 6,726,711 B1 | 4/2004 | Langenbach et al. |
| 6,758,841 B2 | 7/2004 | Haarala et al. |
| 6,783,522 B2 | 8/2004 | Fischell |
| 6,852,106 B2 | 2/2005 | Watson et al. |
| 6,881,211 B2 | 4/2005 | Schweikert et al. |
| 6,929,631 B1 | 8/2005 | Brugger et al. |
| 6,960,185 B2 | 11/2005 | Adaniya et al. |
| 6,962,580 B2 | 11/2005 | Adams et al. |
| 6,997,914 B2 | 2/2006 | Smith et al. |
| 7,018,374 B2 | 3/2006 | Schon et al. |
| 7,056,316 B1 | 6/2006 | Burbank et al. |
| 7,070,591 B2 | 7/2006 | Adams et al. |
| 7,083,648 B2 | 8/2006 | Yu et al. |
| 7,108,686 B2 | 9/2006 | Burke et al. |
| 7,131,962 B1 | 11/2006 | Estabrook et al. |
| 7,223,257 B2 | 5/2007 | Shubayev et al. |
| 7,261,705 B2 | 8/2007 | Edoga et al. |
| 7,311,702 B2 | 12/2007 | Tallarida et al. |
| 7,322,953 B2 | 1/2008 | Redinger |
| D562,443 S | 2/2008 | Zinn et al. |
| 7,347,843 B2 | 3/2008 | Adams et al. |
| 7,351,233 B2 | 4/2008 | Parks |
| 7,396,359 B1 | 7/2008 | Derowe et al. |
| D574,950 S | 8/2008 | Zawacki et al. |
| D578,203 S | 10/2008 | Bizup |
| 7,445,614 B2 | 11/2008 | Bunodiere et al. |
| D582,032 S | 12/2008 | Bizup et al. |
| 7,497,850 B2 | 3/2009 | Halili |
| D612,479 S | 3/2010 | Zawacki et al. |
| 7,699,821 B2 | 4/2010 | Nowak |
| 7,704,225 B2 | 4/2010 | Kantrowitz |
| 7,708,722 B2 | 5/2010 | Glenn |
| 7,713,251 B2 | 5/2010 | Tallarida et al. |
| 7,731,680 B2 | 6/2010 | Patton |
| 7,762,999 B2 | 7/2010 | Byrum |
| 7,824,365 B2 | 11/2010 | Haarala et al. |
| 7,846,139 B2 | 12/2010 | Zinn et al. |
| 7,850,666 B2 | 12/2010 | Schon et al. |
| 7,909,804 B2 | 3/2011 | Stats |
| 7,959,615 B2 | 6/2011 | Stats et al. |
| 7,972,315 B2 | 7/2011 | Birk et al. |
| 7,981,094 B2 | 7/2011 | Chelak |
| D650,475 S | 12/2011 | Smith et al. |
| 8,075,536 B2 | 12/2011 | Gray et al. |
| 8,079,990 B2 | 12/2011 | Powley et al. |
| 8,147,455 B2 | 4/2012 | Butts et al. |
| 8,152,792 B1 | 4/2012 | Kornel |
| 8,257,325 B2 | 9/2012 | Schweikert et al. |
| 8,277,425 B2 | 10/2012 | Girard et al. |
| 8,328,768 B2 | 12/2012 | Quigley et al. |
| 8,337,464 B2 | 12/2012 | Young et al. |
| 8,337,465 B2 | 12/2012 | Young et al. |
| 8,337,470 B2 | 12/2012 | Prasad et al. |
| 8,343,108 B2 | 1/2013 | Rosenberg et al. |
| 8,364,230 B2 | 1/2013 | Simpson et al. |
| 8,377,034 B2 | 2/2013 | Tallarida et al. |
| 8,425,416 B2 | 4/2013 | Brister et al. |
| 8,425,476 B2 | 4/2013 | Glenn |
| 8,480,560 B2 | 7/2013 | Vendely |
| 8,550,981 B2 | 10/2013 | Woodruff et al. |
| 8,574,204 B2 | 11/2013 | Bourne et al. |
| RE44,639 E | 12/2013 | Squitieri |
| 8,622,980 B2 | 1/2014 | Zinn |
| 8,690,815 B2 | 4/2014 | Porter et al. |
| 8,690,816 B2 | 4/2014 | Dakin et al. |
| 8,738,151 B2 | 5/2014 | Nelson |
| 8,979,806 B2 | 3/2015 | Saab |
| 9,033,931 B2 | 5/2015 | Young et al. |
| 9,061,129 B2 | 6/2015 | Lauer |
| 9,072,880 B2 | 7/2015 | Phillips et al. |
| 9,072,881 B2 | 7/2015 | Dalton et al. |
| 9,078,982 B2 | 7/2015 | Lane et al. |
| 9,089,395 B2 | 7/2015 | Honaryar |
| 9,095,665 B2 | 8/2015 | Pages et al. |
| 9,138,563 B2 | 9/2015 | Glenn |
| 9,168,365 B2 | 10/2015 | Bourne et al. |
| 9,174,037 B2 | 11/2015 | Schutz et al. |
| 9,179,901 B2 | 11/2015 | Young et al. |
| 9,180,248 B2 | 11/2015 | Moberg et al. |
| 9,474,888 B2 | 10/2016 | Wiley et al. |
| 9,579,496 B2 | 2/2017 | Evans et al. |
| 9,987,467 B2 | 6/2018 | Jochum |
| 10,207,095 B2 | 2/2019 | Barron et al. |
| 10,272,236 B2 | 4/2019 | Davey |
| 10,463,845 B2 | 11/2019 | Stats et al. |
| D870,264 S | 12/2019 | Fedor et al. |
| D885,557 S | 5/2020 | Fedor et al. |
| 2001/0041870 A1 | 11/2001 | Gillis et al. |
| 2001/0056266 A1 | 12/2001 | Tallarida et al. |
| 2003/0023208 A1 | 1/2003 | Osypka et al. |
| 2003/0181878 A1 | 9/2003 | Tallarida et al. |
| 2004/0054352 A1 | 3/2004 | Adams et al. |
| 2004/0073196 A1 | 4/2004 | Adams et al. |
| 2004/0199129 A1 | 10/2004 | DiMatteo |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2005/0075614 A1 | 4/2005 | Bunodiere et al. |
| 2005/0113806 A1 | 5/2005 | De Carvalho et al. |
| 2005/0131352 A1 | 6/2005 | Conlon et al. |

(56) References Cited

U.S. PATENT DOCUMENTS

| | | |
|---|---|---|
| 2005/0148956 A1 | 7/2005 | Conlon et al. |
| 2005/0148957 A1 | 7/2005 | Girard et al. |
| 2005/0171502 A1 | 8/2005 | Daly et al. |
| 2005/0203484 A1 | 9/2005 | Nowak |
| 2005/0209573 A1 | 9/2005 | Brugger et al. |
| 2005/0256451 A1 | 11/2005 | Adams et al. |
| 2005/0277899 A1 | 12/2005 | Conlon et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0173424 A1 | 8/2006 | Conlon |
| 2006/0178617 A1 | 8/2006 | Adams et al. |
| 2006/0178647 A1 | 8/2006 | Stats |
| 2006/0184142 A1 | 8/2006 | Schon et al. |
| 2006/0217659 A1 | 9/2006 | Patton |
| 2006/0217673 A1 | 9/2006 | Schulze et al. |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2006/0271012 A1 | 11/2006 | Canaud et al. |
| 2007/0049806 A1 | 3/2007 | Adams et al. |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0083156 A1 | 4/2007 | Muto et al. |
| 2007/0161958 A1 | 7/2007 | Glenn |
| 2007/0179456 A1 | 8/2007 | Glenn |
| 2007/0208313 A1 | 9/2007 | Conlon et al. |
| 2007/0219510 A1 | 9/2007 | Zinn et al. |
| 2007/0232997 A1 | 10/2007 | Glenn |
| 2007/0233017 A1 | 10/2007 | Zinn et al. |
| 2007/0233018 A1 | 10/2007 | Bizup et al. |
| 2007/0255234 A1 | 11/2007 | Haase et al. |
| 2007/0270770 A1 | 11/2007 | Bizup |
| 2007/0276344 A1 | 11/2007 | Bizup et al. |
| 2007/0282308 A1 | 12/2007 | Bell |
| 2008/0048855 A1 | 2/2008 | Berger |
| 2008/0086075 A1 | 4/2008 | Isik et al. |
| 2008/0108942 A1 | 5/2008 | Brister et al. |
| 2008/0114308 A1 | 5/2008 | di Palma et al. |
| 2008/0132946 A1 | 6/2008 | Mueller |
| 2008/0208236 A1 | 8/2008 | Hobbs et al. |
| 2008/0281279 A1 | 11/2008 | Hoendervoogt et al. |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0099526 A1 | 4/2009 | Powley et al. |
| 2009/0105688 A1 | 4/2009 | McIntyre et al. |
| 2009/0118683 A1 | 5/2009 | Hanson et al. |
| 2009/0156928 A1 | 6/2009 | Evans et al. |
| 2009/0192467 A1 | 7/2009 | Hansen et al. |
| 2009/0204074 A1 | 8/2009 | Powers et al. |
| 2009/0221976 A1 | 9/2009 | Linden |
| 2009/0259164 A1 | 10/2009 | Pages et al. |
| 2010/0042073 A1 | 2/2010 | Oster et al. |
| 2010/0121283 A1 | 5/2010 | Hamatake et al. |
| 2010/0298684 A1 | 11/2010 | Leach et al. |
| 2011/0118677 A1 | 5/2011 | Wiley et al. |
| 2011/0257577 A1 | 10/2011 | Lane et al. |
| 2011/0264058 A1 | 10/2011 | Linden et al. |
| 2011/0319728 A1 | 12/2011 | Petisce et al. |
| 2012/0172711 A1 | 7/2012 | Kerr et al. |
| 2012/0283518 A1 | 11/2012 | Hart |
| 2013/0030348 A1 | 1/2013 | Lauer |
| 2013/0150767 A1 | 6/2013 | Tsyrulnykov et al. |
| 2013/0150811 A1 | 6/2013 | Horgan |
| 2014/0207086 A1 | 7/2014 | Stats et al. |
| 2015/0190622 A1 | 7/2015 | Saab |
| 2015/0196704 A1 | 7/2015 | Adler |
| 2015/0250933 A1 | 9/2015 | Kerkhoffs et al. |
| 2015/0258322 A1 | 9/2015 | Young et al. |
| 2015/0265280 A1 | 9/2015 | Blatter et al. |
| 2015/0273201 A1 | 10/2015 | Tallarida et al. |
| 2015/0290446 A1 | 10/2015 | Wiley et al. |
| 2015/0306300 A1 | 10/2015 | Phillips et al. |
| 2015/0327844 A1 | 11/2015 | Hong et al. |
| 2016/0001055 A1 | 1/2016 | Bourne et al. |
| 2018/0078751 A1 | 3/2018 | Fedor et al. |

FOREIGN PATENT DOCUMENTS

| | | |
|---|---|---|
| CA | 2551680 A1 | 7/2005 |
| CN | 102271737 A | 12/2011 |
| EP | 0229729 A2 | 7/1987 |
| EP | 0366814 A1 | 5/1990 |
| EP | 0 809 523 A1 | 12/1997 |
| EP | 1047473 A1 | 11/2000 |
| EP | 1056506 A1 | 12/2000 |
| EP | 2948121 B1 | 11/2017 |
| JP | H05-506591 A | 9/1993 |
| JP | H07-148206 A | 6/1995 |
| JP | H08-501008 A | 2/1996 |
| JP | 2008-531226 A | 8/2008 |
| WO | 1991/012838 A1 | 9/1991 |
| WO | 1993005730 A1 | 4/1993 |
| WO | 1994005246 A1 | 3/1994 |
| WO | 96/25196 A1 | 8/1996 |
| WO | 1996029112 A1 | 9/1996 |
| WO | 1997001370 A1 | 1/1997 |
| WO | 1997006845 A1 | 2/1997 |
| WO | 1998017337 A1 | 4/1998 |
| WO | 1999034859 A1 | 7/1999 |
| WO | 1999042166 A1 | 8/1999 |
| WO | 2000033901 A1 | 6/2000 |
| WO | 2000044424 A1 | 8/2000 |
| WO | 2000053245 A1 | 9/2000 |
| WO | 2001026713 A1 | 4/2001 |
| WO | 01/80926 A2 | 11/2001 |
| WO | 2002038460 A1 | 5/2002 |
| WO | 2002066595 A1 | 8/2002 |
| WO | 2003066126 A2 | 8/2003 |
| WO | 2004004800 A2 | 1/2004 |
| WO | 2004071555 A2 | 8/2004 |
| WO | 2004091434 A2 | 10/2004 |
| WO | 2004093970 A1 | 11/2004 |
| WO | 2005068009 A1 | 7/2005 |
| WO | 2006064753 A1 | 6/2006 |
| WO | 2006078915 A2 | 7/2006 |
| WO | 2006096686 A1 | 9/2006 |
| WO | 2006116438 A2 | 11/2006 |
| WO | 2006130133 A1 | 12/2006 |
| WO | 2006134100 A1 | 12/2006 |
| WO | 2007079024 A2 | 7/2007 |
| WO | 2007082003 A2 | 7/2007 |
| WO | 2007087460 A2 | 8/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008048361 A1 | 4/2008 |
| WO | 2008063226 A2 | 5/2008 |
| WO | 2008140901 A1 | 11/2008 |
| WO | 2008157763 A1 | 12/2008 |
| WO | 2009002839 A1 | 12/2008 |
| WO | 2009012385 A1 | 1/2009 |
| WO | 2009035582 A1 | 3/2009 |
| WO | 2009046439 A2 | 4/2009 |
| WO | 2009108669 A1 | 9/2009 |
| WO | 2012064881 A2 | 5/2012 |
| WO | 2014017986 A1 | 1/2014 |
| WO | 2014116810 A1 | 7/2014 |
| WO | 2015179862 A1 | 11/2015 |
| WO | 2019/200304 A1 | 10/2019 |

OTHER PUBLICATIONS

U.S. Appl. No. 29/616,511, filed Sep. 6, 2017 Notice of Allowance dated Aug. 8, 2019.

(56) References Cited

OTHER PUBLICATIONS

Canaud, B. et. al. "Dialock: a new vascular access device for extracorporeal renal replacement therapy. Preliminary clinical results"—Mar. 1999.
CN 201480005902.2 filed Jul. 23, 2015 Office Action dated Jan. 20, 2016.
CN 201480005902.2 filed Jul. 23, 2015 Office Action dated Jul. 19, 2016.
CN 201480005902.2 filed Jul. 23, 2015 Office Action dated May 12, 2017.
EP 14743846.9 filed Aug. 12, 2015 Extended European Search Report dated Oct. 10, 2016.
EP 14743846.9 filed Aug. 12, 2015 Intent to Grant dated Jun. 26, 2017.
Goldstein, D. J. et. al. "Implantable Left Ventricular Assist Devices" (Nov. 19, 1998).
JP 2015-555266 filed Jul. 22, 2015 Office Action dated May 2, 2018.
JP 2015-555266 filed Jul. 22, 2015 Office Action dated Oct. 12, 2017.
Moran, J. E. "Subcutaneous Vascular Access Devices" (Nov. 1, 2001).
PCT/US2014/012721 filed Jan. 23, 2014 International Search Report and Written Opinion dated Apr. 14, 2014.
PCT/US2017/061179 filed Nov. 10, 2017 International Search Report and Written Opinion dated Jan. 22, 2018.
Rosenblatt, M. et. al. "Efficacy and Safety Results with the LifeSite Hemodialysis Access System versus the Tesio-Cath Hemodialysis Catheter at 12 Months"—Mar. 2006.
Sandhu, J. Dialysis Ports: A New Totally Implantable Option for Hemodialysis Access—Jun. 2002.
U.S. Appl. No. 14/162,113, filed Jan. 23, 2014 Final Office Action dated Jul. 2, 2018.
U.S. Appl. No. 14/162,113, filed Jan. 23, 2014 Final Office Action dated May 25, 2017.
U.S. Appl. No. 14/162,113, filed Jan. 23, 2014 Non-Final Office Action dated Dec. 11, 2017.
U.S. Appl. No. 14/162,113, filed Jan. 23, 2014 Non-Final Office Action dated May 4, 2016.
U.S. Appl. No. 14/162,113, filed Jan. 23, 2014 Non-Final Office Action dated Nov. 22, 2016.
"Merge". Merriam-Webster Dictionary. https://www.merriam-webster.com/dictionary/merge. Access May 13, 2021. (Year 2021).
PCT/US2019/027301 filed Nov. 12, 2020 Extended European Search Report dated Oct. 11, 2021.
U.S. Appl. No. 15/809,879, filed Nov. 10, 2017 Final Office Action dated May 18, 2021.
U.S. Appl. No. 15/809,879, filed Nov. 10, 2017 Final Office Action dated Oct. 4, 2021.
EP 17870333.6 filed Jun. 7, 2019 Supplemental European Search Report dated May 26, 2020.
U.S. Appl. No. 15/809,879, filed Nov. 10, 2017 Final Office Action dated Nov. 5, 2020.
U.S. Appl. No. 15/809,879, filed Nov. 10, 2017 Non-Final Office Action dated Jun. 10, 2020.
U.S. Appl. No. 29/716,554, filed Dec. 10, 2019 Notice of Allowance dated Feb. 6, 2020.

\* cited by examiner

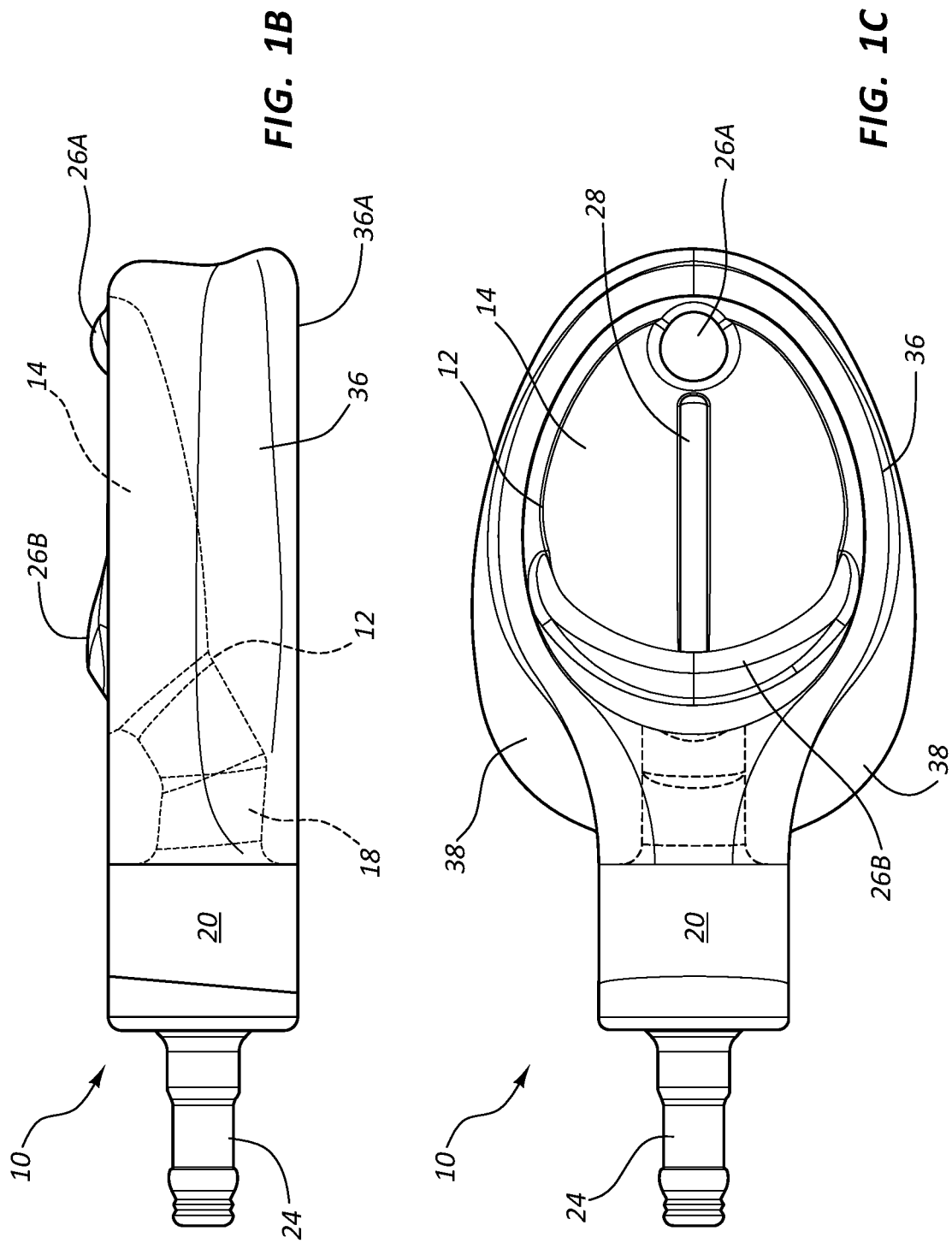

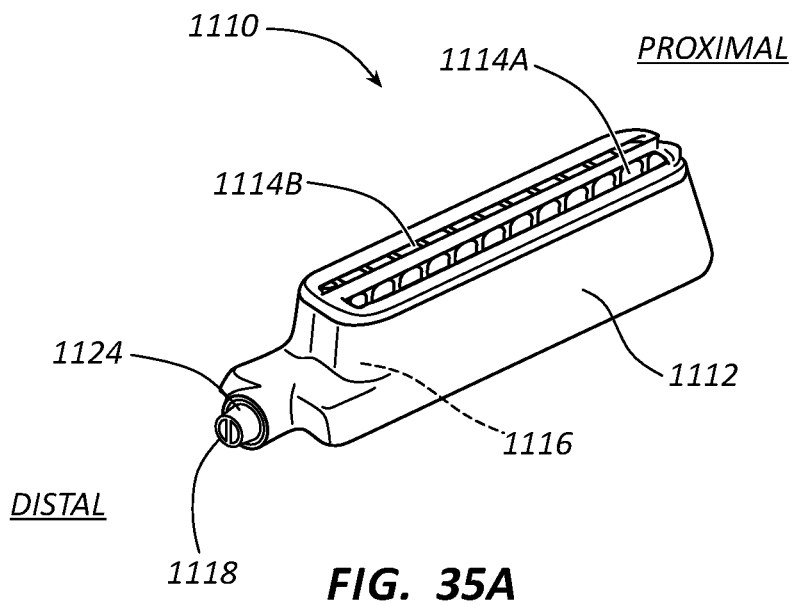
FIG. 35A
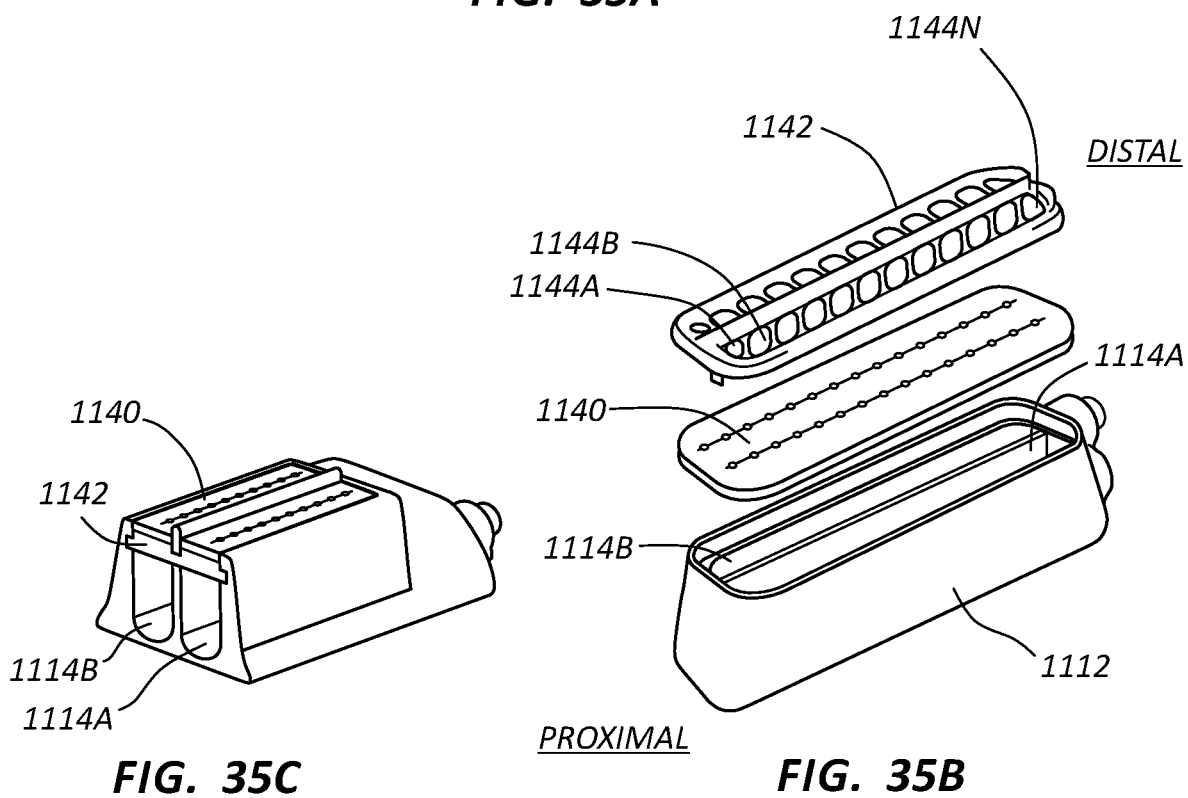
FIG. 35C
FIG. 35B

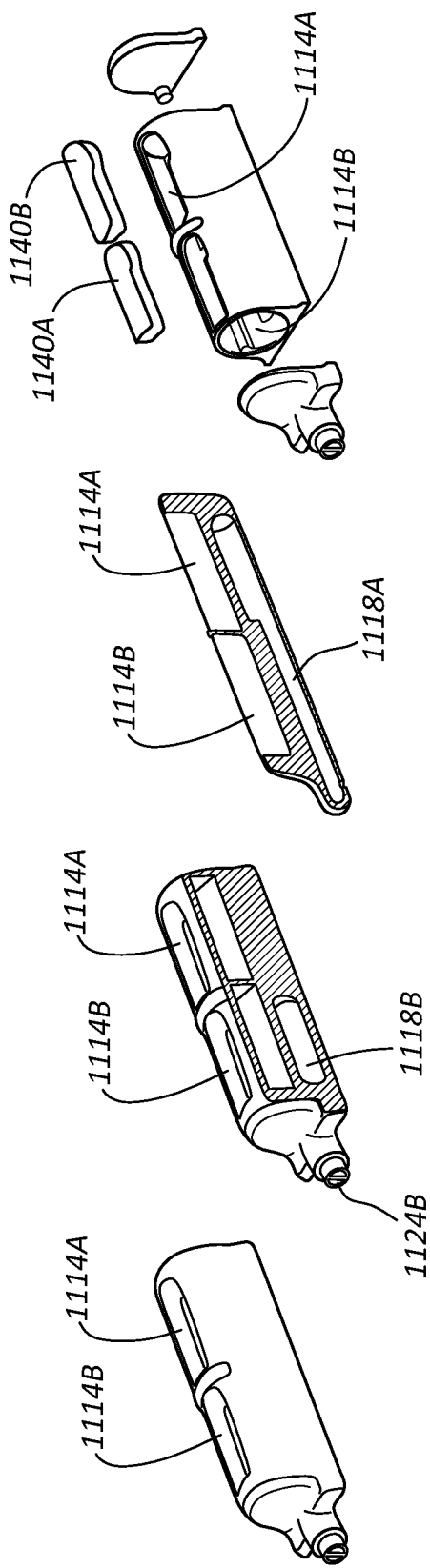
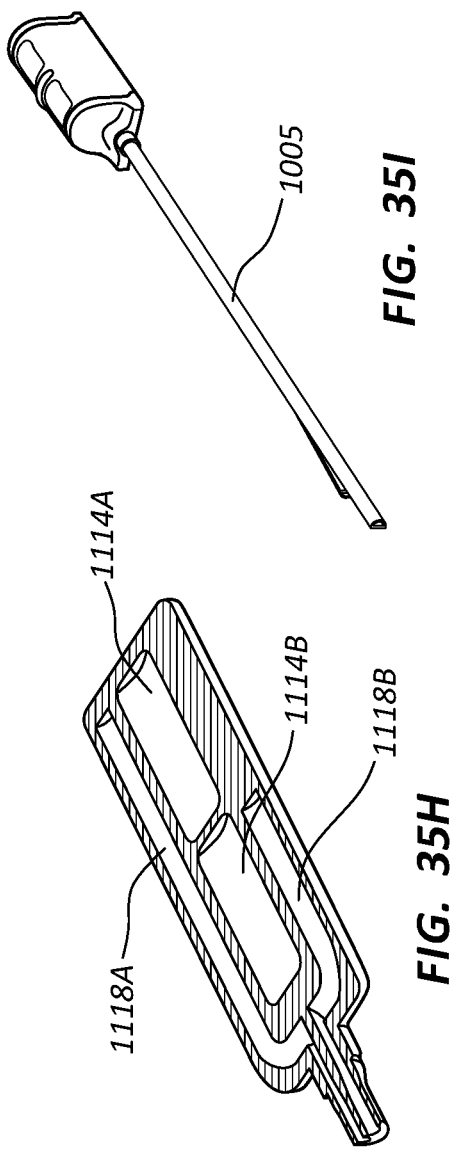

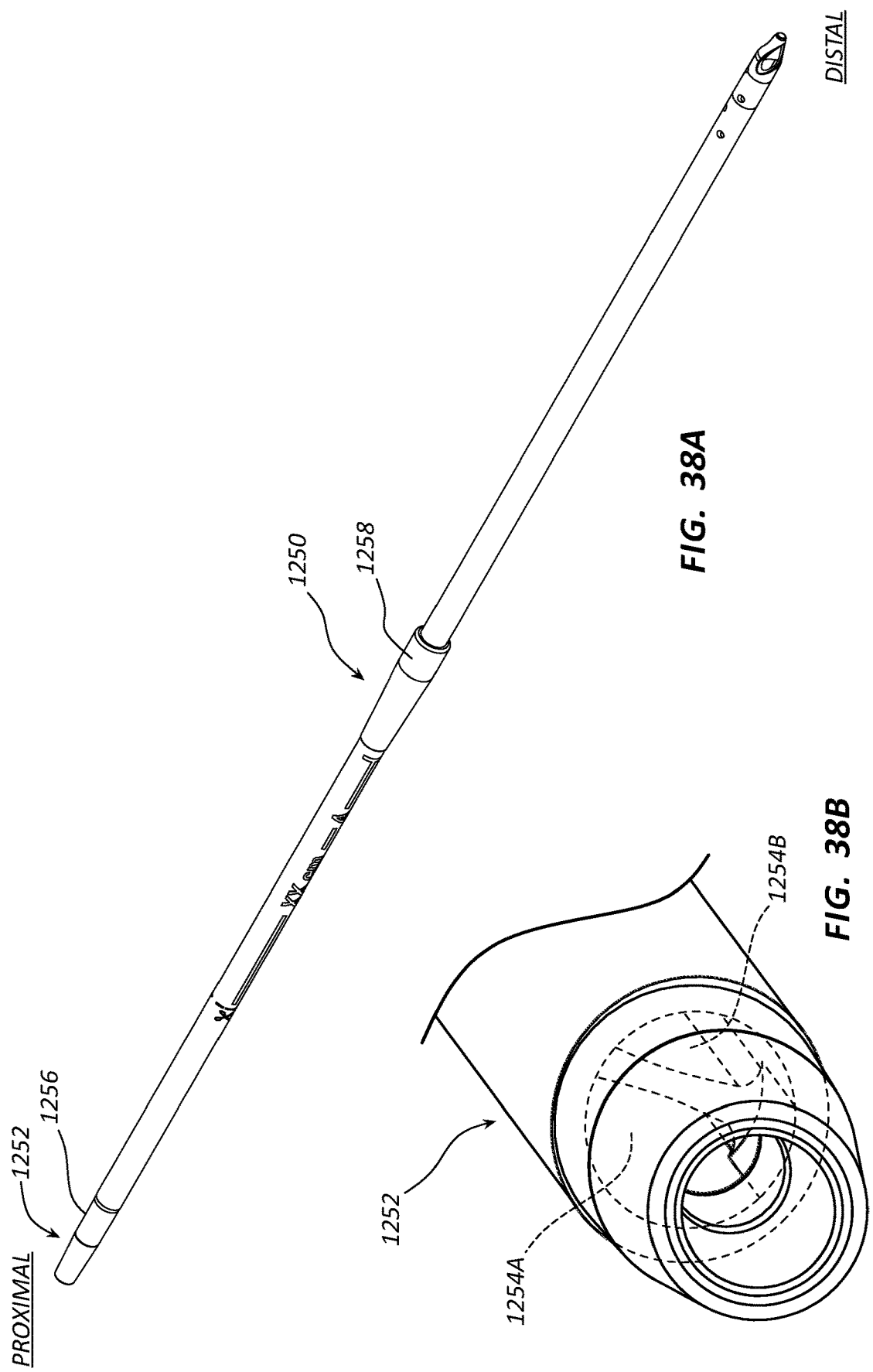

LOW-PROFILE SINGLE AND DUAL VASCULAR ACCESS DEVICE

CROSS-REFERENCE TO RELATED APPLICATIONS

This application is a continuation-in-part of U.S. patent application Ser. No. 15/809,879, filed Nov. 10, 2017, now U.S. Pat. No. 11,420,033, which claims the benefit of U.S. Provisional Application No. 62/421,131, filed Nov. 11, 2016, and U.S. Provisional Application No. 62/552,681, filed Aug. 31, 2017, and which is a continuation-in-part of U.S. patent application Ser. No. 14/162,113, filed Jan. 23, 2014, now U.S. Pat. No. 10,463,845, which claims the benefit of U.S. Provisional Application No. 61/755,913, filed Jan. 23, 2013. This application also claims the benefit of U.S. Provisional Application No. 62/657,662, filed Apr. 13, 2018, and U.S. Provisional Application No. 62/732,928, filed Sep. 18, 2018. Each of the aforementioned applications is incorporated by reference into this application.

BRIEF SUMMARY

Briefly summarized, embodiments of the present invention are directed to a low-profile access port for subcutaneous implantation within the body of a patient. The access port includes a receiving cup that provides a relatively large subcutaneous target to enable a catheter-bearing needle to access the port without difficulty. In addition, the access port includes a valve/seal assembly to permit pressurized fluid injection through the port while preventing backflow.

In an aspect of the invention a device is provided that allows immediate subcutaneous dialysis access while allowing patients to bathe and shower. Such a device reduces costs and time associated with cleaning and maintenance relative to traditional tunneled dialysis catheter positioned external to the body.

In an aspect of the invention, a device is provided enabling long-term dialysis while minimizing skin trauma. Typical infusion or apheresis port interfaces forces a clinician to access the approximately the same locus every time the port is accessed. Dialysis is typically required multiple times per week. Embodiments of an implantable dialysis port is provided that allows for multiple needle insertion sites, thereby reducing trauma to a single locus on the skin.

In an aspect of the invention, a low-profile access port comprises a body including a conduit with an inlet port at a proximal end thereof, and a receiving cup. The receiving cup is concavely shaped to direct a catheter-bearing needle into the conduit via the inlet port. The receiving cup is oriented substantially toward a skin surface when subcutaneously implanted within the patient to ease needle impingement thereon. A valve/seal assembly disposed in the conduit enables passage of the catheter therethrough while preventing fluid backflow.

In an aspect of the invention, a low-profile access port for subcutaneous implantation within the patient is disclosed and comprises a body including a conduit with an inlet port at a proximal end thereof, and a receiving cup. The receiving cup is funnel shaped to direct a catheter-bearing needle into the conduit via the inlet port. The conduit is defined by the body and extends from the inlet port to an outlet defined by a stem. A bend in the conduit enables catheter advancement past the bend while preventing needle advancement. A valve/seal assembly is also disposed in the conduit and enables passage of the catheter therethrough while preventing fluid backflow. The body includes radiopaque indicia configured to enable identification of the access port via x-ray imaging.

In an aspect of the invention, a low-profile access port is disclosed and comprises a body including a first set of receiving cups, a first set of inlet ports, each receiving cup of the first set of receiving cups in fluid communication with an inlet port of the first set of inlet ports, each receiving cup concavely shaped to direct an impinging needle toward the inlet port. A first conduit in fluid communication with each inlet port of the first set of inlet ports, the first conduit extending from the first set of inlet ports to a first outlet of a port stem and a catheter in fluid communication with the first outlet.

In some embodiments, a second set of receiving cups are in fluid communication with an inlet port of the second set of inlet ports, and a second conduit in fluid communication with each inlet port of the second set of inlet ports, the second conduit extending from the second set of inlet ports to a second outlet of the port stem. The first set of receiving cups are proximal to the second set of receiving cups. A perimeter of each receiving cup of the first set of receiving cups lies in a plane, and wherein the plane of the perimeter of each receiving cup is angled with respect to one another. A perimeter of each receiving cup of the first set of receiving cups lies in a plane, and wherein the plane of the perimeter of each receiving cup is co-planar with respect to one another. A perimeter of each receiving cup of the first set of receiving cups includes a cutout, the cutout between adjacent receiving cups providing communication therebetween.

In an aspect of the invention, a dialysis catheter assembly is disclosed and comprises a catheter having a first lumen and a second lumen, a bifurcation hub having a distal end in communication with a proximal end of the catheter, a first extension leg and a second extension leg connected to a distal end of the bifurcation hub, the first extension leg in fluid communication with the first lumen, the second extension leg in fluid communication with the second lumen. A first port including a first receiving cup defining a first perimeter substantially parallel to the skin surface following implantation of the dialysis catheter assembly, the first port including a first outlet in fluid communication with the first receiving cup, the first outlet in fluid communication with the first extension leg. A second port separated from the first port, the second port including a second receiving cup defining a second perimeter substantially parallel to the skin surface following implantation of the dialysis catheter assembly, the second port including a second outlet in fluid communication with the second receiving cup, the second outlet in fluid communication with the second extension leg.

In some embodiments, the first receiving cup includes a first septum covering the first perimeter, and the second receiving cup includes a second septum covering the second perimeter, the first septum and the second septum providing a continuous outer profile to the first port and the second port.

In an aspect of the invention, a subcutaneous dialysis port is disclosed and comprises, a catheter having a first lumen and a second lumen, a bifurcation hub having a distal end in communication with a proximal end of the catheter. A first elongate arm and a second elongate arm connected to a distal end of the bifurcation hub, the first elongate arm in fluid communication with the first lumen, the second elongate arm in fluid communication with the second lumen, each of the first elongate arm and the second elongate arm including a needle penetrable portion in an upper wall thereof.

In some embodiments, a lower wall of the first elongate arm and the second elongate arm are formed of a compliant material that allows the first and second elongate arm to conform to a contour of a patient's body. The first elongate arm and the second elongate arm each include an end cap disposed at the proximal end thereof, each end cap including at least one of a palpation feature and an indicia, the indicia observable under a suitable imaging modality. The at least one of the palpation feature and the indicia indicating a flow direction to a user. The needle penetrable portion includes a self-sealing silicone material. A lower wall of the first elongate arm and the second elongate arm are formed of a needle impenetrable material.

In an aspect of the invention, a vascular access device for subcutaneous implantation is disclosed and comprises a catheter having a first lumen and a second lumen, an elongate body defining a first elongate chamber and a second elongate chamber, the first elongate chamber in fluid communication with the first lumen and the second elongate chamber in fluid communication with the second lumen. A needle penetrable septum is disposed over an opening in an upper surface of the elongate body, the opening providing access to the first elongate chamber and the second elongate chamber. A needle impenetrable guide disposed over the opening and the needle penetrable septum, the needle impenetrable guide including a plurality of first openings positioned over the first elongate chamber, and a plurality of second openings positioned over the second elongate chamber.

In some embodiments, the elongate body has a length and a width, the length more than two times greater than the width. The first elongate chamber and the second elongate chamber extend in a side-by-side arrangement relative to a longitudinal axis of the elongate body. The first elongate chamber and the second elongate chamber are in a tandem arrangement relative to a longitudinal axis of the elongate body such that the first elongate chamber is proximal to the second elongate chamber. The impenetrable needle guide is disposed at least partially within the needle penetrable septum. The impenetrable needle guide does not penetrate the needle penetrable septum. The plurality of first openings are parallel to the plurality of second openings.

In an aspect of the invention, a port assembly is disclosed comprising a first conduit including a first receiving cup at a proximal end and a first nozzle at a distal end, wherein a first valve assembly is disposed between the first receiving cup and the first nozzle. A second conduit including a second receiving cup at a proximal end and a second nozzle at a distal end, wherein a second valve assembly is disposed between the second receiving cup and the second nozzle. An outer shell surrounding the first conduit and the second conduit, the outer shell including a proximal portion surrounding the first receiving cup and the second receiving cup, and the distal portion surrounding the first nozzle and the second nozzle, the proximal portion, the distal portion, the first conduit, and the second conduit connected via press fit engagement.

In some embodiments, the distal portion of the outer shell includes a distal receiving slot designed to receive a stem assembly. The stem assembly includes a housing having a proximal end designed for insertion into the distal receiving slot, and wherein the stem assembly is connected to the distal portion of the outer shell via press fit engagement. The stem assembly includes a first stem and a second stem extending from a distal end of the housing, the first stem in fluid communication with the first receiving cup, and the second stem in fluid communication with the second receiving cup. The port assembly further comprising a catheter including a first lumen designed for insertion over the first stem, a second lumen designed for insertion over the second stem, and a locking member designed to couple the stem assembly to the catheter. The stem assembly includes a first slot on an upper portion and a second slot on a lower portion, and wherein the locking member includes a first protrusion designed to snap-fit in the first slot, and a second protrusion designed to snap-fit in the second slot. The outer shell, the housing, and the locking member together provide a smooth continuous outer surface.

In light of the above, embodiments herein are generally directed to a vascular access device, also referred to herein as an access port, for subcutaneous implantation within the body of a patient. The implanted access port is transcutaneously accessible by a catheter-bearing needle, such as a peripheral intravenous ("Hy") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1E show various views of an access port according to one embodiment;

FIGS. 35A-35J depict various views of a low-profile vascular access device according to one embodiment;

FIGS. 38A-38B depict various views of the catheter of the device of FIG. 36A.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an access port for subcutaneous implantation within the body of a patient. The implanted access port is transcutaneously accessible by a catheter-bearing needle, such as a peripheral intravenous ("PIV") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter, e.g. dialysis or similar extracorporeal treatment.

In accordance with one embodiment, the access port defines a low profile so as to facilitate ease of placement within the subcutaneous tissue of the patient. Further, the access port is configured to provide a relatively large subcutaneous target to enable the PIV catheter or other suitable catheter-bearing needle to access the port without difficulty. In addition, the access port includes a valve/seal assembly to permit the injection of fluids through the access port at a relatively high flow rate, such as about 5 ml per second at a pressure of about 300 psi (also referred to herein as "power injection"). Possible applications for the access port described herein include administration of medicaments and other fluids to the patient, pheresis/apheresis/dialysis or similar extracorporeal treatments that enable fluid to be infused into or removed from the patient's vasculature, fluid aspiration, etc.

Figure 1A:
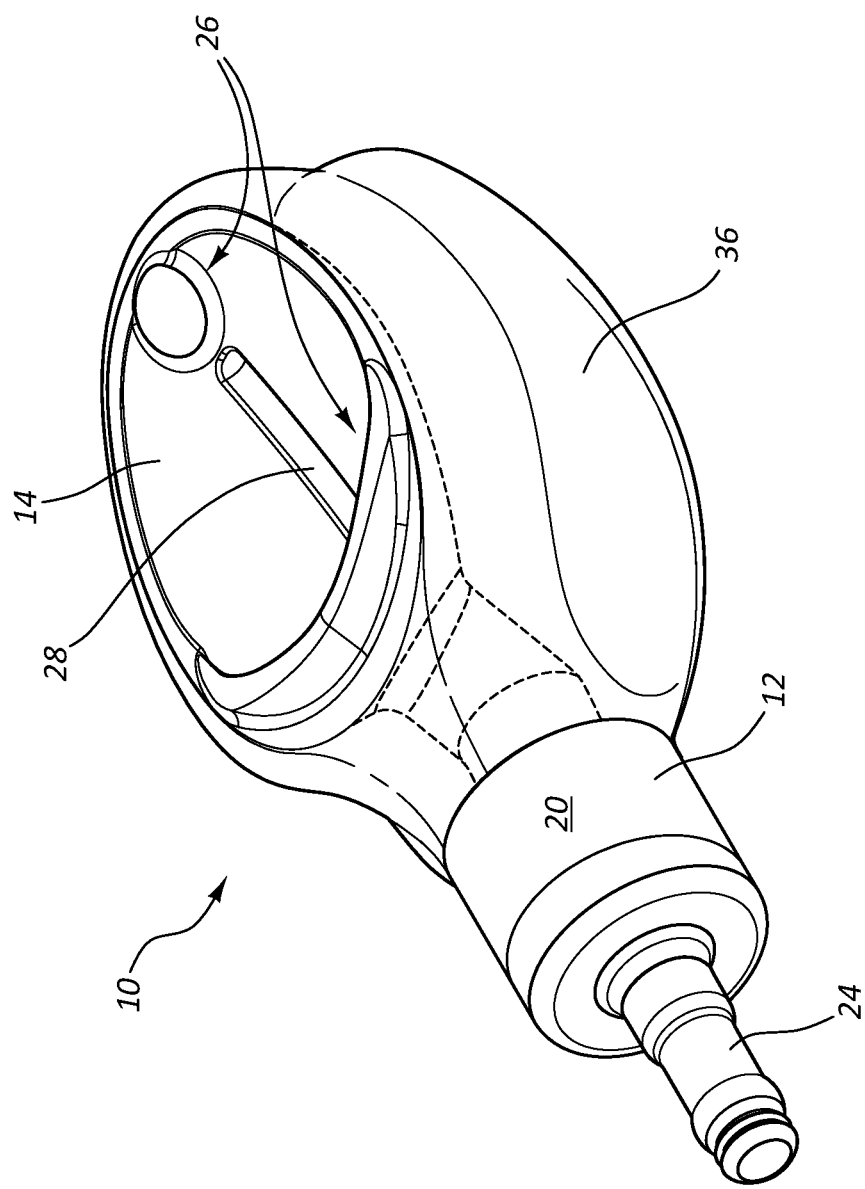
Figure 1D:
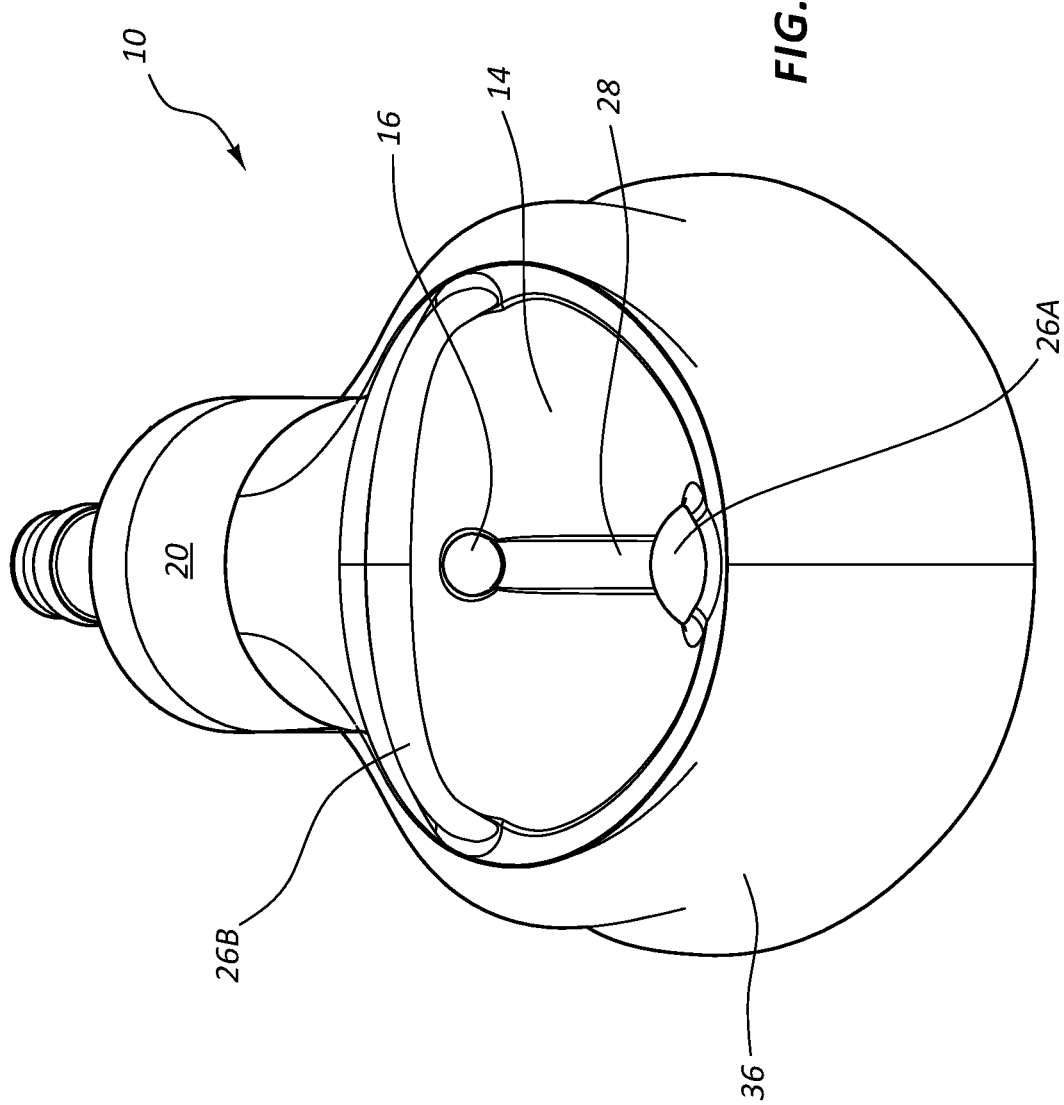
Figure 1E:
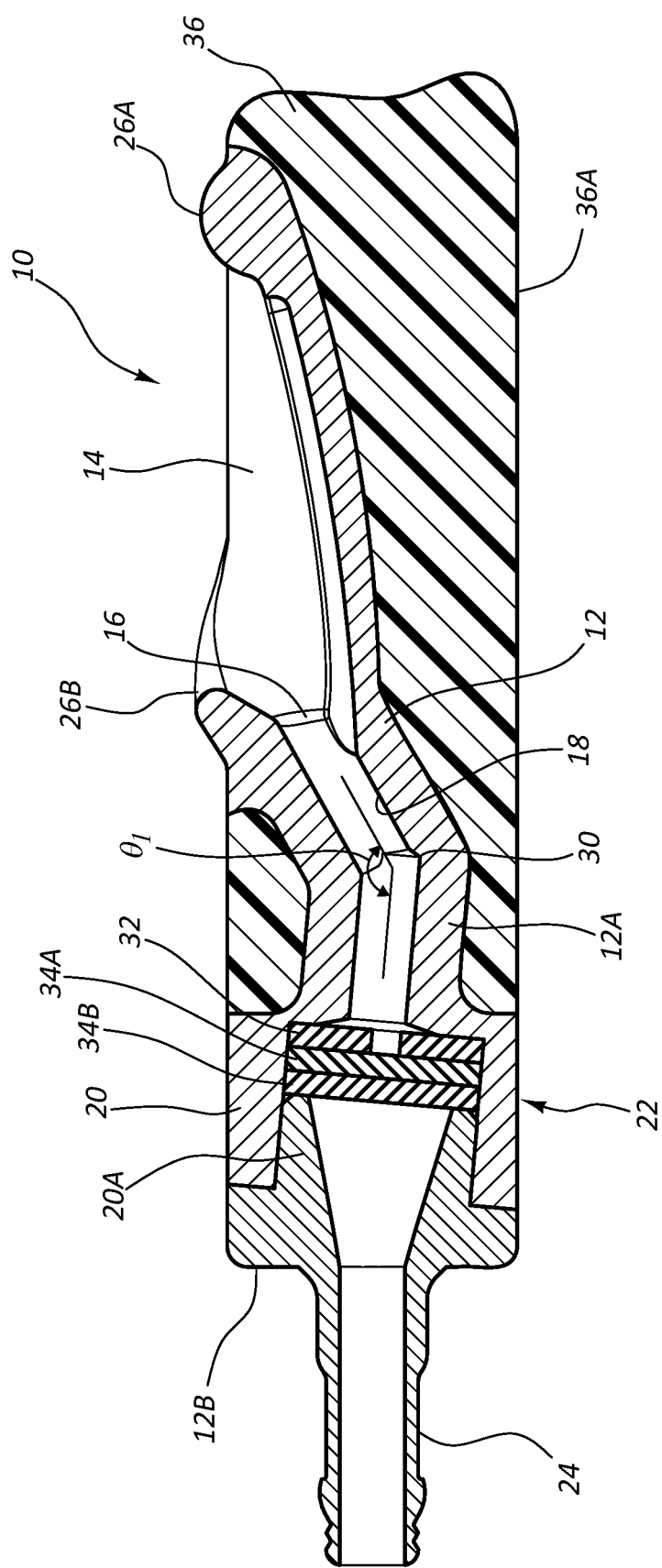

Reference is first made to FIGS. 1A-1E, which show various details of an access port, generally designated at 10, in accordance with one embodiment. As shown, the port 10 includes a body 12 that is defined in the present embodiment by a first portion 12A and a second portion 12B (FIG. 1E). In the present embodiment the port body 12 includes a metal such as titanium, and as such, the second portion 12B is press fit into engagement with the first portion 12A to define the body, though it is appreciated that the port body can include a variety of other materials, including metals, thermoplastics, ceramics, etc.

Figure 2:
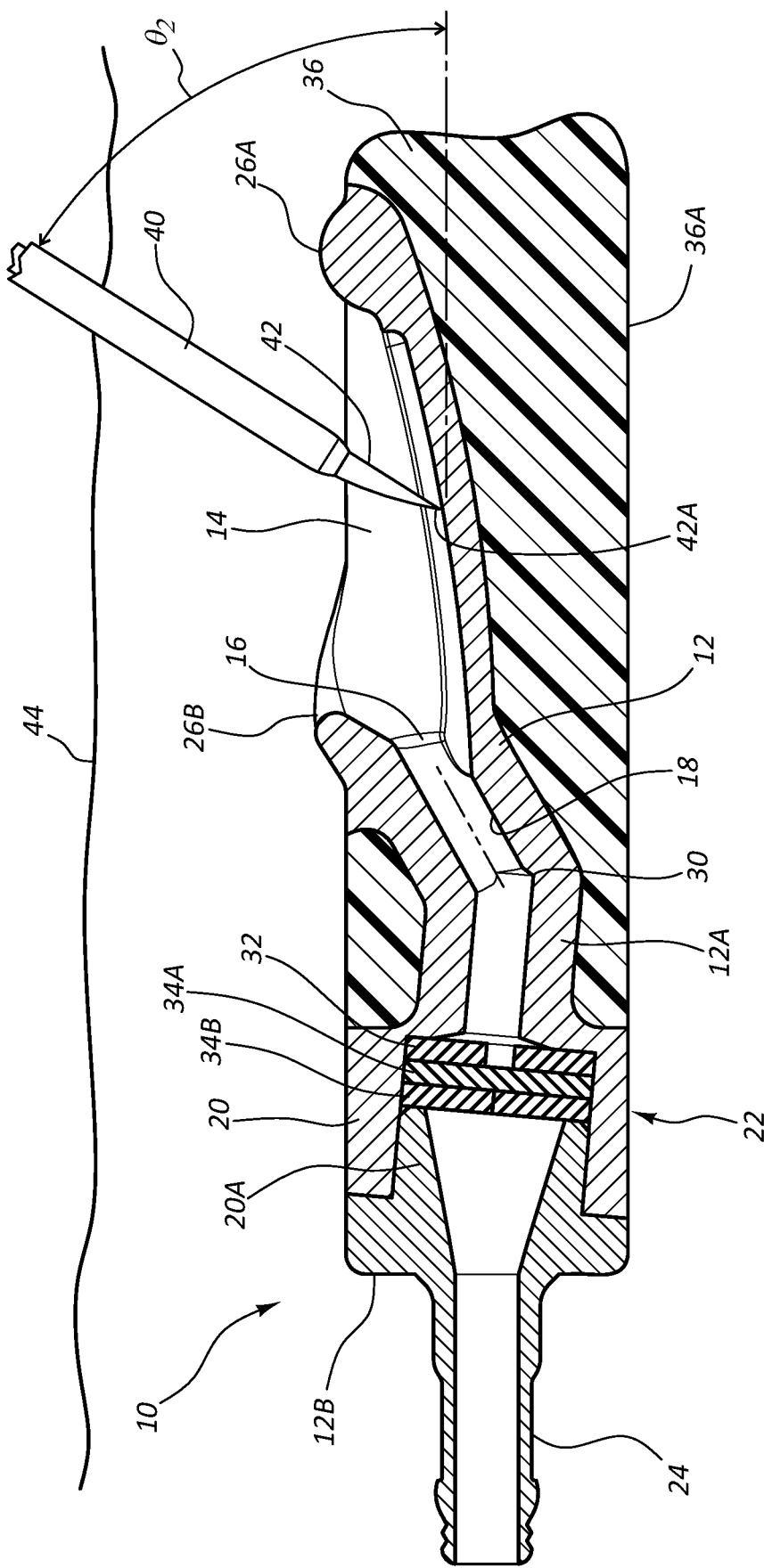
FIG. 2 is a cross sectional view of the access port of FIGS. 1A-1E.

The port body 12 defines in the present embodiment a substantially concavely-shaped receiving cup 14 for receiving and directing a catheter-bearing needle (FIG. 2) to operably connect with the port 10, as described further below. In particular, the substantially concave shape of the receiving cup 14 is configured to direct a catheter-bearing needle (FIG. 2) impinging thereon toward an inlet port 16 that serves as an opening for a conduit 18 defined by the port body 12. The open and shallow nature of the receiving cup 14 together with its substantially upward orientation (i.e., toward the skin surface of the patient), so that it is substantially parallel to the skin surface when subcutaneously implanted under the skin of the patient (i.e., the receiving cup is substantially parallel to the skin surface when the skin is at rest, or undeformed by digital pressure or manipulation), enables the receiving cup to present a large, easily accessible target for the needle when introduced into the skin, as seen in FIG. 2. FIG. 2 further shows that the port 10 defines a relatively low profile height, which enables relatively shorter needle lengths to be used for accessing the port after implantation. It will be appreciated that the port 10, port body 12, funnel 14, portions thereof, or the like, can be constructed of a suitable biocompatible material. Further, the port 10, or portions thereof can include metals, for example titanium. Such metals can be biocompatible, radiopaque, and/or resistant to gouging from an impinging needle, as will be discussed in more detail herein. By way of example, the port 10, port body 12, funnel 14, portions thereof that include titanium, can be machined, can be formed by injection-molding powdered titanium, or manufactured via other suitable methods.

Palpation features 26 are included with the port body 12 to assist a clinician to locate and/or identify the port 10 via finger palpation after implantation under the skin of the patient. In detail, the palpation features 26 in the present embodiment include a bump 26A disposed near the proximal end of the receiving cup 14 and a ridge 26B disposed above and curving around a distal portion of the receiving cup. FIG. 1B shows that the palpation features extend above the general upper plane defined by the port 10 so as to facilitate palpation of the features by a clinician in order to locate the position and/or orientation of the receiving cup 14. Note that a variety of other sizes, configurations, numbers, etc., of palpation features can be included on the port in addition to what is shown and described herein.

A guide groove 28 is defined on the receiving cup 14 and is longitudinally aligned with the inlet port 16 of the conduit 18. The guide groove 28 is defined as a depression with respect to adjacent portions of the surface of the receiving cup 14 and extends distally along the receiving cup surface from a proximal portion of the receiving cup so as to provide a guide path to guide the distal tip of the catheter-bearing needle toward the inlet port 16 once impingement of the needle into the guide groove is made. This in turn reduces the chance the needle will slide across and off the receiving cup 14 during insertion. Note that these and other similar features, though differing in shape and configuration, can also be included on the other ports disclosed herein.

As best seen in FIG. 1E, the port body 12 further defines the conduit 18 as a pathway into which a transcutaneously inserted catheter can pass so as to place the catheter in fluid communication with the port 10. As shown, the conduit 18 is in communication with the receiving cup 14 via the inlet port 16. A first conduit portion 18A of the conduit 18 distally extends from the inlet port 16 in an angled downward direction from the perspective shown in FIG. 1E to a bend 30, where a second conduit portion 18B of the conduit angles slightly upward and changes direction at a predetermined angle $\theta_1$. Note that angle orientation $\theta_1$ in one embodiment is about 37 degrees, but can vary from this in other embodiments, including angles less than 37 degrees in one embodiment. The magnitude of angle $\theta_1$ depends in one embodiment on various factors, including the size of the catheter and/or needle to be inserted into the port conduit, the size of the conduit itself, etc.

The conduit 18 then extends to and through a cavity 20A defined by a valve housing 20 of the port body. The conduit 18 extends to a distal open end of the stem 24 of the port 10. The conduit 18 is sized so as to enable the catheter 40 (FIG. 2) to pass therethrough, as will be seen.

As mentioned, the valve housing 20 defines a cavity 20A through which the conduit passes and which houses a valve/seal assembly 22. The valve/seal assembly 22 includes a sealing element, or seal 32, which defines a central hole through which the catheter 40 can pass, a first slit valve 34A and a second slit valve 34B. The seal 32 and valves 34A, 34B are sandwiched together in one embodiment and secured in place within the cavity 20A as shown in FIG. 1E. The slits of the slit valves 34A, 34B are rotationally offset from one another by about 90 degrees in the present embodiment, though other relationships are possible.

The seal 32 and valves 34A, 34B of the valve/seal assembly 22 cooperate to enable fluid-tight passage therethrough of the catheter 40 (FIG. 2) while also preventing backflow of fluid through the valve/seal assembly. Indeed, in one embodiment the seals disclosed herein prevent fluid flow around the external portion of the catheter when the catheter is disposed through the seal, while the valves are suitable for preventing fluid flow when no catheter passes through them. As such, when the catheter 40 is not inserted therethrough the valve/seal assembly 22 seals to prevent passage of air or fluid. In the present embodiment, the seal 32 and valves 34A, 34B include silicone, though other suitably compliant materials can be employed.

The port 10 in the present embodiment includes an overmolded portion 36 that covers the port body 12. The overmolded portion 36 includes silicone or other suitably compliant material and surrounds the body 12 as shown so as to provide a relatively soft surface for the port 10 and reduce patient discomfort after port implantation. The overmolded portion 36 includes two predetermined suture locations 38, best seen in FIG. 1C, for suturing the port 10 to patient tissue, though sutures may be passed through other portions of the overmolded portion, if desired. The overmolded portion 36 further defines a relatively flat bottom surface 36A so as to provide a stable surface for the port 10 in its position within the tissue pocket after implantation. In contrast, the port shown in FIG. 3C includes a bottom surface with a slightly rounded profile.

FIG. 2 depicts details regarding the insertion of the catheter 40 disposed on the needle 42, according to one embodiment. After locating the port 10 via through-skin palpation of the palpation features 26, a clinician uses the catheter-bearing needle 42 to pierce a skin surface 44 and insert the needle until a distal tip 42A thereof impinges on a portion of the receiving cup 14, as shown. Note that, because of the orientation of the receiving cup 14 as substantially parallel to the skin surface, the needle 42 can impinge on the receiving cup at an insertion angle $\theta_2$ that is relatively steep, which facilitates ease of needle insertion into the body. Indeed, in one embodiment a needle inserted substantially orthogonally through the skin of the patient can impinge the receiving cup of the access port.

The needle 42 is manipulated until the distal tip 42A is received into the guide groove 28, which will enable the distal tip to be guided along the groove to the inlet port 16. The needle 42 is then inserted through the inlet port 16 and into the first portion 18A of the conduit 18 until it is stopped by the bend 30. The needle 42 can then be proximally backed out a small distance, and the catheter 40 advanced over the needle such that the catheter bends and advances past the bend 30 into the second portion 18B of the conduit 18. Catheter advancement continues such that a distal end 40A of the catheter 40 advances into and past the hole of the seal 32 and through both slits of the slit valves 34A, 34B of the valve/seal assembly 40. Once the distal end 40A of the catheter 40 has extended distally past the valve/seal assembly 22, further advancement can cease and fluid transfer through the catheter 40 and port 10 can commence, including infusion and/or aspiration through the stem 24. Once fluid transfer is completed, the catheter 40 can be withdrawn proximally through the valve/seal assembly 22 and the conduit, then withdrawn through the surface 44 of the skin and out of the patient.

Figure 3A:
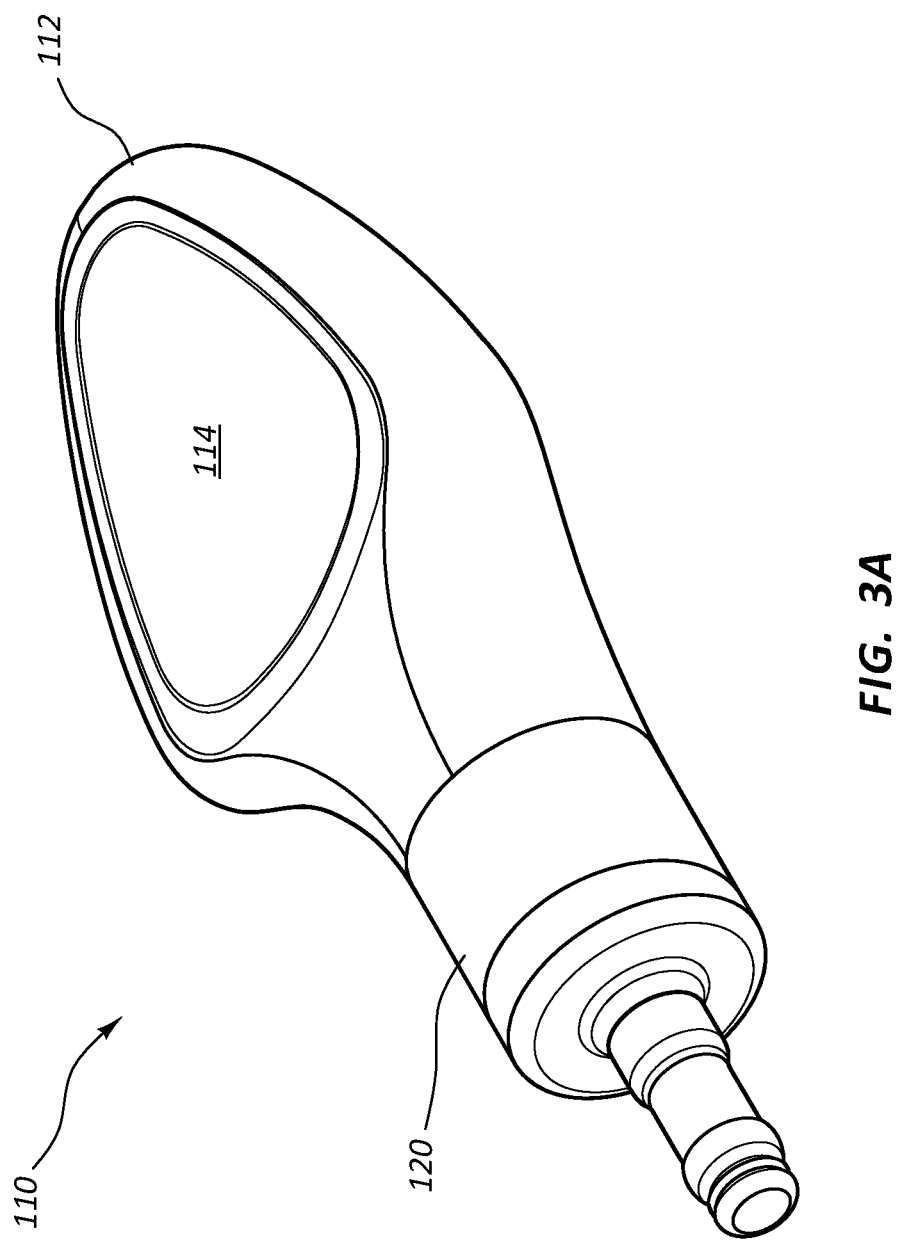
FIG. 3A-3C are various views of a low-profile access port according to one embodiment.
Figure 3B:
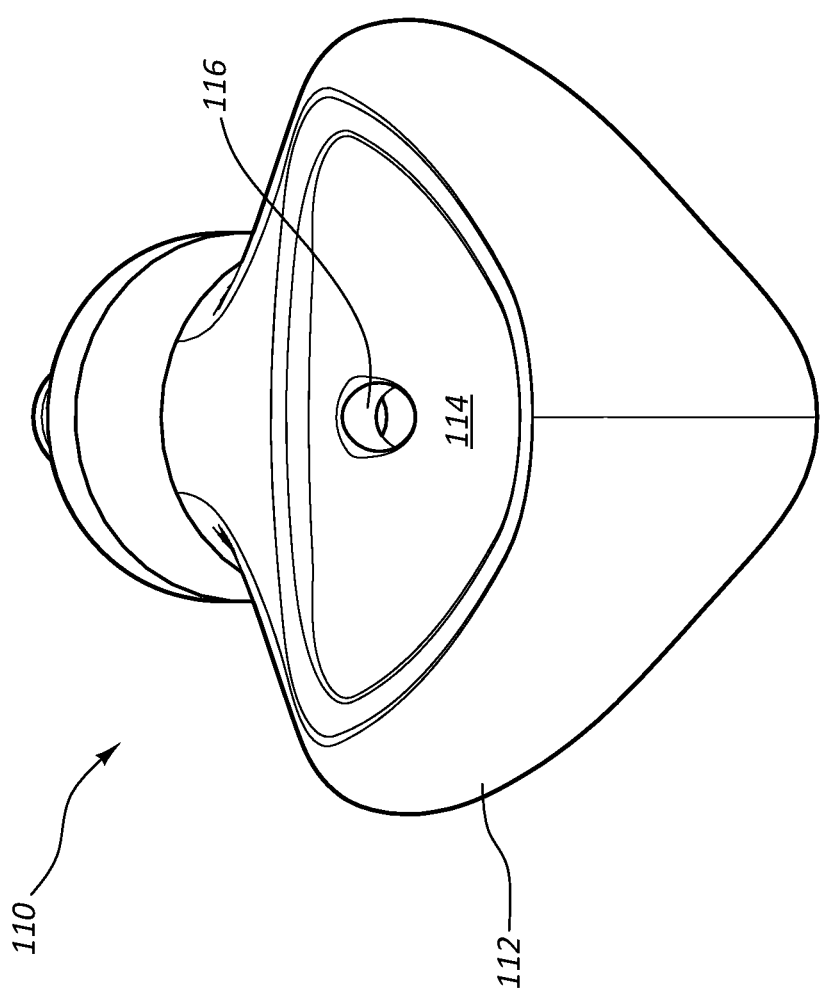
Figure 3C:
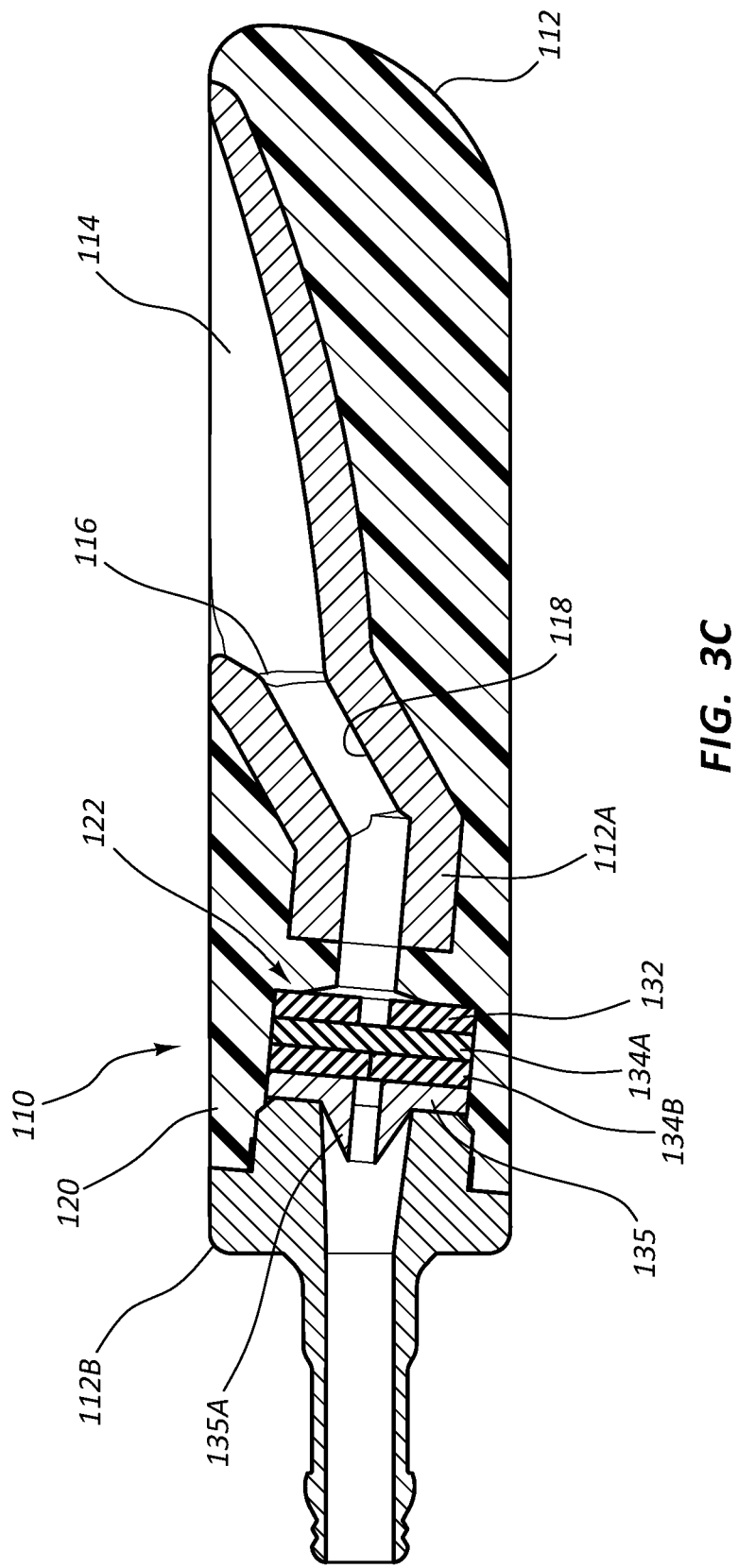

FIGS. 3A-3C depict details of an access port 110 according to another embodiment. Note that various similarities exist between the port 10 and the other ports shown and described herein. As such, only selected port aspects are discussed below. As shown, the port 110 includes a body 112 that in turn includes a first body portion 112A and a second body portion 112B, best seen in FIG. 3C. The body 112 in the present embodiment includes a thermoplastic, such as an acetyl resin in the present embodiment. As such, the first and second body portions 112A, 112B are ultrasonically welded to one another to define the body 12, in the present embodiment. As before, a receiving cup 114 is included with the body 112 and is operably connected to a conduit 118 via an inlet port 116. Also, note that a variety of materials can be used to define the port body, receiving cup, conduit, etc.

A valve/seal assembly 122 is disposed within a cavity 120A that is defined by a valve housing 120, which in the present embodiment, is defined by the first body portion 112A. The valve/seal assembly 122 includes a proximal seal 132 with a central hole for catheter passage, two slit valves 134A, 134B each with a slit arranged at a 90-degree offset with respect to the other, and a distal seal 135 with a central hole, also referred to herein as a sphincter seal.

The distal seal 135 includes on its distal surface a frustoconical portion 135A disposed about the seal central hole that is configured to provide a sphincter-like seal about the outer surface of a catheter when it extends through the valve/seal assembly. The frustoconical portion 135A is disposed such that any back-flowing fluid impinging on the frustoconical portion will cause the seal to secure itself about the outer surface of the catheter in an even tighter engagement, thus preventing backflow past the catheter outer surface when high fluid pressures are present, such as in the case of power injection. As mentioned, other valve/seal combinations can also be included in the valve/seal assembly.

In the present embodiment, the receiving cup 114 and portion of the conduit 118 proximal to the valve/seal assembly 122 both include a needle-impenetrable lining that prevents the distal end of a needle from gouging the surface when impinging thereon. This, in turn, prevents the undesirable creation of material flecks dug by the needle. Various suitable materials can be employed for the needle-impenetrable material, including glass, ceramic, metals, etc. In one embodiment, the components of the port 110 are all non-metallic such that the port is considered MRI-safe, by which the port does not produce undesired artifacts in MRI images taken of the patient when the port is in implanted therewithin.

Figure 4:
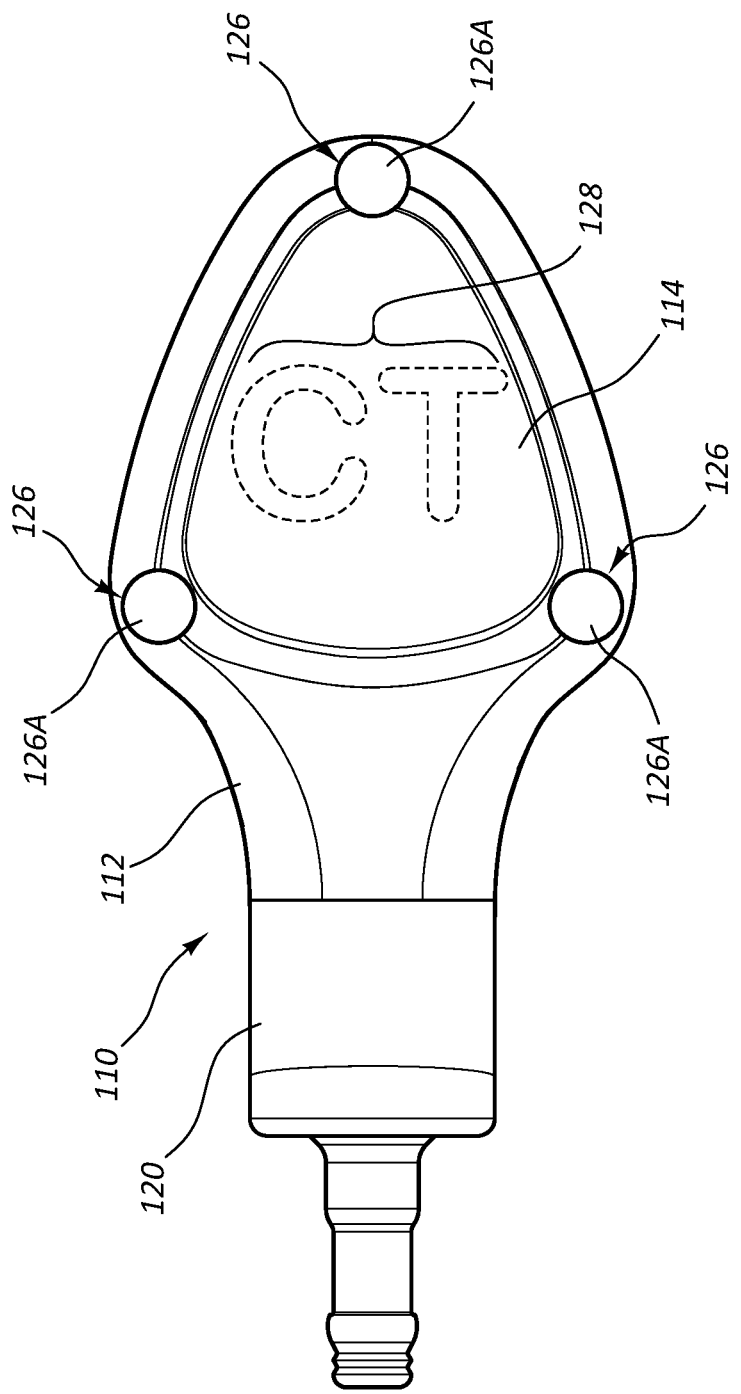
FIG. 4 is a top view of a low-profile access port according to one embodiment.

FIG. 4 depicts additional features of the port 110 according to another embodiment. As shown, in the present embodiment the receiving cup 18 includes radiopaque indicia 128 to indicate a characteristic of the port 110. Here, the radiopaque indicia 128 includes a "C" and a "T" that are formed by a radiopaque material, such as tungsten, bismuth trioxide, etc., so as to be visible after port implantation via x-ray imaging technology. For instance, the radiopaque material can be formed as an insert that is insert-molded included in the port body, as an initially flowable material that is injected into a cavity of the port body before hardening, etc. In embodiments where the port body is metallic, the radiopaque indicia can be formed by etching, engraving, or otherwise producing a relative thickness difference between the indicia and the surrounding port body material so as to produce an x-ray-discernible contrast that shows up in an x-ray image.

In the present embodiment, the CT radiopaque indicia 128 indicate to an observer that the port is capable of power injection of fluids therethrough. In addition to this characteristic, other characteristics can be indicated by various other types of indicia as appreciated by one skilled in the art.

Further, in the present embodiment the top view of the port 110 of FIG. 4 indicates that the port body 112 in the region surrounding the receiving cup 114 defines a generally triangular shape, which can be palpated by a clinician after implantation and can indicate not only the location of the receiving cup, but also a particular characteristic of the port, such as its ability to be used for power injection. Of course, the receiving cup may define shapes other than triangular in other embodiments.

FIG. 4 further shows that distributed about the perimeter of the receiving cup 114 are three palpation features 126, namely, three suture plugs 126A disposed in corresponding holes defined in the port body 112. The suture plugs 126A include raised silicone bumps in the present embodiment and can serve to locate the position of the receiving cup 114 post-implantation when they are palpated by a clinician prior to needle insertion into the patient. Various other palpation features could be included with the port, in other embodiments.

Figure 5:
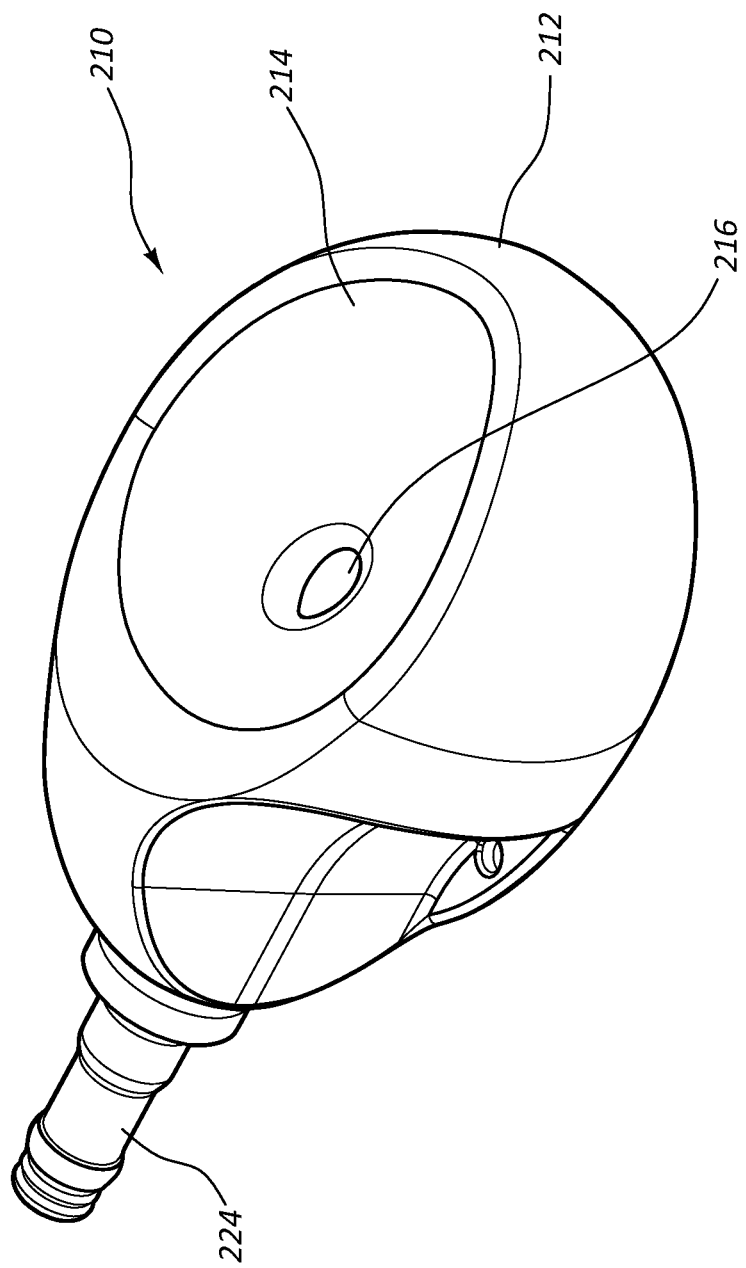
FIG. 5 is a perspective view of a low-profile access port according to one embodiment.

FIG. 5 depicts details of a low-profile port 210 according to one embodiment, including a body 212 defining a concavely-shaped receiving cup 214 and an inlet port 216 positioned slightly off-center with respect to the receiving cup. A stem 224 is included as a fluid outlet.

Figure 6:
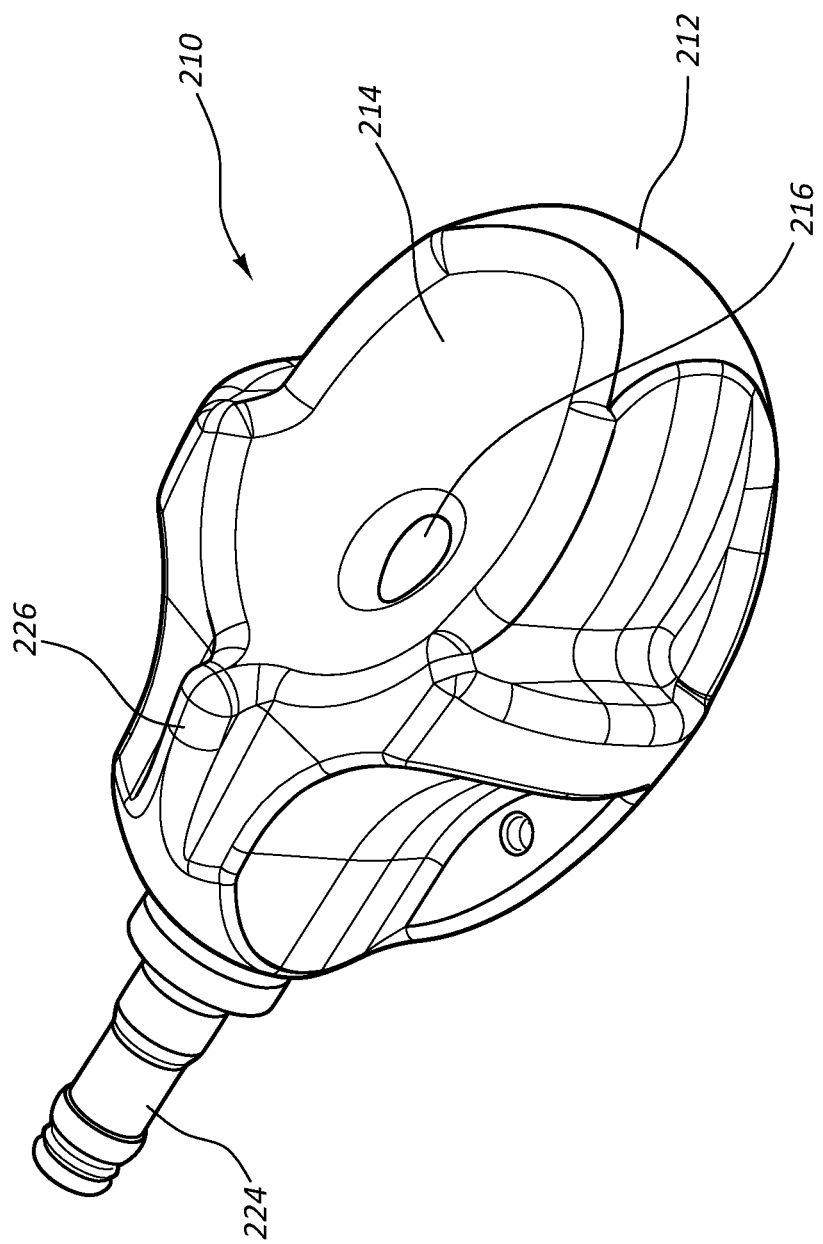
FIG. 6 is a perspective view of a low-profile access port according to one embodiment.

FIG. 6 depicts the low-profile port 210 according to another embodiment, wherein the body 212 defining additional surface features, including a raised palpation feature 226 distal to the receiving cup 214. In light of FIGS. 5 and 6, it is thus appreciated that the port can be configured in a variety of shapes and configurations to provide a low-profile solution for providing vascular access. Note also that the receiving cup shape, design, and configuration can vary from is explicitly shown and described herein.

Figure 7A:
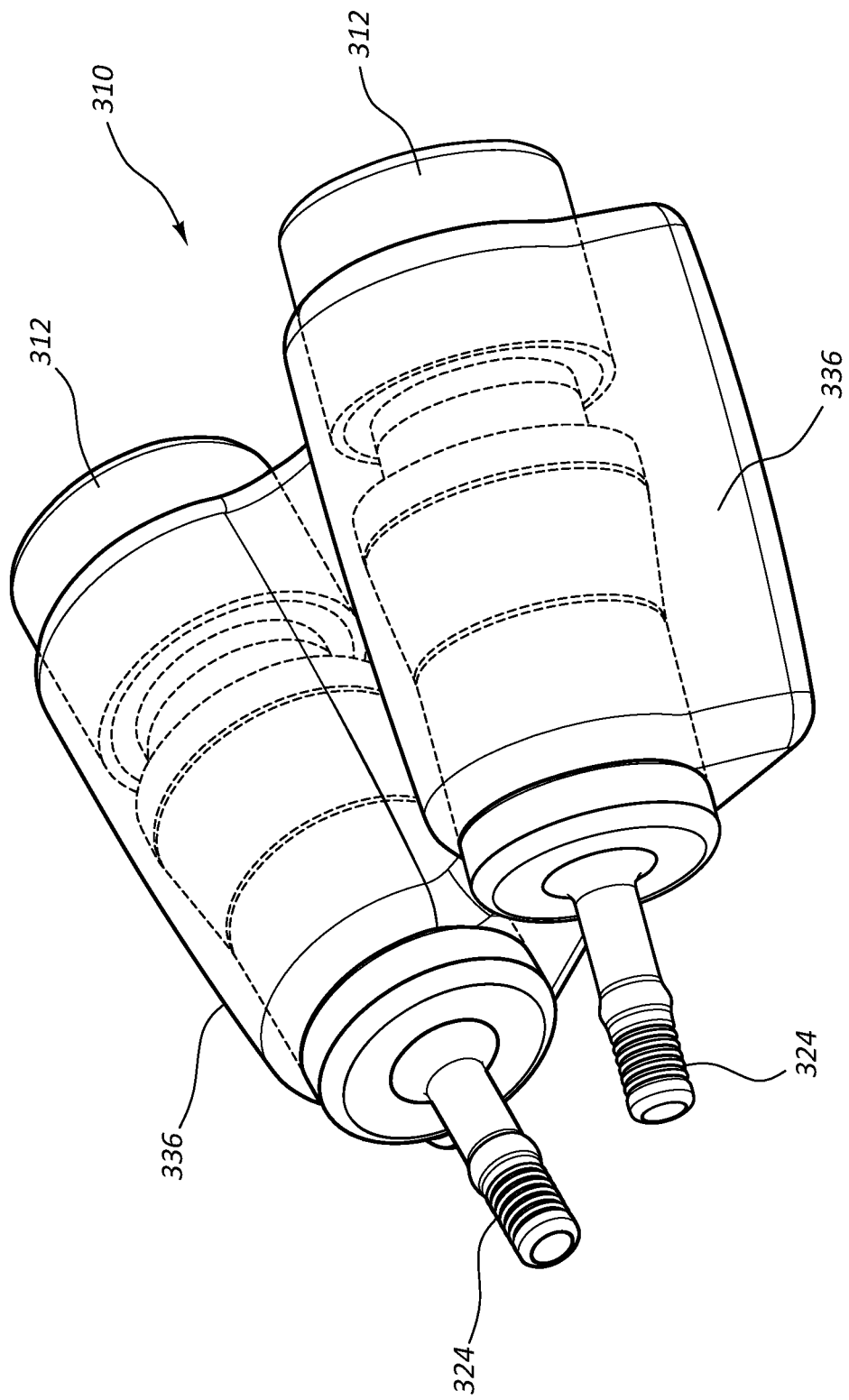
FIGS. 7A and 7B are various views of an access port according to one embodiment.
Figure 7B:
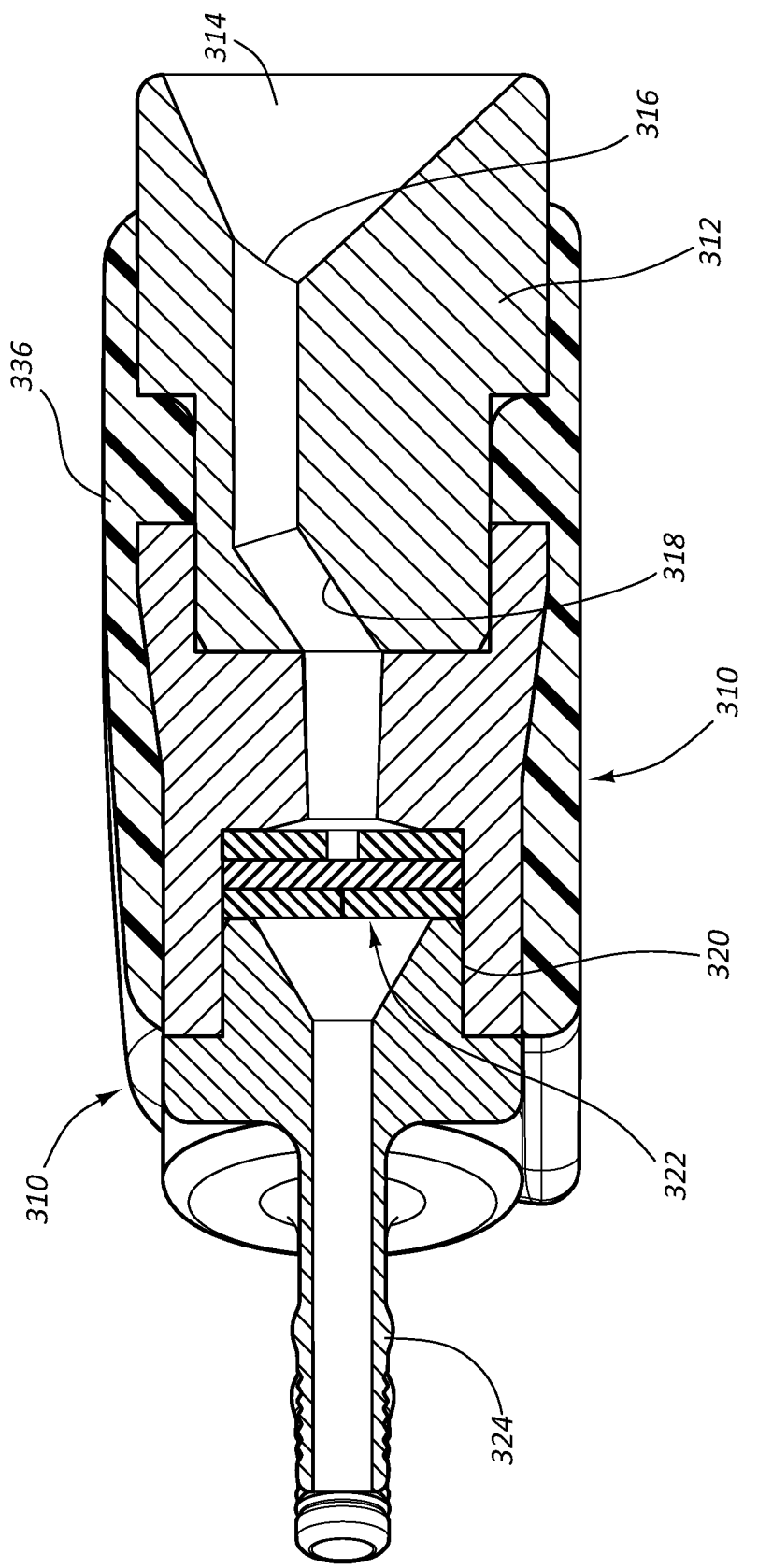

FIGS. 7A and 7B depict various details of a low-profile dual-body access port 310 according to one embodiment, wherein each of the port bodies 312 defines a receiving cup 314 that is laterally facing and includes an inlet port 316 leading to a conduit 318. The conduit 318 extends distally to a valve/seal assembly 322 disposed in a valve housing 320, which in the present embodiment, is defined by a portion of the body 312. The conduit 318 extends through the port 324. A compliant overmolded portion 324 covers portions of each body 312 of the port 310 and operably joins the bodies to one another. The bodies 312 can include any suitable material, including metal, thermoplastic, etc.

Figure 8A:
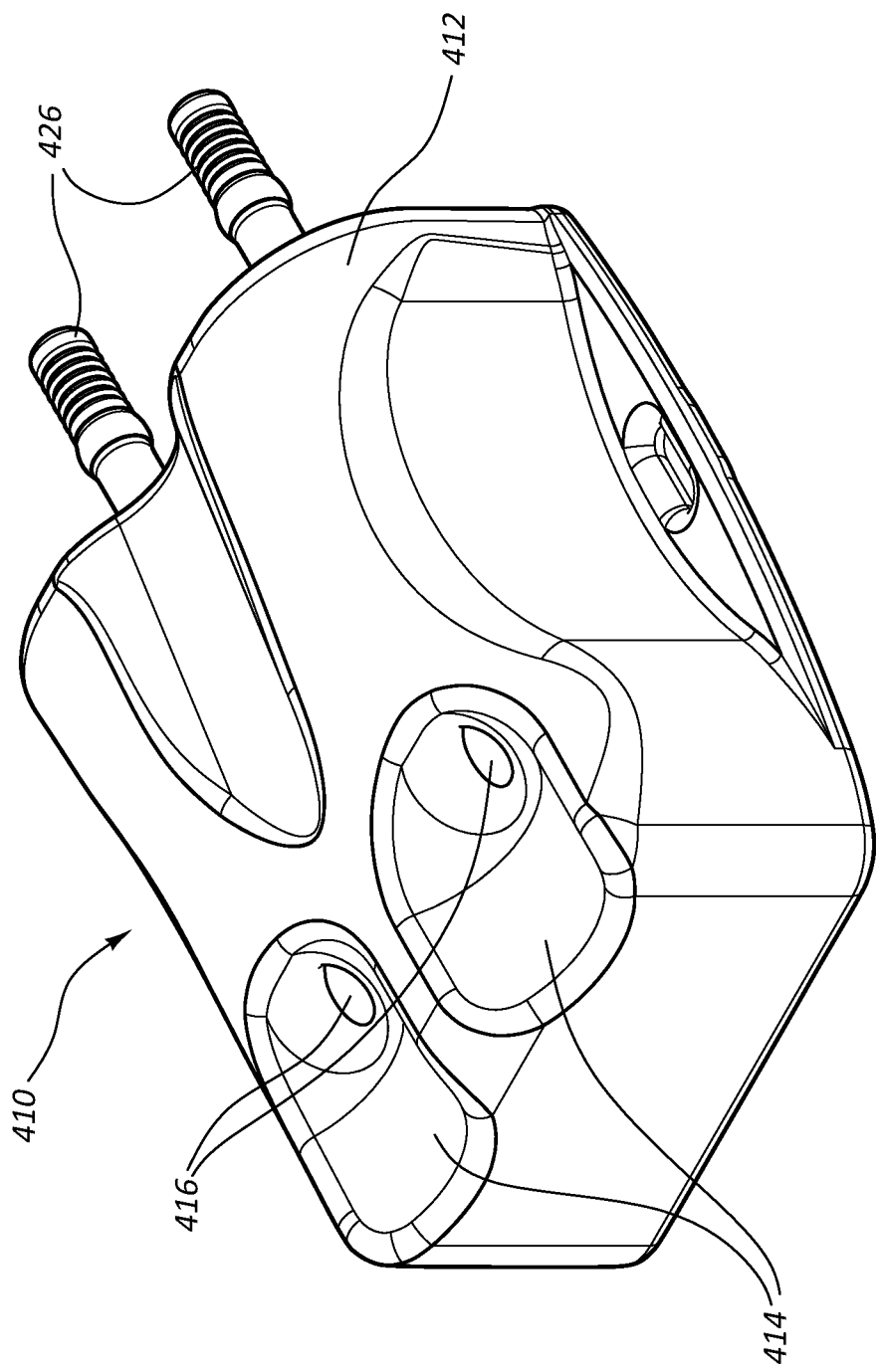
FIGS. 8A and 8B are various views of an access port according to one embodiment.
Figure 8B:
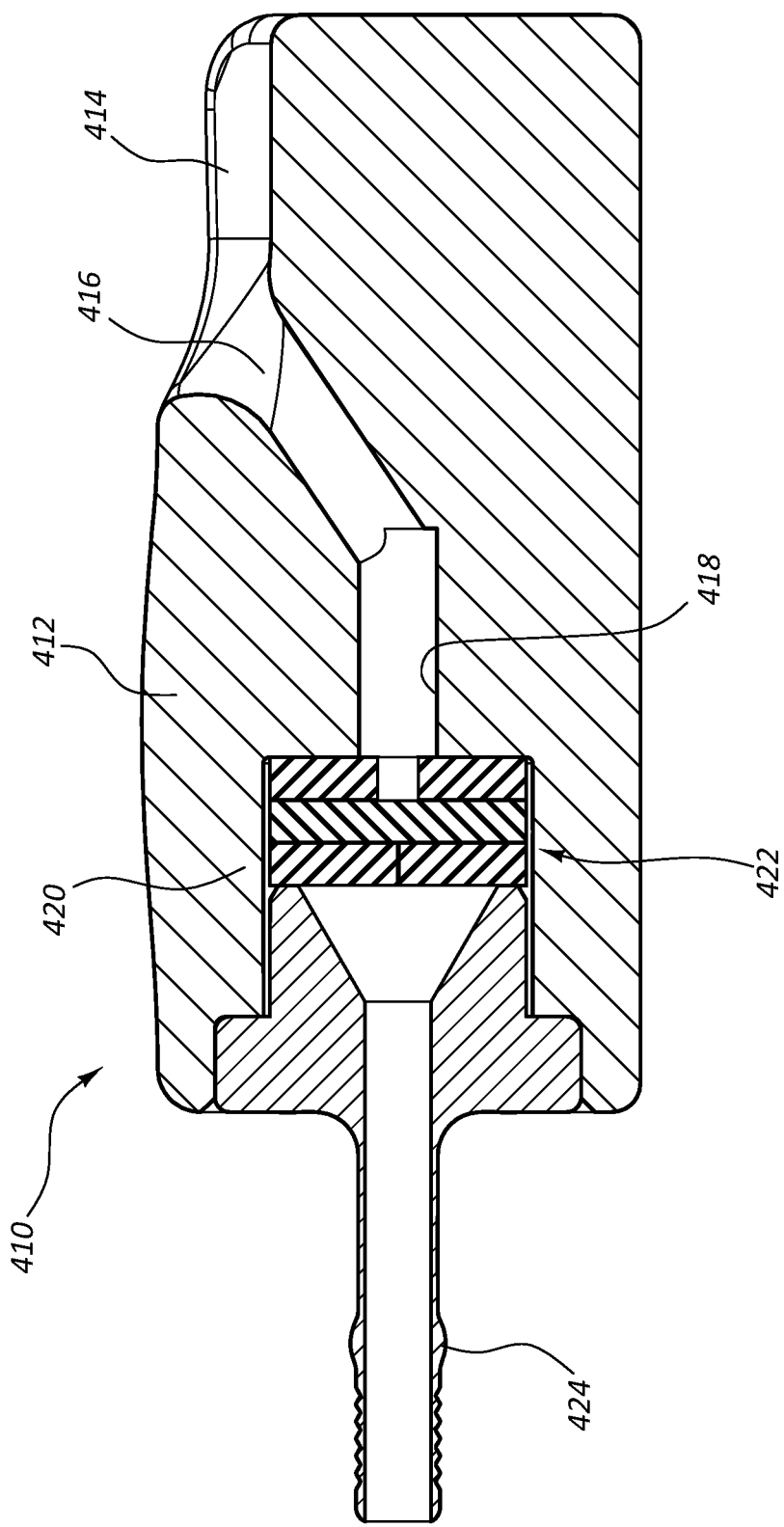

FIGS. 8A and 8B depict various details of a low-profile dual-body access port 410 according to one embodiment, wherein a port body 412 defines dual fluid paths. Each fluid path includes a receiving cup 414 defined by the body 412 and facing a substantially upward orientation from the perspective shown in FIGS. 8A and 8B. An inlet port 416 is included with each receiving cup 414 and defines the opening to a conduit 418. Each conduit 418 extends distally to a valve/seal assembly 422 disposed in a valve housing 420, which in the present embodiment, is defined by a portion of the body 412. The conduit 418 extends through the port 424. The body 412 can include any suitable material, including metal, thermoplastic, etc.

Reference is now made to FIGS. 9A-30, which depict various details of embodiments generally directed to vascular access devices, also referred to herein as access ports, for subcutaneous implantation within the body of a patient. The implanted access ports to be described are transcutaneously accessible by a catheter-bearing needle, such as a peripheral intravenous ("Hy") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

In accordance with one embodiment, the access port defines a relatively low profile so as to facilitate ease of placement within the subcutaneous tissue of the patient. Further, the access port is configured to provide a relatively large subcutaneous target to enable the PIV catheter or other suitable catheter-bearing needle to access the port without difficulty. In addition, the access port includes a valve/seal assembly to permit power injection of fluids through the access port. As before, possible applications for the access port described herein include administration of medicaments and other fluids to the patient, pheresis/apheresis, fluid aspiration, etc.

Figure 9A:
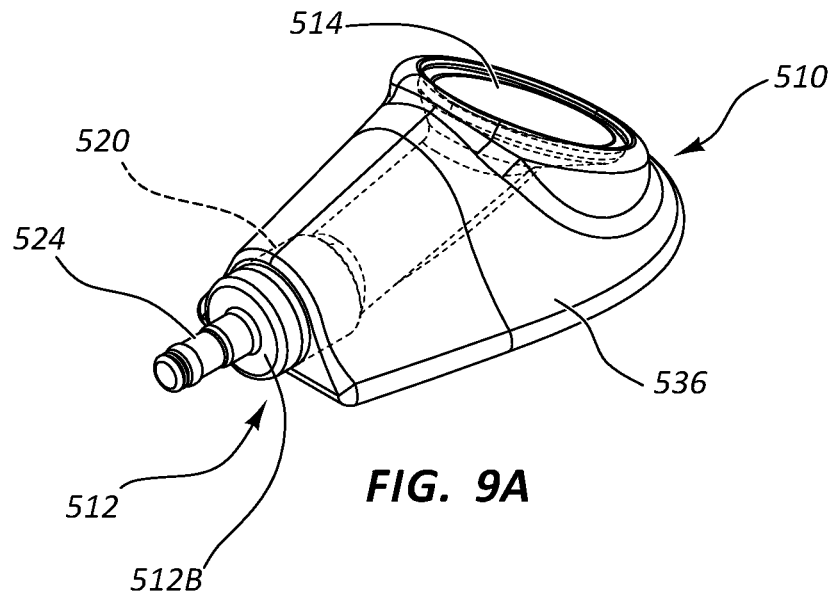
FIGS. 9A-9G depict various views of a low-profile vascular access device according to one embodiment.
Figure 9B:
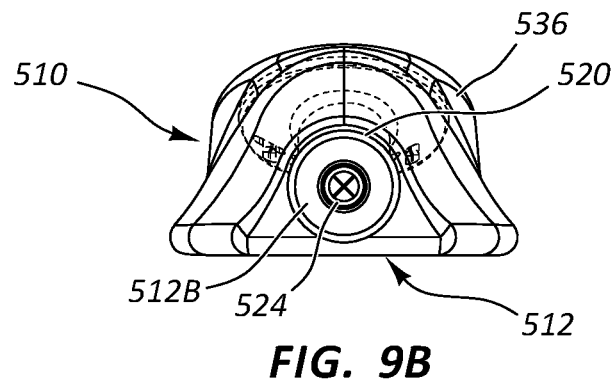
Figure 9C:
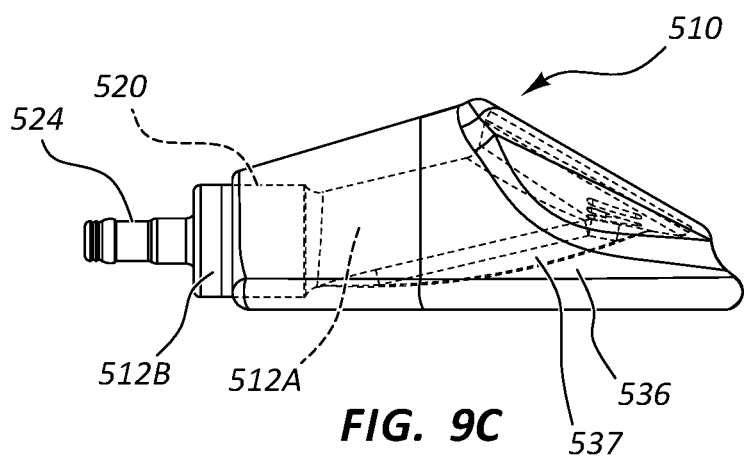
Figure 9D:
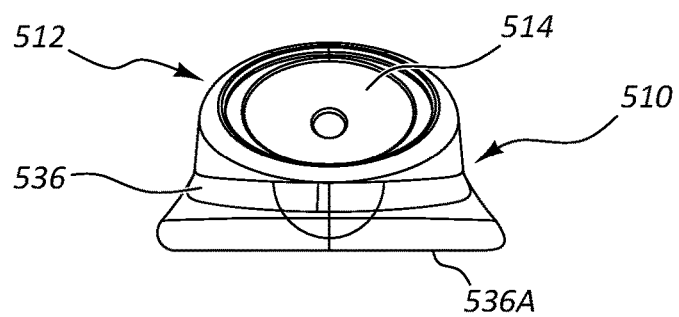
Figure 9E:
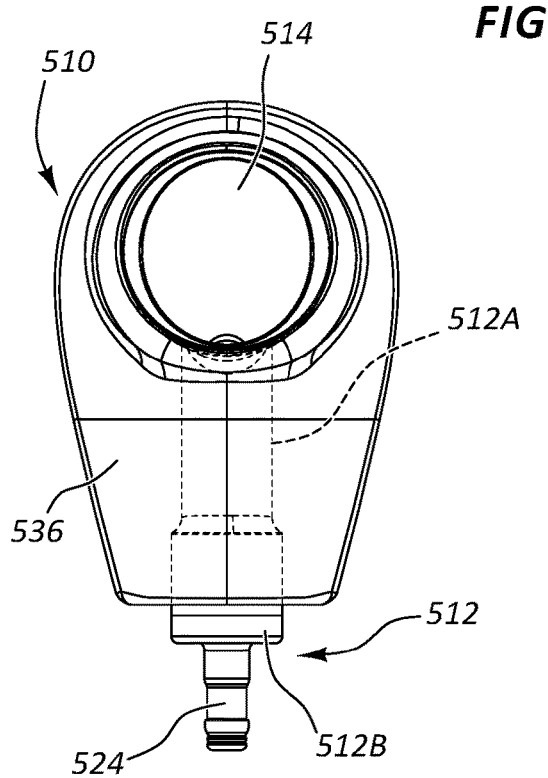

Reference is first made to FIGS. 9A-9G, which show various details of a vascular access device (also "access port" or "port"), generally designated at 510, in accordance with one embodiment. As shown, the port 510 includes a body 512 that is defined in the present embodiment by a first portion 512A and a second portion 512B (FIG. 9E). In the present embodiment the port body 512 includes a metal such as titanium, and as such, the second portion 512B is press fit into engagement with the first portion 512A to define the body, though it is appreciated that the port body can include a variety of other materials, including metals, thermoplastics, ceramics, etc.

The port body first portion 512A defines in the present embodiment a substantially funnel-shaped receiving cup 514 for receiving and directing a catheter-bearing needle (FIG. 14A) to operably connect with the port 510, as described further below. In particular, the substantially funnel shape of the receiving cup 514 is configured to direct the catheter-bearing needle (FIG. 14A) impinging thereon toward an inlet port 516 that serves as an opening for a conduit 518 defined by the port body 512. The open and shallow nature of the receiving cup 514, angled toward the skin surface of the patient enables the receiving cup to present a large, easily accessible target for the needle when introduced into the skin, as seen in FIGS. 14A-14D. FIGS. 9B and 9C further show that the port 510 defines a relatively low profile height, which enables relatively shorter needle lengths to be used for accessing the port after implantation. Note that palpation features can be included with the port body 512 to assist a clinician to locate and/or identify the port 510 via finger palpation after implantation under the skin of the patient, as with other embodiments herein. Further, in another embodiment a guide groove can be defined on the receiving cup 514 to be longitudinally aligned with the inlet port 516 of the conduit 518, similar to that shown in the access port 10 of FIG. 1A.

Figure 9F:
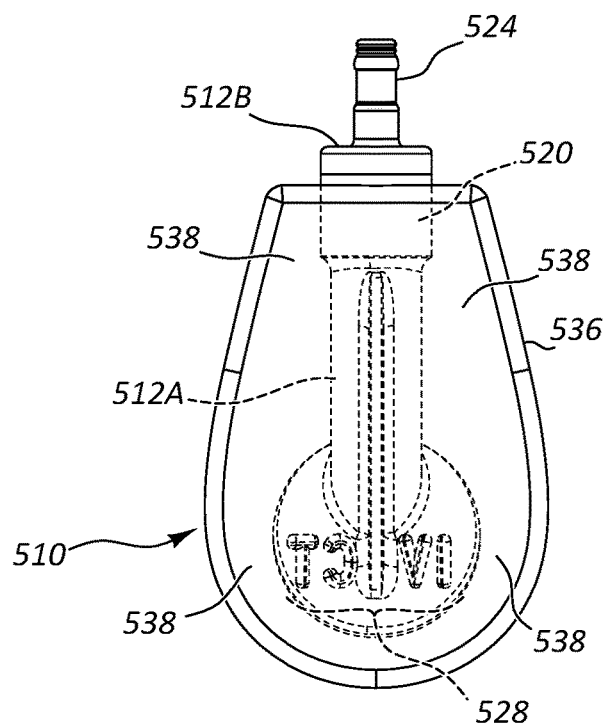
Figure 9G:
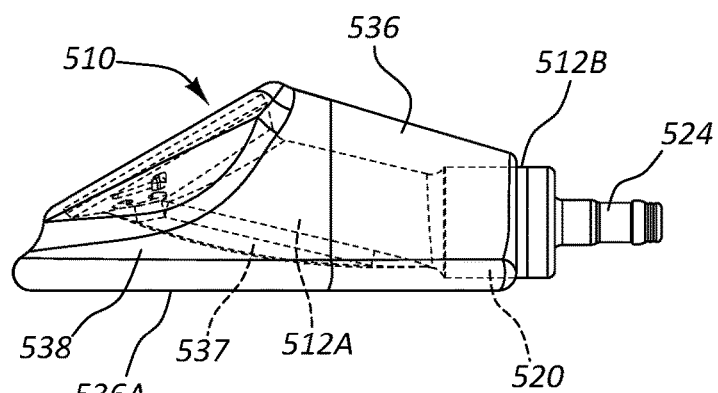
Figure 10:
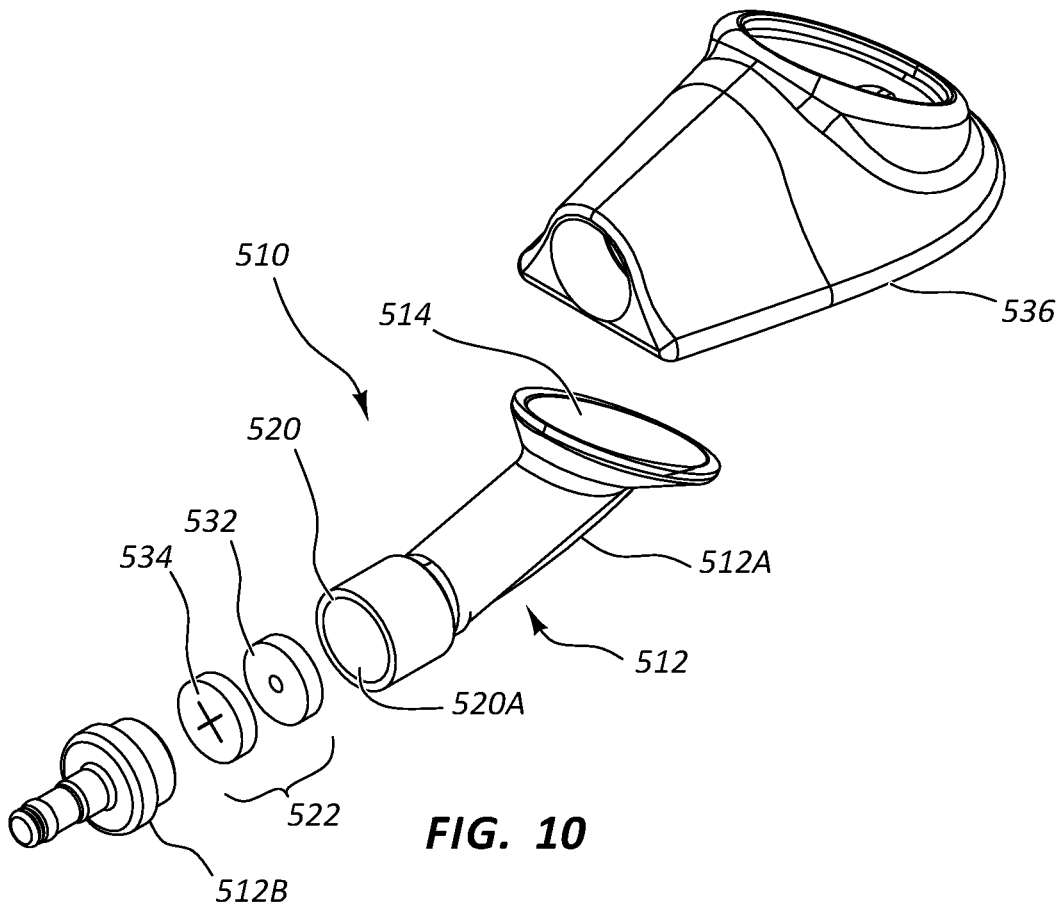
FIG. 10 is an exploded view of the access device of FIGS. 9A-9G.
Figure 11:
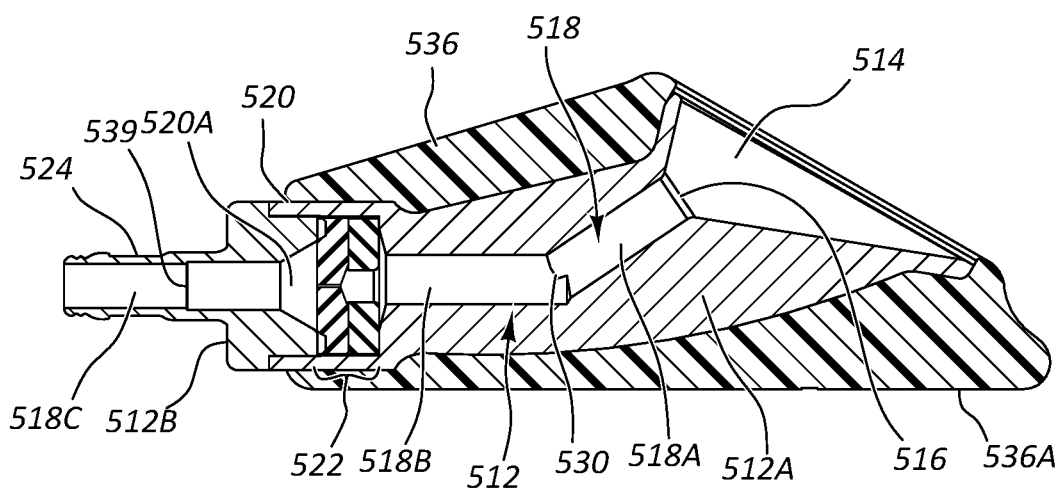
FIG. 11 is a cross-sectional view of the access device of FIGS. 9A-9G.
Figure 12A:
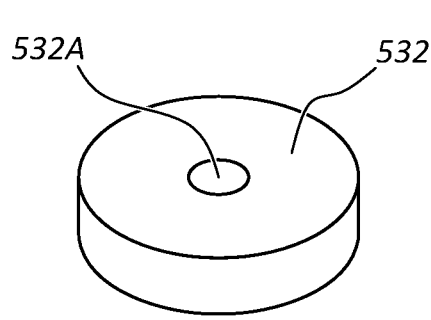
FIGS. 12A-12C depict various views of a seal according to one embodiment.
Figure 12B:
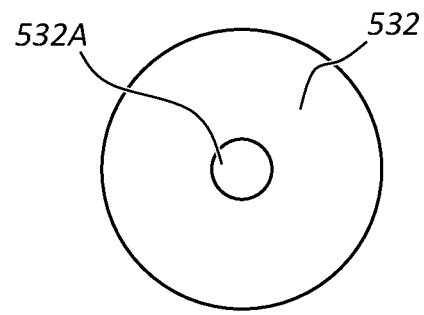
Figure 12C:
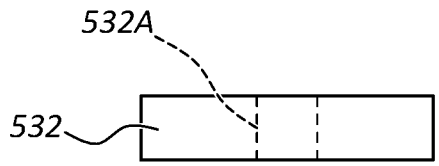

Together with FIGS. 9A-9G, reference is also made to FIGS. 10 and 11. As best seen in FIG. 11, the port body 512 further defines the conduit 518 as a pathway into which a transcutaneously inserted catheter can pass so as to place the catheter in fluid communication with the port 510 and the indwelling catheter attached to the stem 524 thereof. As shown, the conduit 518 is in fluid communication with the receiving cup 514 via the inlet port 516. A first conduit portion 518A of the conduit 518 distally extends from the inlet port 516 in an angled downward direction from the perspective shown in FIG. 11 to a bend 530, where a second conduit portion 518B of the conduit extends substantially horizontally (from the perspective shown in FIG. 11) at a predetermined angle with respect to the first conduit portion. Note that predetermined angle at the bend 530 in one embodiment is about 34 degrees, but can vary from this in other embodiments, including angles less or more than 34 degrees in one embodiment. The magnitude of the predetermined angle at the bend 530 depends in one embodiment on various factors, including the size of the catheter and/or needle to be inserted into the port conduit, the size of the conduit itself, etc.

The conduit 518 then extends to and through a cavity 520A defined by a valve housing 520 of the port body 12 where a third conduit portion 518C extends to a distal open end of the stem 524 of the port 510. In the present embodiment the conduit 518 is sized so as to enable the catheter 40 (FIG. 14A) to pass therethrough to a predetermined point, as will be seen.

Figure 13A:
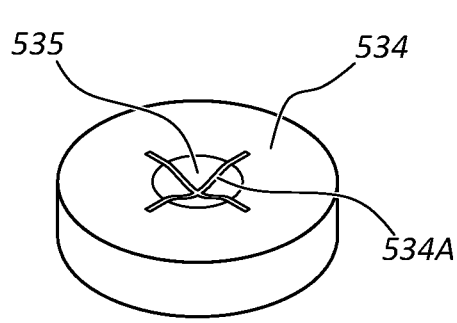
FIGS. 13A-13C depict various views of a valve according to one embodiment.
Figure 13B:
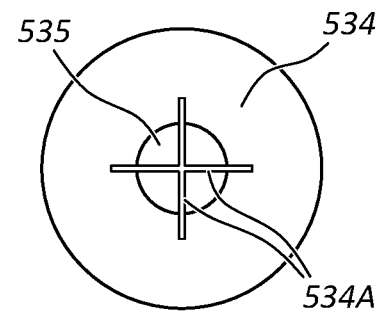
Figure 13C:
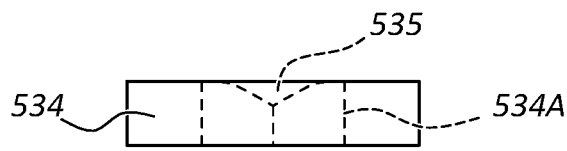

As mentioned, the valve housing 520, defined by portions of the first and second portions 512A, 512B of the body 512 defines a cavity 520A through which the conduit 518 passes and which houses a valve/seal assembly 522. The valve/seal assembly 522 includes a sealing element, or seal 532, which defines a central hole 532A (FIGS. 12A-12C) through which the catheter 40 (FIG. 14A) can pass, and a slit valve 534 including two intersecting slits 534A (FIGS. 13A-13C). The seal 532 and valve 534 are sandwiched together in one embodiment, with the seal 532 disposed proximal to the valve 534, and secured in place within the cavity 520A as shown in FIG. 11. The slits 534A of the slit valve 534 are orthogonally offset from one another by about 90 degrees in the present embodiment, though other relationships are possible. Note that the valve 534 includes a central depression 535 to ease the transition of passage of the catheter 40 from the seal 532 to the valve.

The seal 532 and valve 534 of the valve/seal assembly 522 cooperate to enable fluid-tight passage therethrough of the catheter 40 (FIG. 14A) while also preventing backflow of fluid through the valve/seal assembly. Indeed, in one embodiment the seals disclosed herein prevent fluid flow around the external portion of the catheter when the catheter is disposed through the seal 532, while the valve 534 is suitable for preventing fluid flow when no catheter passes through them. As such, when the catheter 40 is not inserted therethrough the valve/seal assembly 522 seals to prevent passage of air or fluid through the conduit 518. In the present embodiment, the seal 532 and valve 534 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 532 and valve 534 to enhance lubricity and extend component life. In another embodiment, the silicone oil is infused into the silicone.

The port 510 in the present embodiment includes an overmolded portion 536 that covers a majority portion of the port body 512. The overmolded portion 536 includes silicone, such as SILASTIC® Q7-4850 liquid silicone rubber or other suitably compliant material and surrounds the body 512 as shown so as to provide a relatively soft surface for the port 510 and reduce patient discomfort after port implantation within the patient body. The overmolded portion 536 includes in one embodiment predetermined suture locations 538, best seen in FIG. 9F, for suturing the port 510 to patient tissue, though sutures may be passed through other portions of the overmolded portion, if desired. The overmolded portion 536 further defines a relatively flat bottom surface 536A so as to provide a stable surface for the port 510 in its position within the tissue pocket after implantation into the patient body.

FIGS. 9C and 9G show that the first body portion 512A defines a securement ridge 537 that serves as an anchor to prevent relative movement between the overmolded portion 536 and the body 512. The securement ridge 537 can vary in shape, number, configuration, etc. Note that the overmolded portion 536 in one embodiment is molded in a molding process over the body 512. In another embodiment, the overmolded portion 536 is separately formed then adhesively attached to the body 512, such as via Med A adhesive. These and other configurations are therefore contemplated.

Figure 14A:
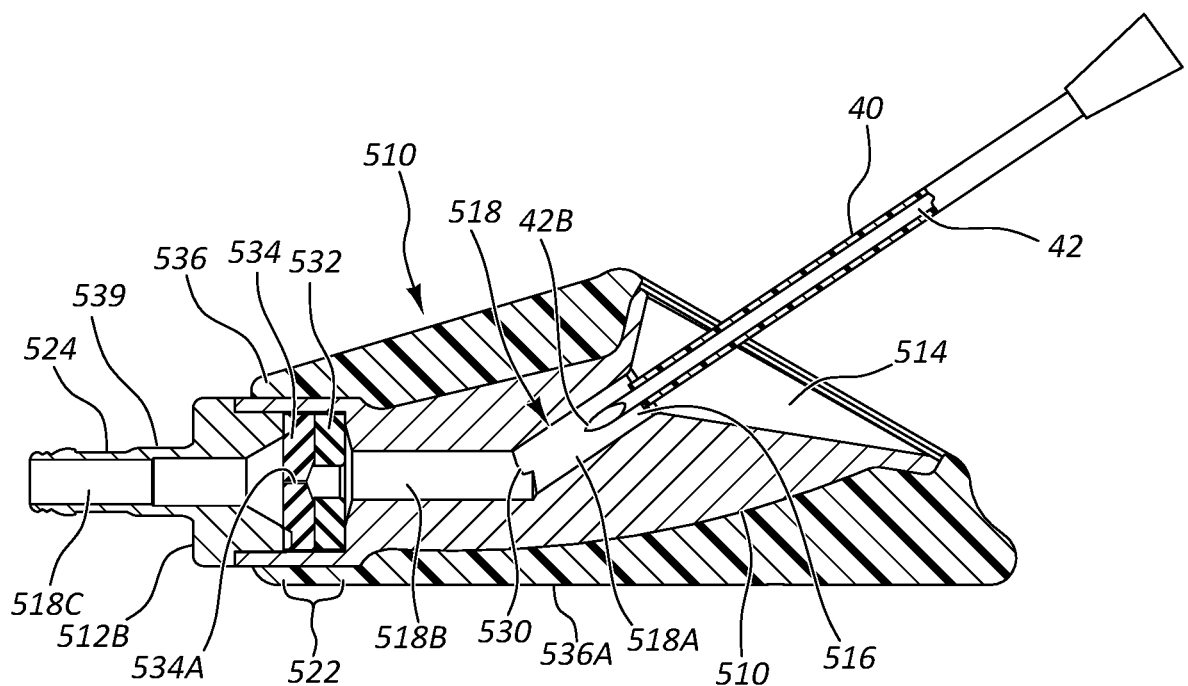
FIGS. 14A-14D depict various stages of insertion of a catheter into the access device of FIGS. 9A-9G.

FIGS. 14A-14D depict details regarding the insertion of the catheter 40 disposed on the needle 42 into the port 510 (already subcutaneously implanted into the body of the patient), according to one embodiment. After locating the port 510 (optionally via through-skin palpation of palpation features, such as a top portion of the overmolded portion 536 and/or the receiving cup 514), a clinician uses the catheter-bearing needle 42 to pierce a skin surface and insert the needle until a distal tip 42B thereof impinges on a portion of the receiving cup 514, as shown in FIG. 14A. Note that, because of the orientation of the receiving cup 514 is angled substantially toward the skin surface, the needle 42 can impinge on the receiving cup at an insertion angle that is relatively steep, which facilitates ease of needle insertion into the body. Indeed, in one embodiment a needle inserted substantially orthogonally through the skin of the patient can impinge the receiving cup of the access port. In another, embodiment, the insertion angle of the needle 42 can be relatively shallow, similar to current insertion angles for IV catheters.

Figure 14B:
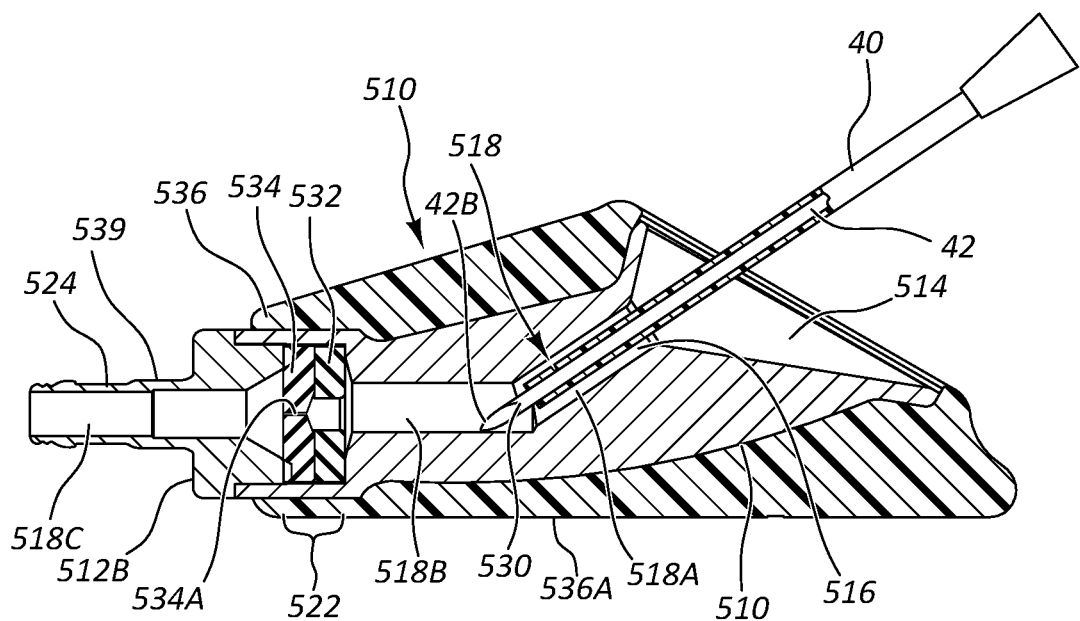
Figure 14C:
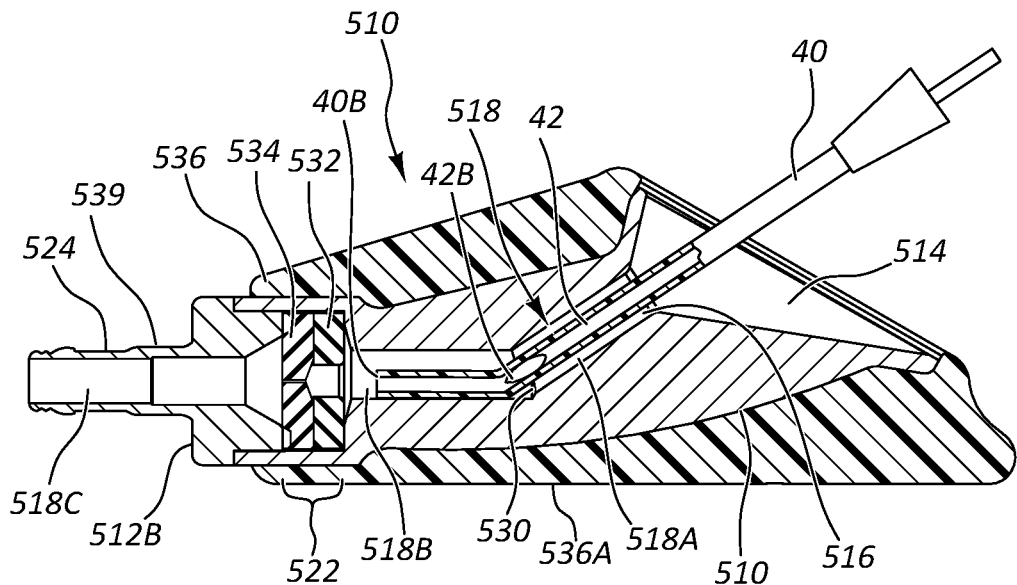

The needle 42 is manipulated by the clinician and guided by impingement on the receiving cup 514 until the needle distal tip 42B is guided to the inlet port 516. The needle 42 is then inserted through the inlet port 516 and into the first portion 518A of the conduit 518 until it is stopped by the bend 530, as seen in FIG. 14B. The needle 42 can then be proximally backed out a small distance, and the catheter 40 advanced over the needle such that the catheter bends and advances past the bend 530 into the second portion 518B of the conduit 518, as seen in FIG. 14C. Catheter advancement continues such that a distal end 40B of the catheter 40 advances into and past the hole 532A of the seal 532 and through both slits 534A of the slit valve 534 of the valve/seal assembly 522. Note that the length of the second conduit portion 518B is sufficient to enable the cross-sectional shape of the distal portion of the catheter 40 to return to a substantially round shape from the oval shape imposed thereon as a result of its passage through the conduit bend 530.

Figure 14D:
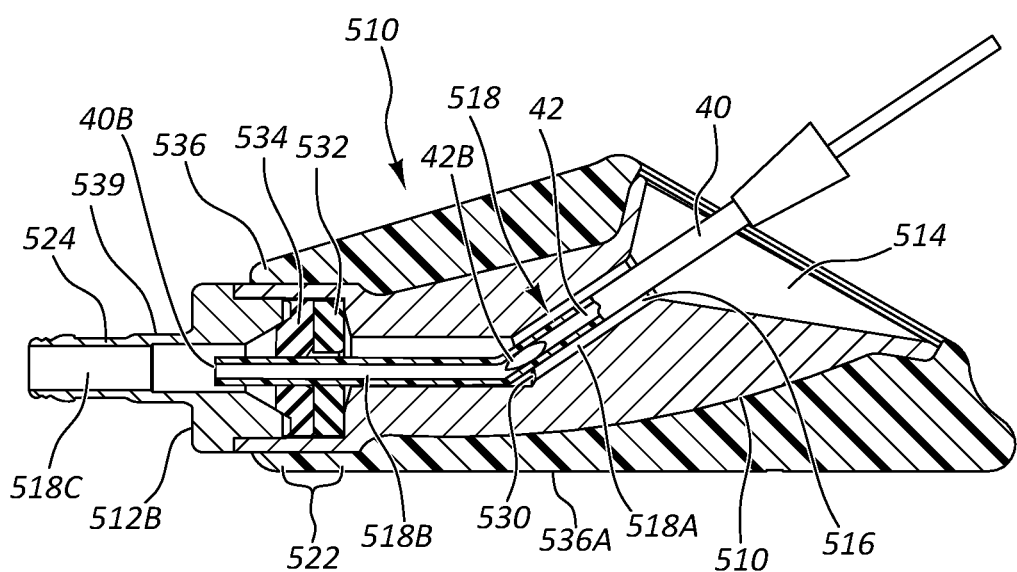

Once the distal end 40B of the catheter 40 has extended distally past the valve/seal assembly 522, further advancement is prevented by impingement of the catheter distal end against an annular stop surface 539 included in the third conduit portion 518C defined by the stem 524, as shown in FIG. 14D and in more detail in FIG. 11. In one embodiment, the stop surface 539 is defined as an annular shoulder and is sized so as to stop advancement of one size of catheter, such as 14 Gauge catheter, while allowing a 16 Gauge catheter to pass. In another embodiment, no stop surface is included in the conduit 518, thus enabling the catheter 40 to advance completely past the distal end of the stem 524, if desired. Note that the port conduit can be configured to accept one or more of a variety of catheter Gauge sizes, including 14 Gauge, 16 Gauge, 18 Gauge, etc.

Once the catheter 40 is positioned as shown in FIG. 14D, the needle 42 can be fully removed and fluid transfer through the catheter 40 and port 510 can commence, including infusion and/or aspiration through an indwelling catheter attached to the stem 524. (Note that the needle 42 can be removed at another stage of the catheter insertion procedure, in one embodiment.) Dressing of the catheter 40 can also occur as needed. Once fluid transfer is completed, the catheter 40 can be withdrawn proximally through the valve/seal assembly 522 and the conduit 518, then withdrawn through the surface of the skin and out of the patient.

FIG. 9F depicts that, in the present embodiment, the receiving cup 514 includes radiopaque indicia 528 to indicate a characteristic of the port 510. Here, the radiopaque indicia 528 includes an "IVCT" alphanumeric designation that is defined as a depression or recess into the titanium material forming the first body portion 512A so as to be visible after port implantation via x-ray imaging technology. The "IVCT" designation indicates that the port 510 is configured for power injection and is further configured to receive therein a peripheral IV catheter.

In another embodiment the radiopaque indicia 528 can be included by employing radiopaque material that can be formed as an insert that is insert-molded included in the port body, such as an initially flowable material that is injected into a cavity of the port body before hardening, etc. In embodiments where the port body is metallic, the radiopaque indicia can be formed by metal injection molding, machining, etching, engraving, or otherwise producing a relative thickness difference between the indicia and the surrounding port body material so as to produce an x-ray-discernible contrast that shows up in an x-ray image, similar to FIG. 1F.

In addition to above designation, other characteristics can be indicated by various other types of radiopaque indicia as appreciated by one skilled in the art.

As in other embodiments described herein, in one embodiment the perimeter of the receiving cup (or other suitable location) can include palpation features, such as three raised bumps in the overmolded portion 536 to assist in locating the position of the receiving cup 514 post-implantation when they are palpated by a clinician prior to needle insertion into the patient. Various other palpation features could be included with the port, in other embodiments, including disposal on the receiving cup itself, etc.

Figure 15A:
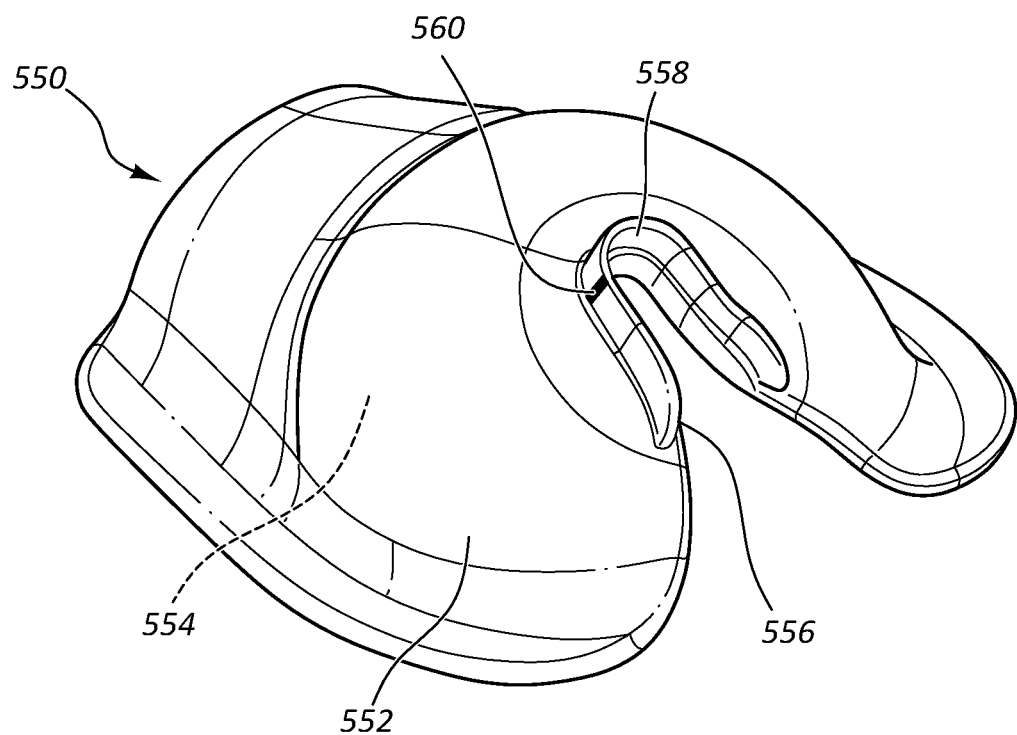
FIGS. 15A and 15B depict various views of a guide device for use with the access device of FIGS. 9A-9G according to one embodiment.
Figure 15B:
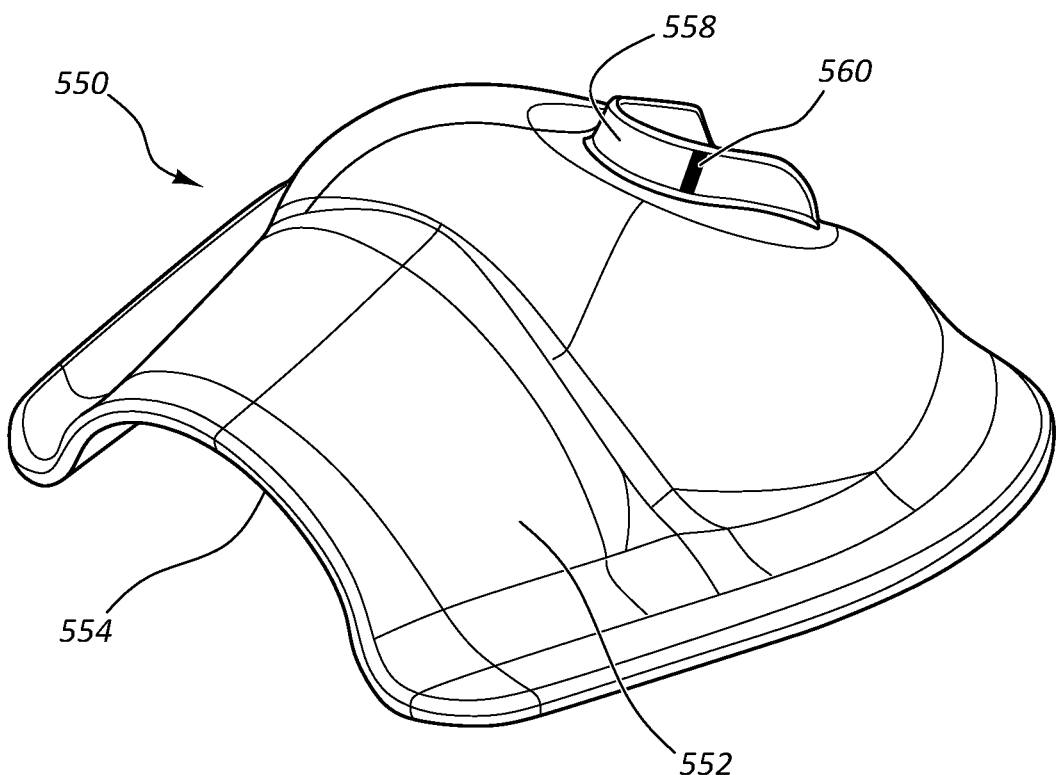

FIGS. 15A and 15B depict details of a guide device 550 that can be placed on the patient skin atop the implanted location of the port 510 shown in FIGS. 9A-9G to assist in guiding the needle 42 through the skin so as to impinge on the receiving cup 514, as desired. As shown, the guide device 550 includes a body 552 that defines a cavity 554 into which a portion of the subcutaneous implanted port 510 will reside when the guide device is pressed on the skin over the port. A notch 556 is included on the body 552, partially bordered by a ridge 558. The notch 556 enables the needle 42 to be passed therethrough so as to be inserted through the skin and into port 510. A marker line 560 is included on the ridge 548 to assist the clinician in placing the needle 42 at the proper orientation and location for impingement on the receiving cup 514, as desired. Note that the shape, size, and other configuration of the guide device can vary from what is shown and described herein.

Figure 25A:
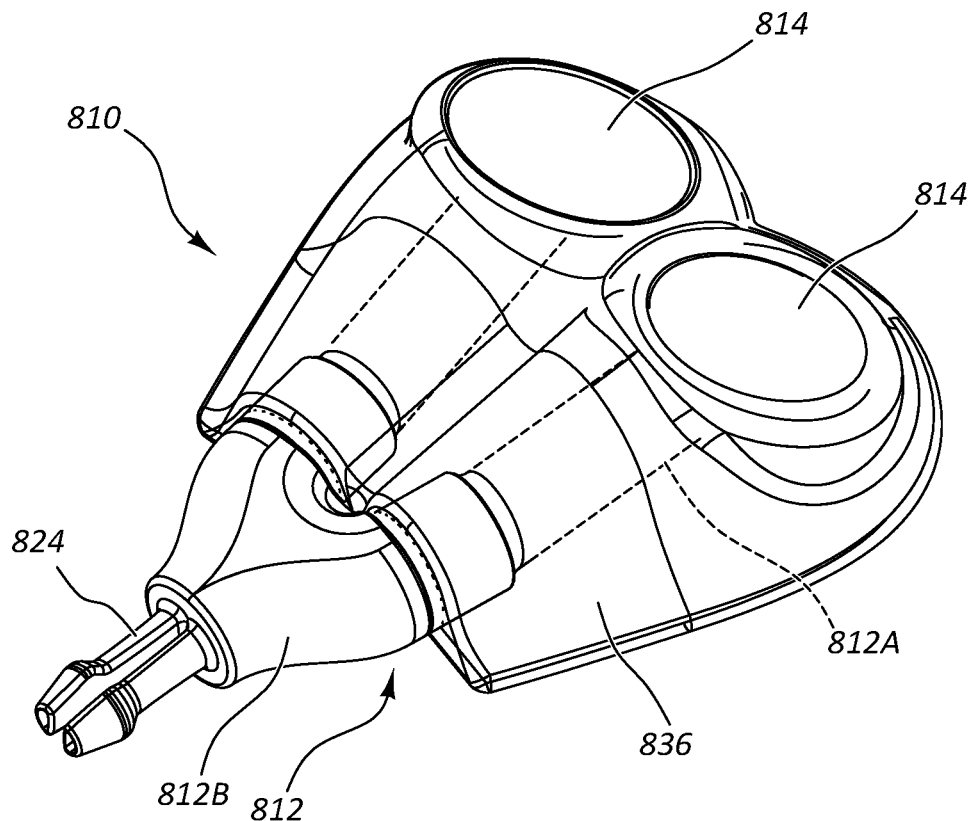
FIGS. 25A-25E depict various views of a low-profile vascular access device according to one embodiment.
Figure 25B:
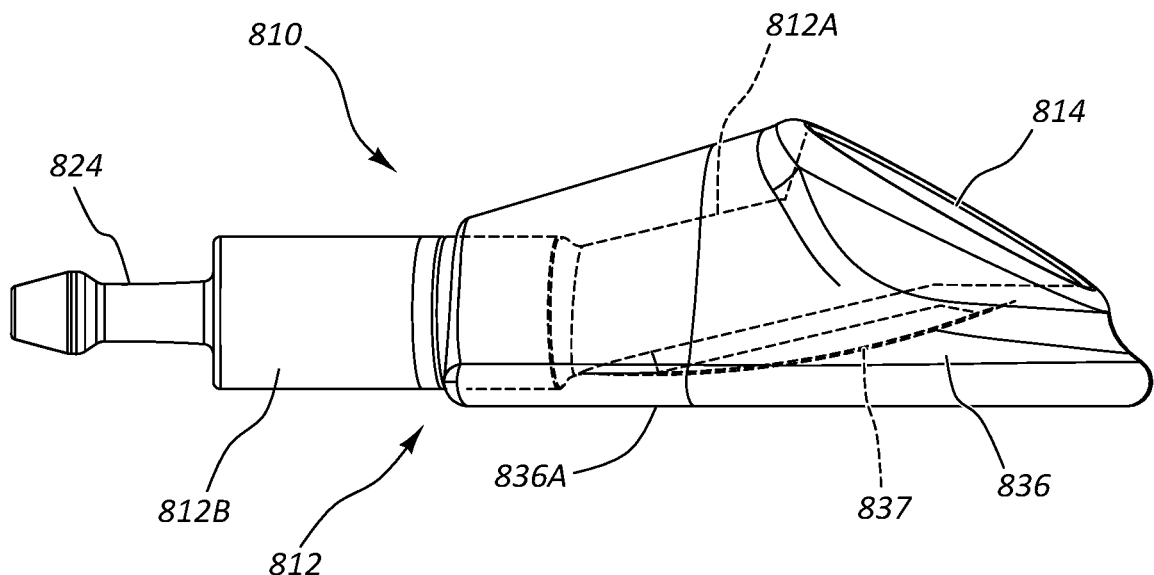
Figure 25C:
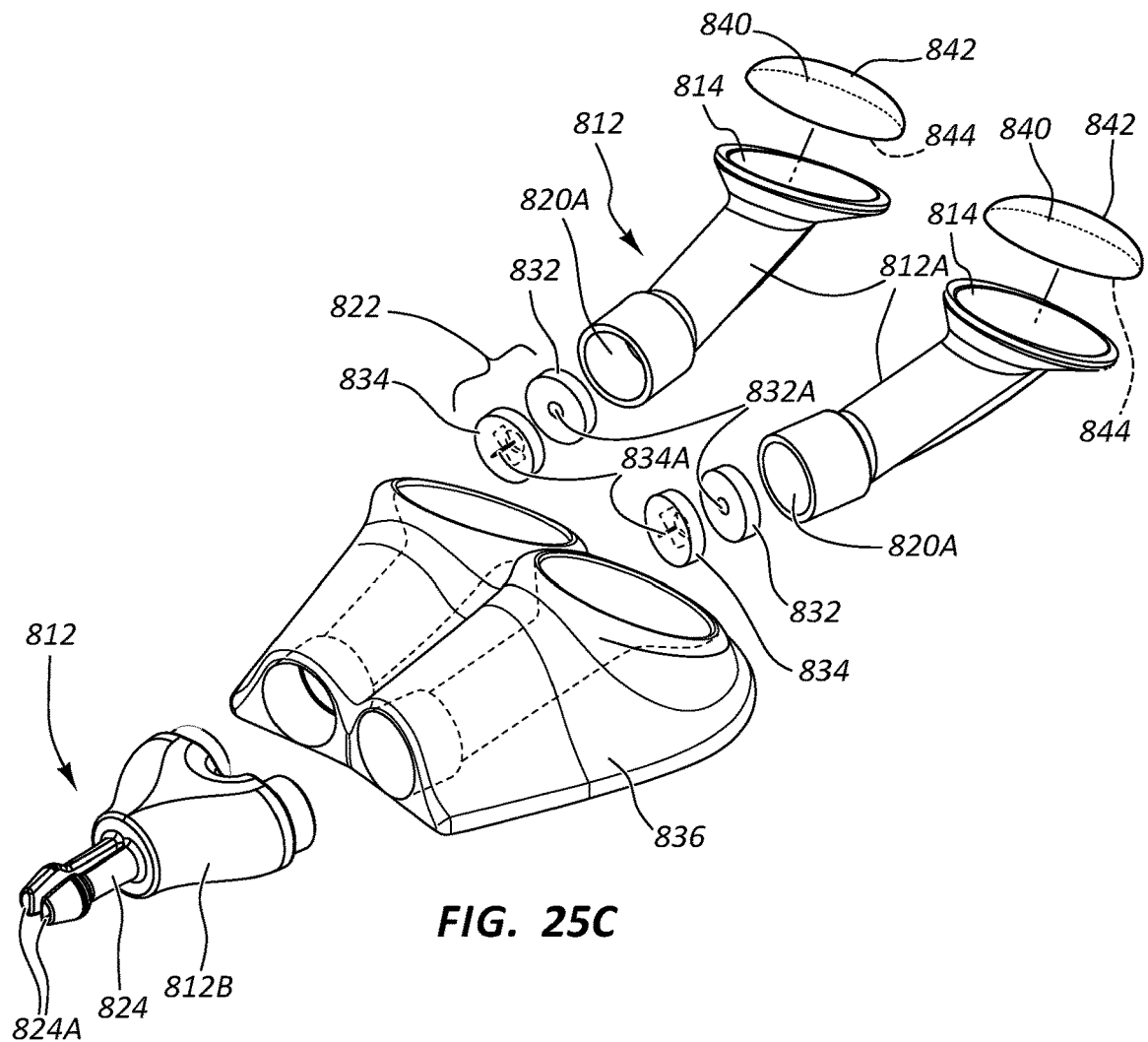

Reference is now made to FIGS. 25A-25E, which show various details of a dual-lumen vascular access device, generally designated at 810, in accordance with one embodiment. As shown, the port 810 includes a body 812 that is defined in the present embodiment by two similarly shaped portions: a single first portion 812A and a single second portion 812B (FIG. 25C). In the present embodiment the port body first and second portions 812A, 812B include a metal such as titanium, and as such, the second portion is press fit into engagement with the first portion to define the body, though it is appreciated that the port body can include a variety of other materials, including metals, thermoplastics, ceramics, etc., and can include other joining methods including adhesive, ultrasonic or other welding, interference fit, etc.

Both port body first portions 812A define in the present embodiment a substantially funnel-shaped receiving cup 814 for receiving and directing the catheter-bearing needle 42 (FIG. 14A) to operably connect with the port 810 in a manner similar to that already described above. In particular, the substantially funnel shape of each receiving cup 814 is configured to direct the catheter-bearing needle 42 impinging thereon toward an inlet port 816 that serves as an opening for a respective conduit 818 defined by the port body 812. The open and shallow nature of each receiving cup 814, angled toward the skin surface of the patient enables the receiving cup to present a large, easily accessible target for the needle when introduced into the skin and directed toward the subcutaneously implanted access port 810. FIG. 25B further shows that the access port 810 defines a relatively low profile height, which enables relatively shorter needle lengths to be used for accessing the subcutaneous access port after implantation.

Note that, as already mentioned, palpation features can be included with the port body 812 in one embodiment to assist a clinician to locate and/or identify the port 810 via finger palpation after implantation under the skin of the patient. Note that a variety of sizes, configurations, numbers, etc., of palpation features can be included on the port. In another embodiment, a guide groove can be defined on the receiving cup 814 to be longitudinally aligned with the inlet port 816 of the conduit 818, as discussed in connection with the embodiment of FIGS. 1A-2. The guide groove can be defined as a depression with respect to adjacent portions of the surface of the receiving cup 814 and extend distally along the receiving cup surface from a proximal portion of the receiving cup so as to provide a guide path to guide the distal tip of the catheter-bearing needle toward the inlet port 816 once impingement of the needle into the guide groove is made. This in turn reduces the chance the needle will slide across and off the receiving cup 814 during insertion. Note that these and other similar features, though differing in shape and configuration, can also be included on the other ports disclosed herein.

In an embodiment, the receiving cup 814 is covered by a septum 840. The septum 840 can be a self-sealing, needle penetrable septum, capable of receiving multiple needle piercings to allow access to the receiving cup 814 there below. Accordingly, the septum 840 can be made of a suitable needle-penetrable material, such as silicone, or the like. The septum 840 includes an outer surface 842 and an inner surface 844 opposite that of the outer surface 842 and substantially facing receiving cup 814. Either of the outer or inner surfaces 842, 844 can be flat or slightly convex. In an embodiment, the inner surface 844 is substantially flat while the outer surface 842 is convex to align with the rounded outer surface of the overmolded portion 836 and provide a continuous outer profile to the port 810. Advantageously, the septum 840 completes a convexly rounded outer profile to the port 810 that allows for a smooth implantation of the device within a tissue pocket and reduces patient discomfort after port implantation within the patient body. Further the septum 840 can prevent tissue ingrowth into the receiving cup 814, and associated conduits 818, that would otherwise obstruct the path of the needle entering the device. Accordingly, the septum 840 prevents additional surgeries required to remove such obstructions or to replace the device 810 prematurely. It will be appreciated that septum 840 can also be applied to any embodiment disclosed herein.

Figure 25D:
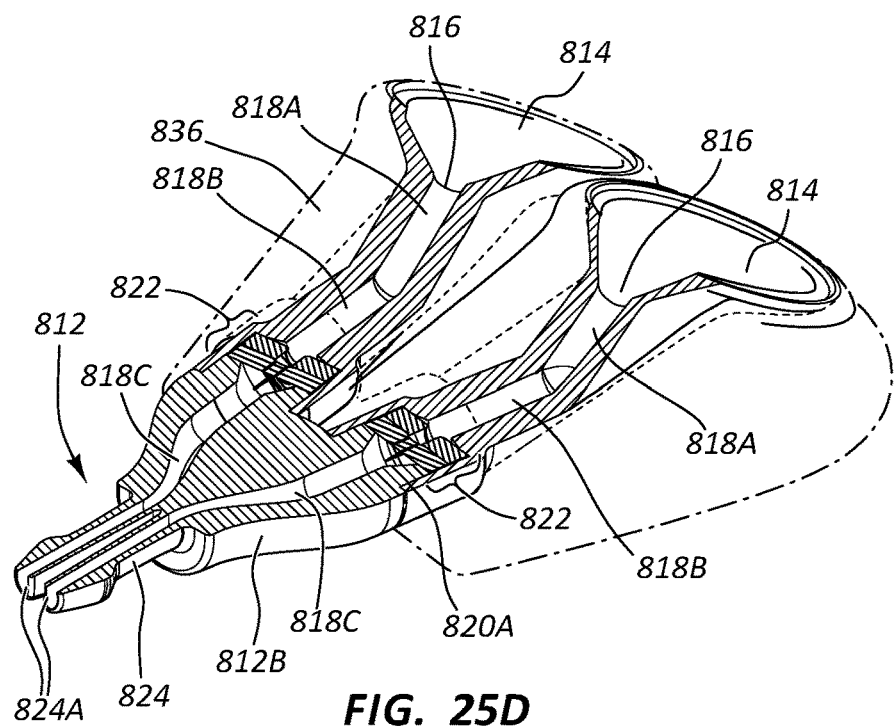

As best seen in FIG. 25D, the port body 812 further defines the two conduits 818, each conduit serving as a pathway into which a transcutaneously inserted catheter can be partially inserted so as to place the catheter in fluid communication both with the port 810 and an indwelling dual-lumen catheter operably attached to two fluid outlets 824A of a stem 824 of the port. As shown, the conduit 818 of each port body first portion 812A is in fluid communication with its respective receiving cup 814 via the inlet port 816. A first conduit portion 818A of the conduit 818 distally extends from the inlet port 816 in an angled downward direction from the perspective shown in FIG. 25D to a conduit bend 830, where a second conduit portion 818B of the conduit extends at a predetermined angle with respect to the first conduit portion. Note that predetermined angle at the bend 830 in one embodiment is about 34 degrees, but can vary from this in other embodiments, including angles smaller or greater than 34 degrees in one embodiment. The magnitude of the predetermined angle at the bend 830 depends in one embodiment on various factors, including the size of the catheter and/or needle to be inserted into the port conduit, the size of the conduit itself, etc. Note also that the conduit bend 830 serves as a needle-stop feature, preventing the needle 42 from advancing along the conduit 818 past the bend 830.

The second conduit portion 818B of each port body first portion 812A distally extends to a cavity 820A defined by the press-fit junction of the port body first portion and the second portion 812B, as seen in FIG. 25D. Two third conduit portions 818C are defined by the second portion 812B of the port body 812 and extend from each of the cavities 820A in a partially arcuate fluid path to the distally-disposed fluid outlets 824A of the stem 824. In the present embodiment the conduit 818 is sized so as to enable the catheter 40 (FIG. 14A) to pass therethrough and past the cavity 820A.

As mentioned, the cavities 820A, each defined by the junction of the respective first portion 812A and the second portion 812B of the port body 812, each define a space through which the conduit 818 passes and in which is housed a valve/seal assembly 822. In the present embodiment and as best seen in FIGS. 25C and 25D, the valve/seal assembly 822 includes a sealing element, or seal 832, which defines a central hole 832A through which the catheter 40 (FIGS. 14A, 14D) can pass, and a slit valve 834 including two orthogonally intersecting slits 834A through which the catheter also passes. The seal 832 and slit valve 834 are sandwiched together in one embodiment, with the seal disposed proximal to the slit valve, and secured in place within the correspondingly sized cavity 820A as shown in FIG. 25D.

As mentioned, the slits 834A of the slit valve 834 are orthogonally offset from one another by about 90 degrees in the present embodiment, though other relationships are possible, including the use of two single-slit valves sandwiched together with one another. Note that in the present embodiment the slit valve 834 includes a central depression (as in previous embodiments, such as is shown in FIG. 13A, for instance) to ease the transition of passage of the catheter 40 from the seal 832 to the valve. More than one seal and/or slit valve may be employed in the valve/seal assembly in other embodiments.

As with previous embodiments, the seal 832 and slit valve 834 of the valve/seal assembly 822 cooperate to enable fluid-tight passage therethrough of the catheter 40 (see, e.g., FIG. 14A) while also preventing backflow of fluid through the valve/seal assembly. Indeed, in one embodiment the seals disclosed herein prevent fluid flow around the external portion of the catheter when the catheter is disposed through the seal 832, while the valve 834 is suitable for preventing fluid flow when no catheter passes through them. As such, when the catheter 40 is not inserted therethrough the valve/seal assembly 822 seals to prevent passage of air or fluid through the conduit 818. In the present embodiment, the seal 832 and valve 834 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 832 and valve 834 to enhance lubricity and extend component life. In another embodiment, the silicone oil is infused into the silicone.

The port 810 in the present embodiment includes an overmolded portion 836 that covers a portion of the port body 812, including a majority portion of each of the two first portions 818A. The overmolded portion 836 includes silicone, such as SILASTIC® Q7-4850 liquid silicone rubber or other suitably compliant material and surrounds the portions of the body 812 as shown in FIGS. 25A and 25B so as to provide a relatively soft surface for the port 810 and reduce patient discomfort after port implantation within the patient body. The overmolded portion 836 further enables a clinician to suture through one or more of various portions of the overmolded portion to enable the port 810 to be secured within a subcutaneous patient tissue pocket. The overmolded portion 836 further defines a relatively flat bottom surface 836A so as to provide a stable surface for the port 810 in its position within the tissue pocket after implantation into the patient body.

FIG. 25B shows that the first body portions 812A each define a securement ridge 837 that serves as an anchor to prevent relative movement between the overmolded portion 836 and the body 812. The securement ridge 837 can vary in shape, number, configuration, etc. Note that the overmolded portion 836 in one embodiment is molded in a molding process over the body 812. In another embodiment, the overmolded portion 836 is separately formed then adhesively attached to the body 812, such as via Med A adhesive. These and other configurations are therefore contemplated.

Figure 25E:
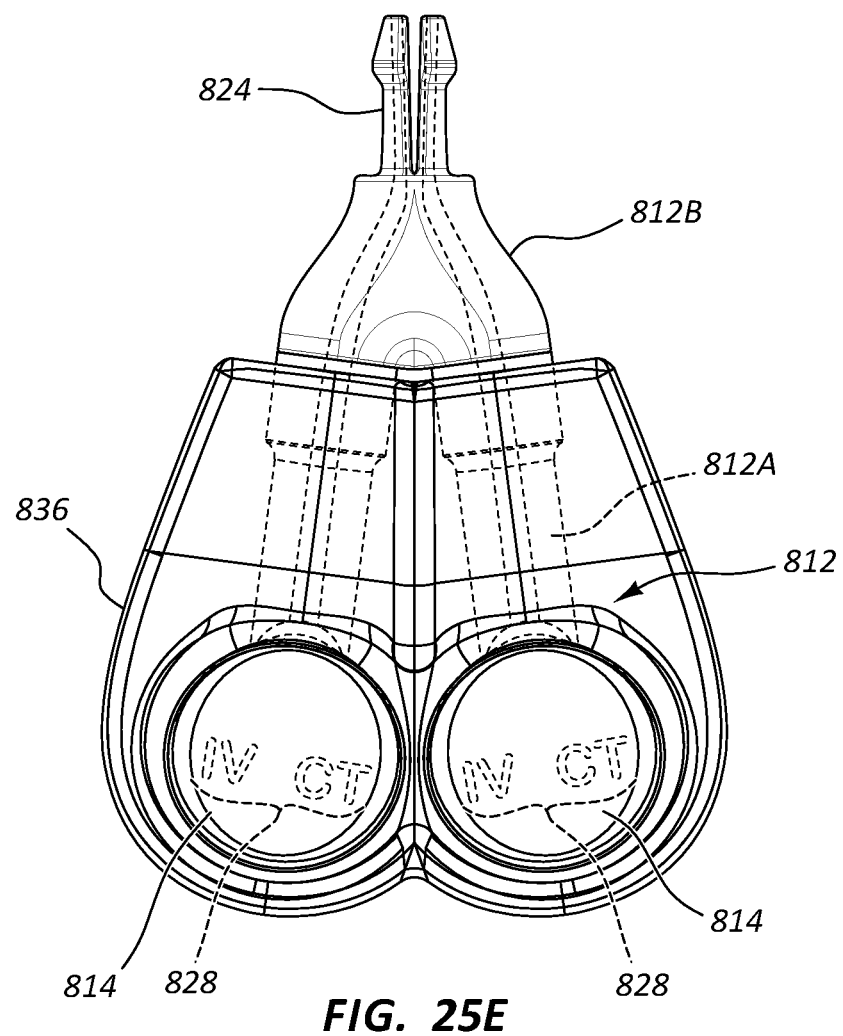
Figure 26A:
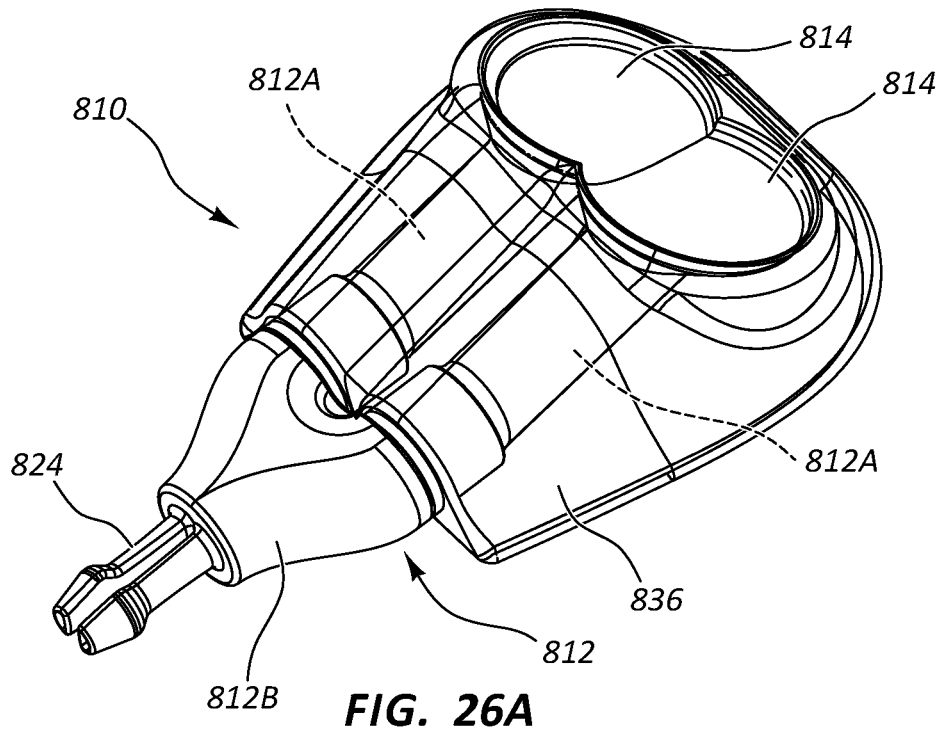
FIGS. 26A-26D depict various views of a low-profile vascular access device according to one embodiment.
Figure 26B:
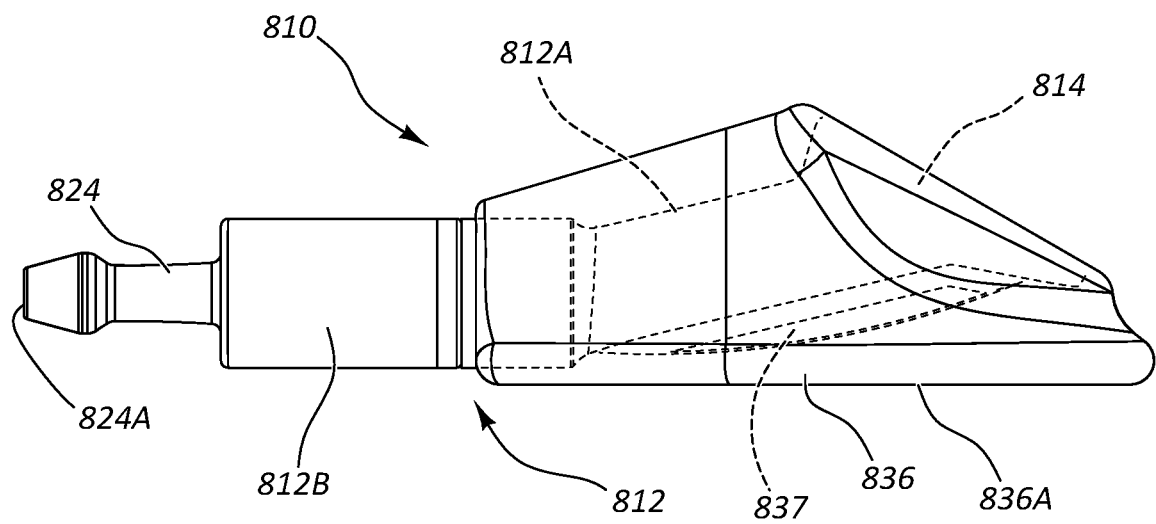
Figure 26C:
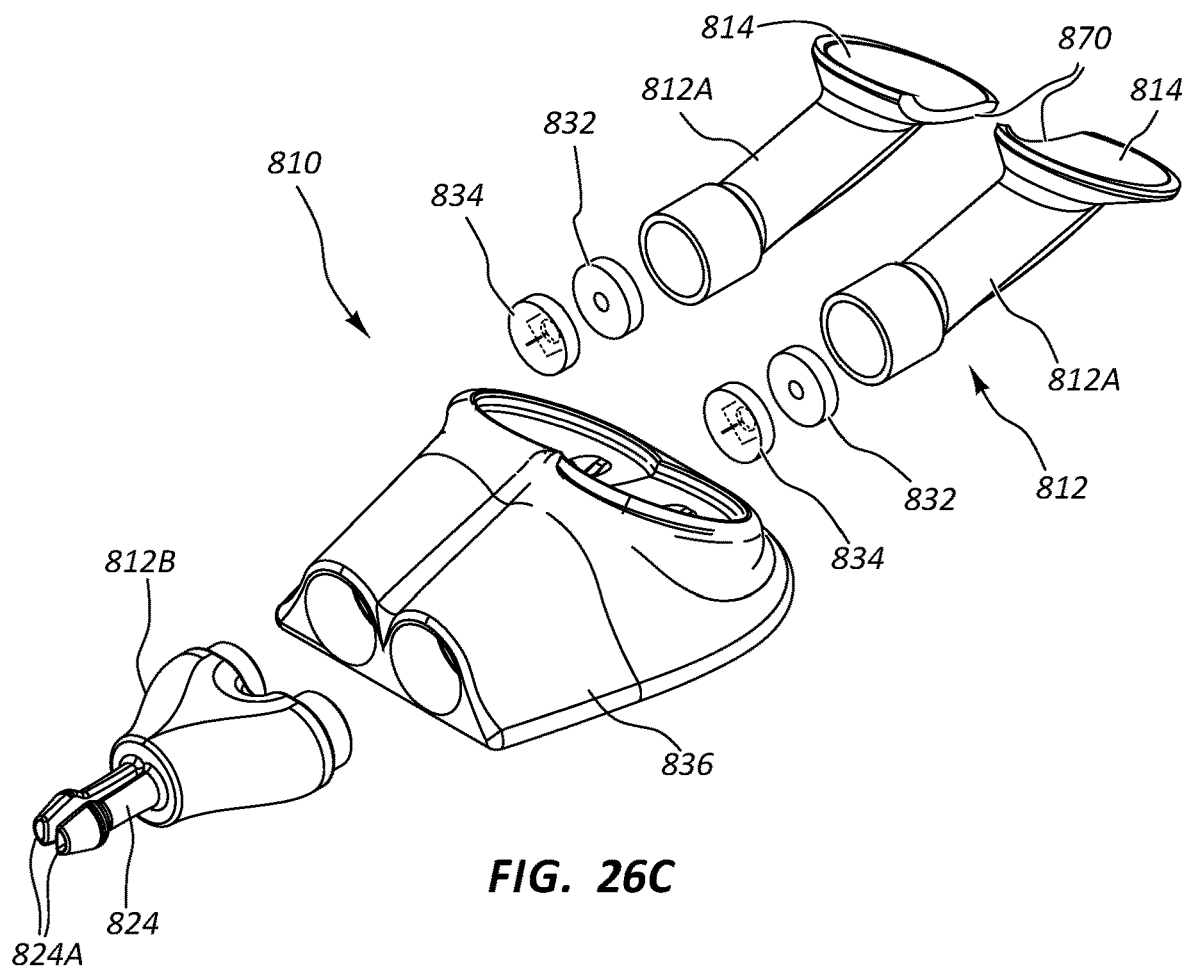
Figure 26D:
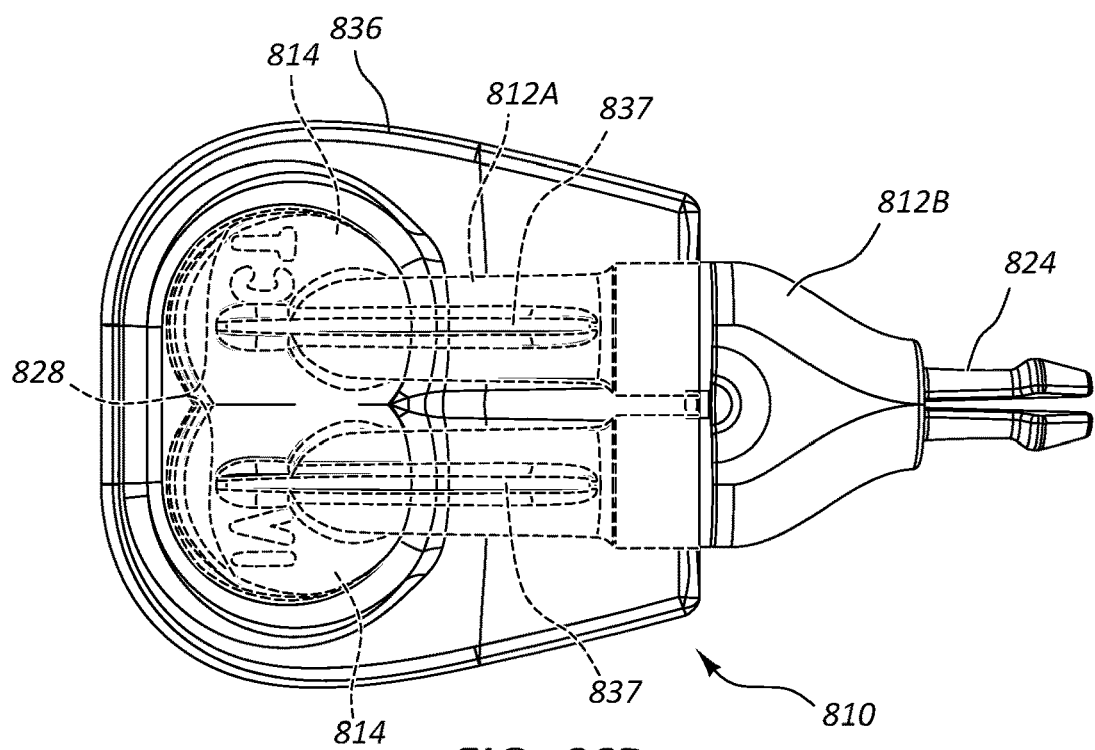

FIG. 25E shows that underside surfaces of the receiving cups 814 include a radiopaque indicia 828 configured to enable the port 810 to be radiographically identified after implantation into the patient body. In the present embodiment each of the indicia 828 includes the letters "IV" and "CT" to indicate suitability of the port 810 to receive peripheral IV catheters and that the port is capable of power injection of fluids therethrough. Of course, a variety of other indicia, including letters, numbers, symbols, etc., may be used.

FIGS. 26A-26D depict various details of the port 810 according to another embodiment, wherein the port body 812 defines a relatively slimmer profile than the embodiment shown in FIGS. 25A-25E, made possible by defining a cutout 870 on both receiving cups 814 of each first portion 812A of the port body 812. This enables the receiving cups 814 to reside relatively close to one another. The receiving cups 814 can be joined to one another along the cutouts 870 via welding, adhesive, forming the welding cups together as a single component, etc.

Figure 31:
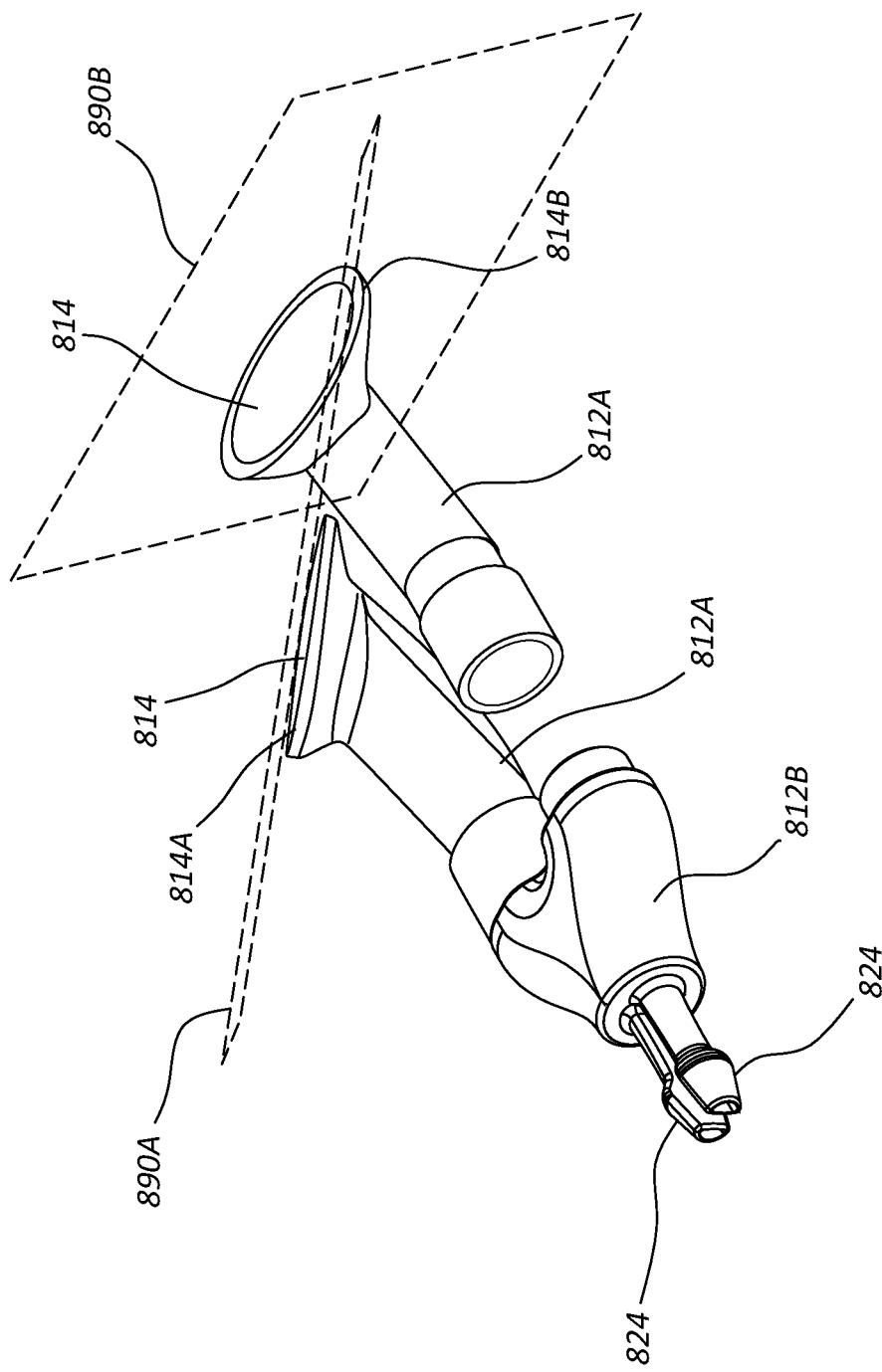
FIG. 31 is a perspective view of a portion of a vascular access device according to one embodiment.

In one embodiment, it is appreciated that the receiving cups 814 can be oriented in other configurations. FIG. 31 gives an example of this, wherein a partially exploded view of the port 810 is shown without the overmolded portion 836 present, and thus including the two first portions 812A and the second portion 812B. As shown, the receiving cups 814 are angled with respect to one another such that a perimeter 814A of a corresponding one of the receiving cups lies in an imaginary plane 890A that is non-parallel to another plane 890B in which a perimeter 814B of the other receiving cup lies. This is in contrast to another embodiment, such as that shown in FIG. 25A, wherein the receiving cups 814 substantially lie in a single imaginary plane. The configuration of FIG. 31 results in the receiving cups 814 being angled away from one another, as shown in FIG. 31 (note that the first body portion 812A shown disconnected (for clarity) from the second body portion 812B is to be connected to the second body portion in substantially the same orientation as shown in FIG. 31). This, in turn, desirably results in a slightly lower height profile for the access port 810, and can also result in the needle 42 inserted therein residing relatively closer to the patient skin, in one embodiment. Note that the receiving cups can be angled in various different configurations in addition to what is shown and described herein.

Reference is now made to FIGS. 16A-21B, which depict details of a dual-lumen vascular access device, generally designated at 610, in accordance with one embodiment. As shown, the port 610 includes a body 612 that is defined in the present embodiment by a first portion 612A and a relatively smaller second portion 612B that is partially received within the first portion. In the present embodiment the port body first and second portions 612A, 612B include a metal such as titanium, and as such, the second portion is press fit into engagement with the first portion to define the body, though it is appreciated that the port body can include a variety of other materials, including metals, thermoplastics, ceramics, etc., and can include other joining methods including adhesive, ultrasonic or other welding, interference fit, etc.

The port body first portion 612A defines in the present embodiment two substantially funnel-shaped receiving cups 614 for receiving and directing the catheter-bearing needle 42 (FIG. 14A) to operably connect with the port 610 in a manner similar to that already described above. The receiving cups 614 in the present embodiment are disposed so as to be substantially aligned along a longitudinal axis of the port 610, though other positional arrangements for the receiving cups are possible, including side-by-side, spaced-apart, staggered, etc.

Figure 16A:
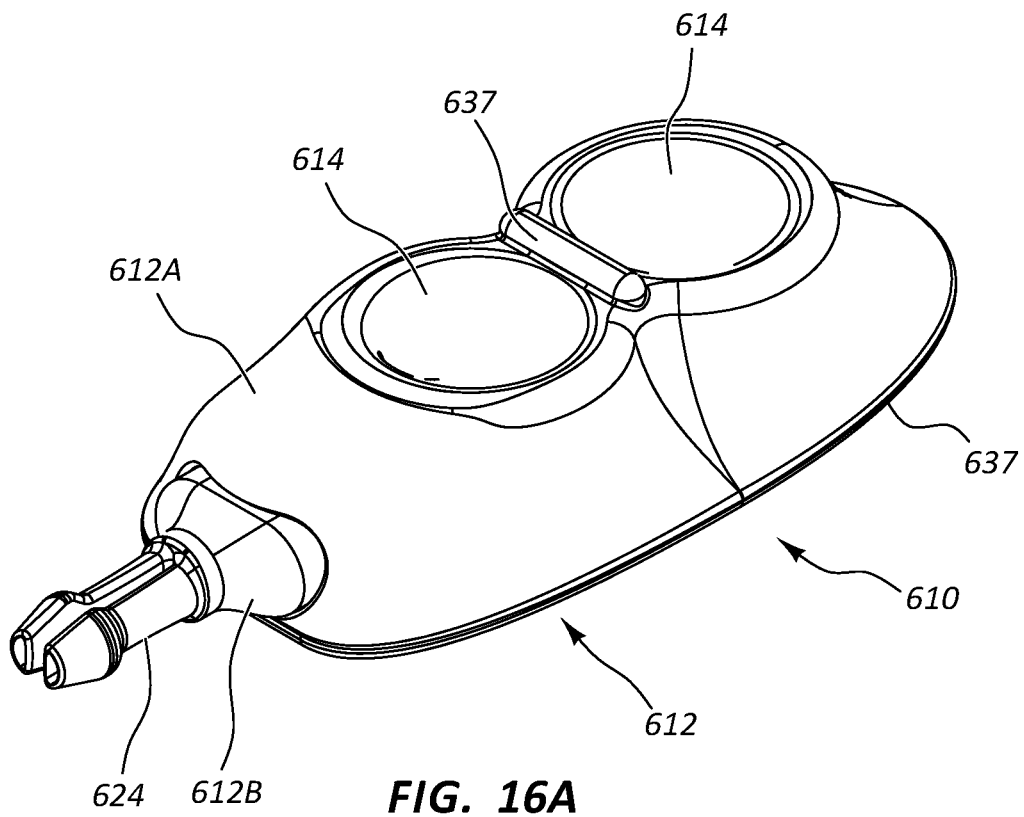
FIGS. 16A-16G depict various views of a low-profile vascular access device according to one embodiment.
Figure 16B:
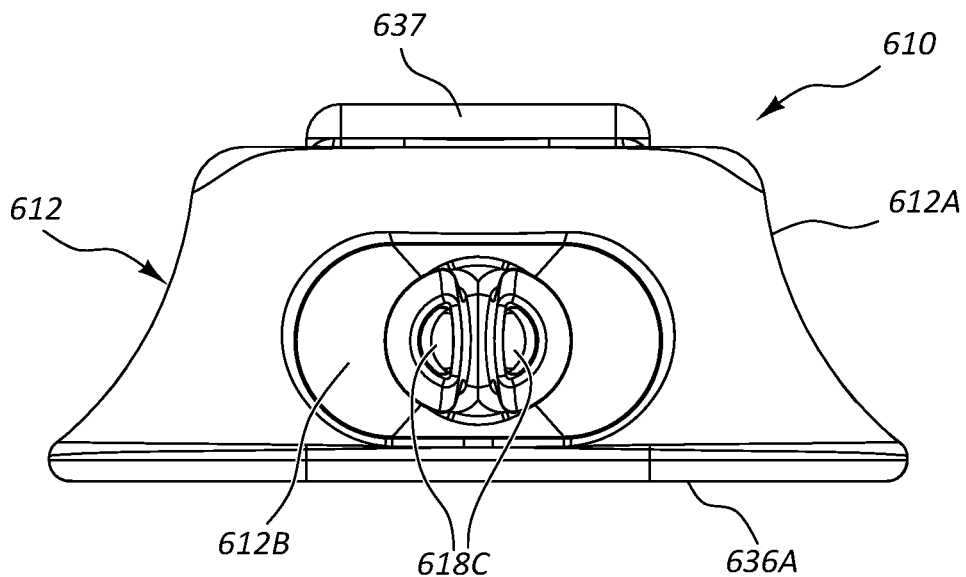
Figure 16C:
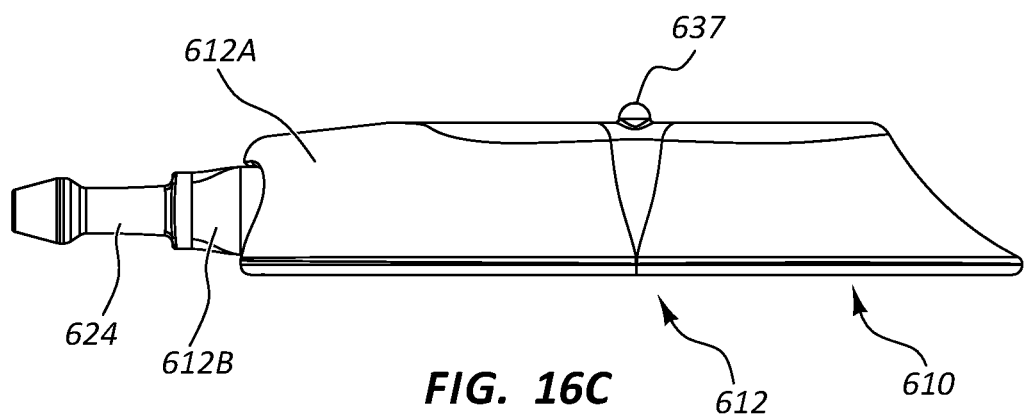
Figure 16D:
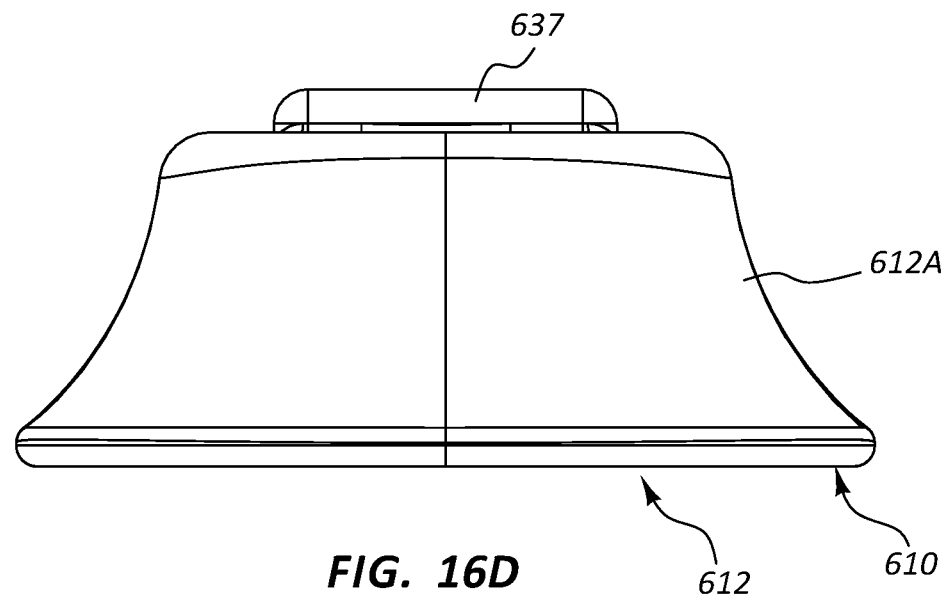
Figure 16E:
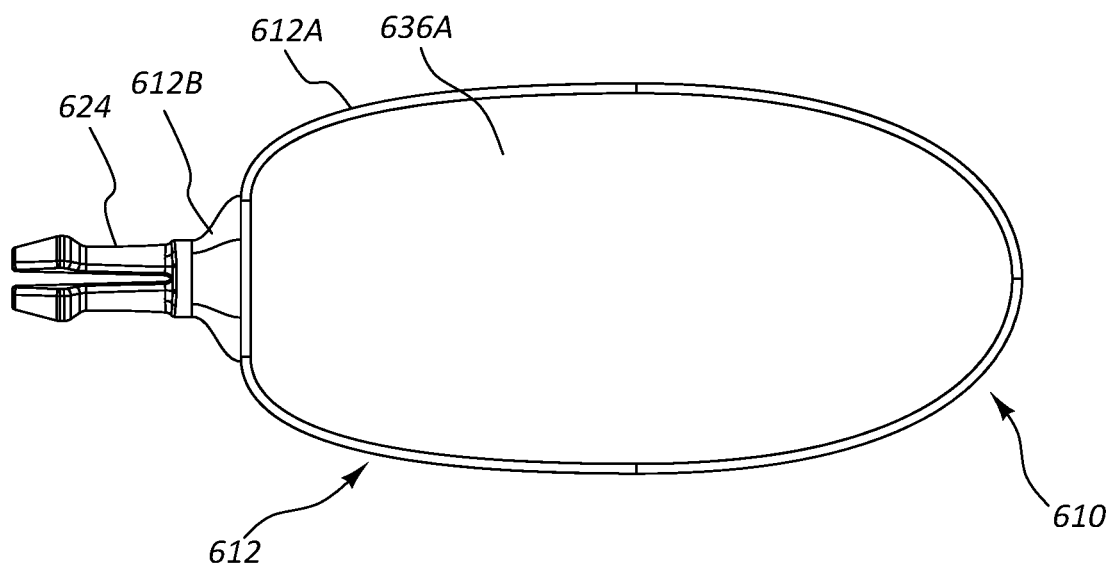
Figure 16F:
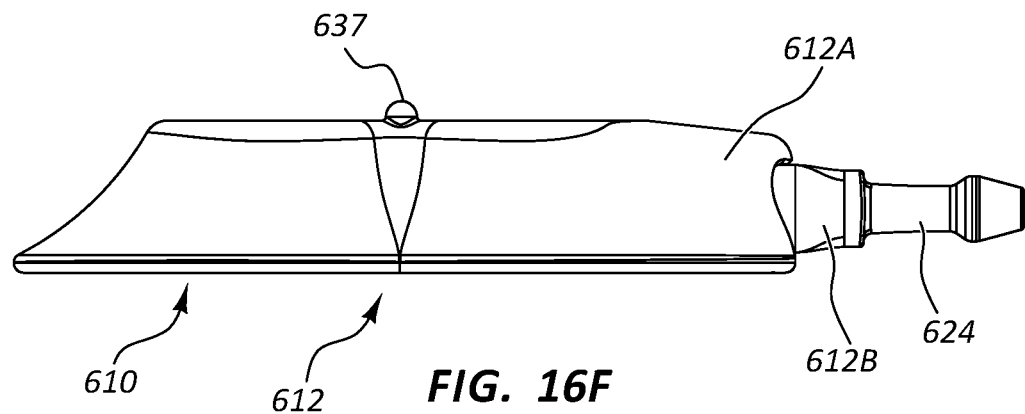
Figure 16G:
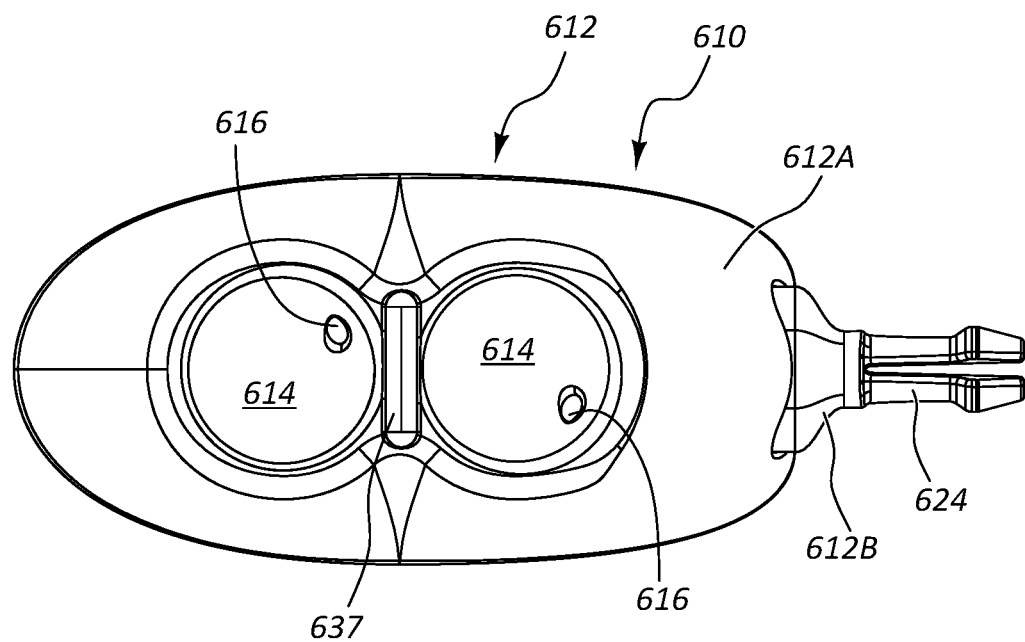

In particular, the substantially funneled-shape of each receiving cup 614 is configured to direct the catheter-bearing needle 42 impinging thereon toward an inlet port 616 that serves as an opening for a respective one of two conduits 618 defined by the port body 612, one conduit for each receiving cup. The open and shallow nature of each receiving cup 614, angled toward the skin surface of the patient enables the receiving cup to present a large, easily accessible target for the needle when introduced into the skin and directed toward the subcutaneously implanted access port 610. FIGS. 16C and 16F further show that the access port 610 defines a relatively low profile height, which enables relatively shorter needle lengths to be used for accessing the subcutaneous access port after implantation.

The port body 612 further defines a palpation feature 637, here configured as a raised surface interposed between the longitudinally aligned receiving cups 614. As mentioned above, the palpation feature 637 is included with the port body 612 to assist a clinician to locate and/or identify the port 610 via finger palpation after implantation under the skin of the patient. Note that a variety of sizes, configurations, numbers, etc., of palpation features can be included on the port. In another embodiment, a guide groove can be defined on each receiving cup 614 to be longitudinally aligned with the inlet port 616 of the conduit 618, as in previous embodiments.

Figure 17A:
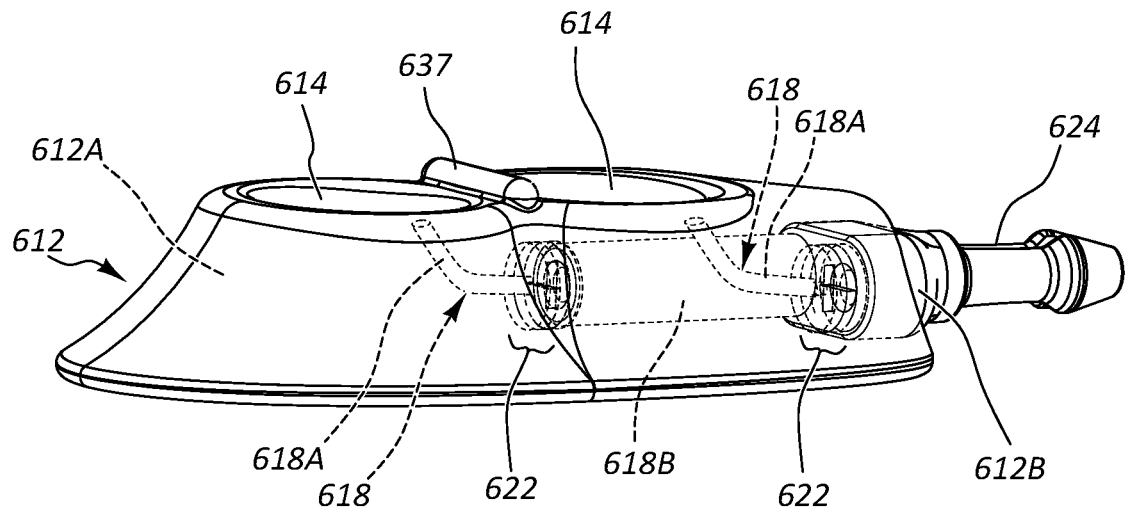
FIGS. 17A and 17B depict various views of the vascular access port of FIGS. 16A-16G.
Figure 17B:
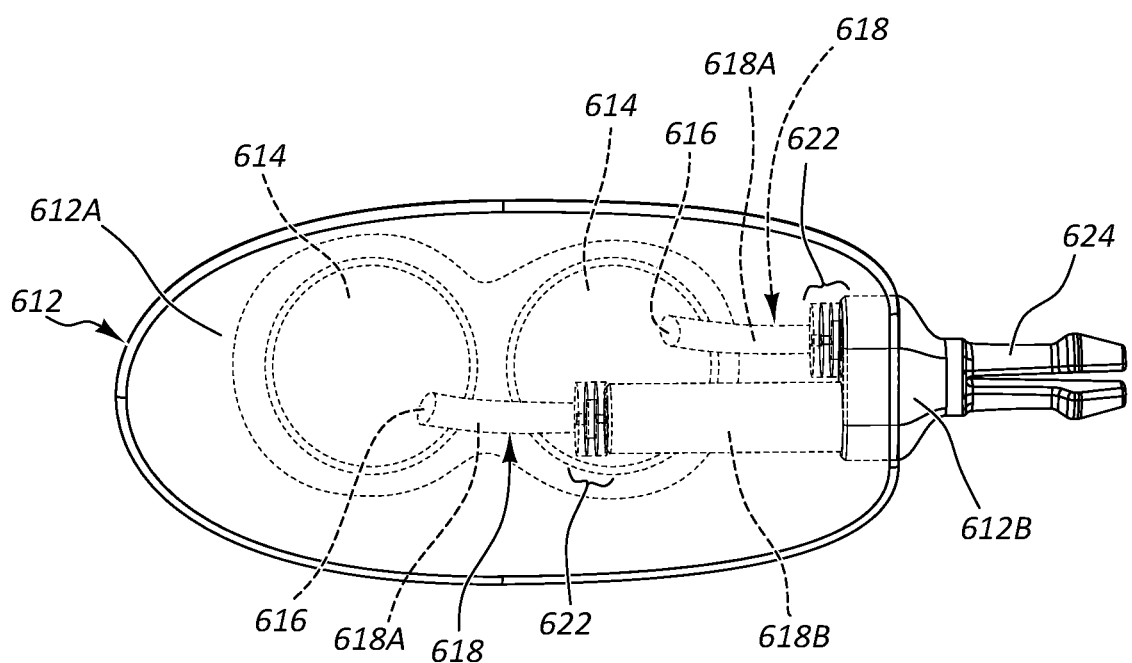
Figure 19:
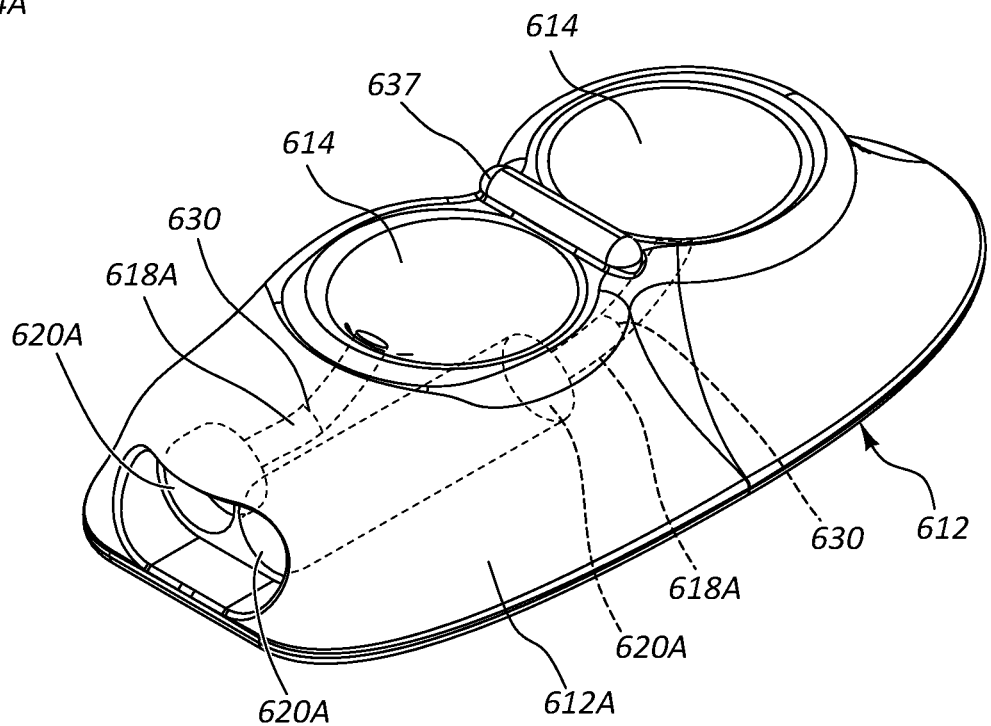
FIG. 19 is a partially transparent view of the vascular access device of FIGS. 16A-16G.

As best seen in FIGS. 17A, 17B, and 19, the port body 612 further defines the above-mentioned two conduits 618, each conduit serving as a pathway into which a transcutaneously inserted catheter can be partially inserted so as to place the catheter in fluid communication both with the port 610 and an indwelling dual-lumen catheter operably attached to two fluid outlets 624A of a stem 624 of the port. As shown, the two conduits 618 of the port body first portion 612A are in fluid communication with their respective receiving cup 614 via the corresponding inlet port 616. A first conduit portion 618A of each conduit 618 distally extends from the respective inlet port 616 in an angled downward direction from the perspective shown in FIG. 17A to a conduit bend 630 (FIG. 19), where the first conduit portion extends distally at a predetermined angle with respect to the first conduit portion proximal to the conduit bend. The magnitude of the predetermined angle at the bend 630 depends in one embodiment on various factors, including the size of the catheter and/or needle to be inserted into the port conduit, the size of the port and the conduit itself, etc. Note also that the conduit bend 630 serves as a needle-stop feature, preventing the needle 42 from advancing along the conduit 618 past the bend 630.

Figure 18:
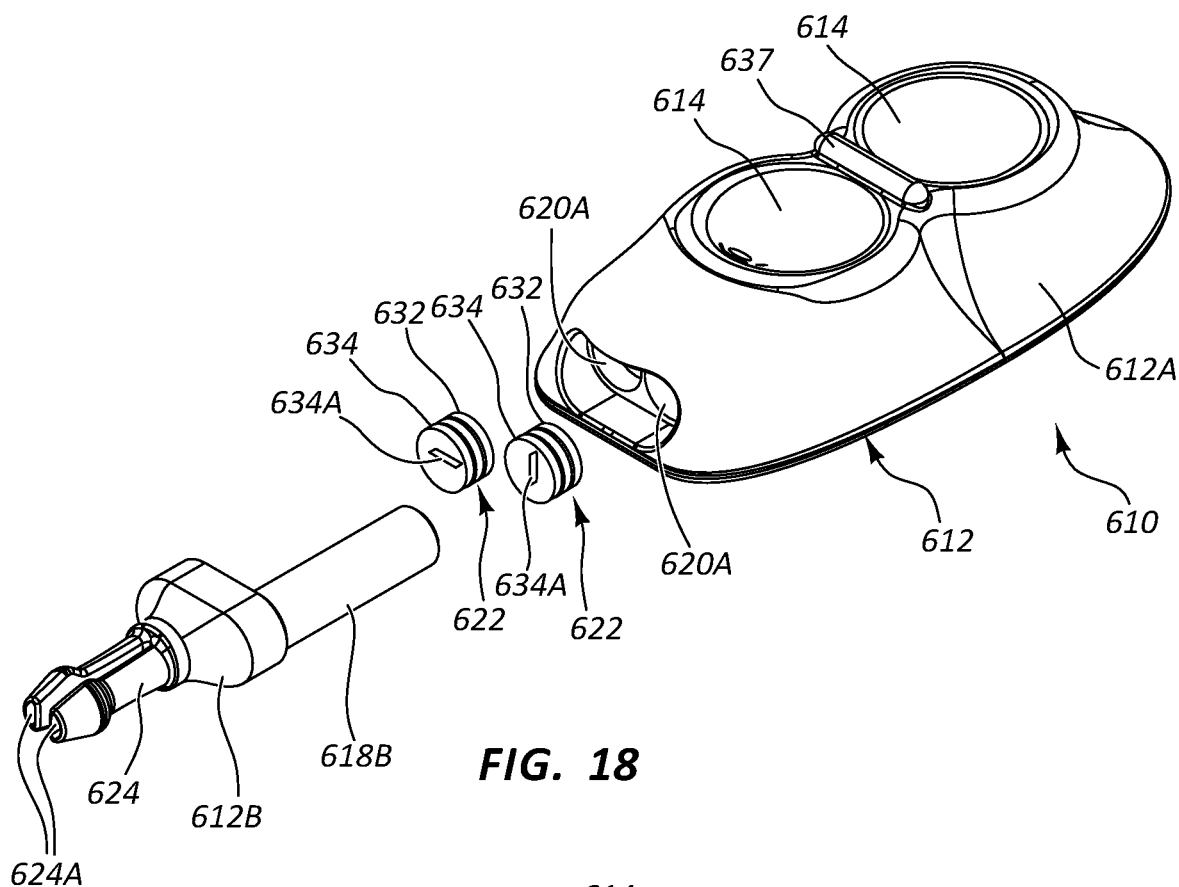
FIG. 18 is an exploded view of the vascular access device of FIGS. 16A-16G.

The first portion 618A of the relatively more distal of the two receiving cups 614 extends to a cavity 620A defined by and proximate to the distal portion of the first portion 612A of the port body 612, as best seen in FIGS. 18 and 19. The first portion 618A of the relatively more proximal of the two receiving cups 614 also extends to a cavity 620A that is defined by, but relatively more proximally distant from, the distal portion of the first portion 612A of the port body 612 (FIGS. 18 and 19). A second conduit portion 618B is defined for this latter conduit 618 by the second portion 612A of the port body 612, as seen in FIGS. 17A and 17B and extends distally from its respective cavity 620A until joining with a third conduit portion 618C defined by the second portion 612A of the port body, which extends through the second portion and the stem 624 until terminating at a respective one of the fluid outlets 624A (FIG. 20).

Figure 20:
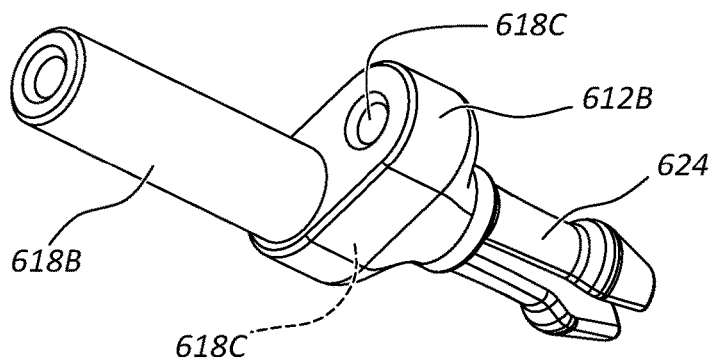
FIG. 20 is a perspective view of a portion of the vascular access device of FIGS. 16A-16G.
Figure 21A:
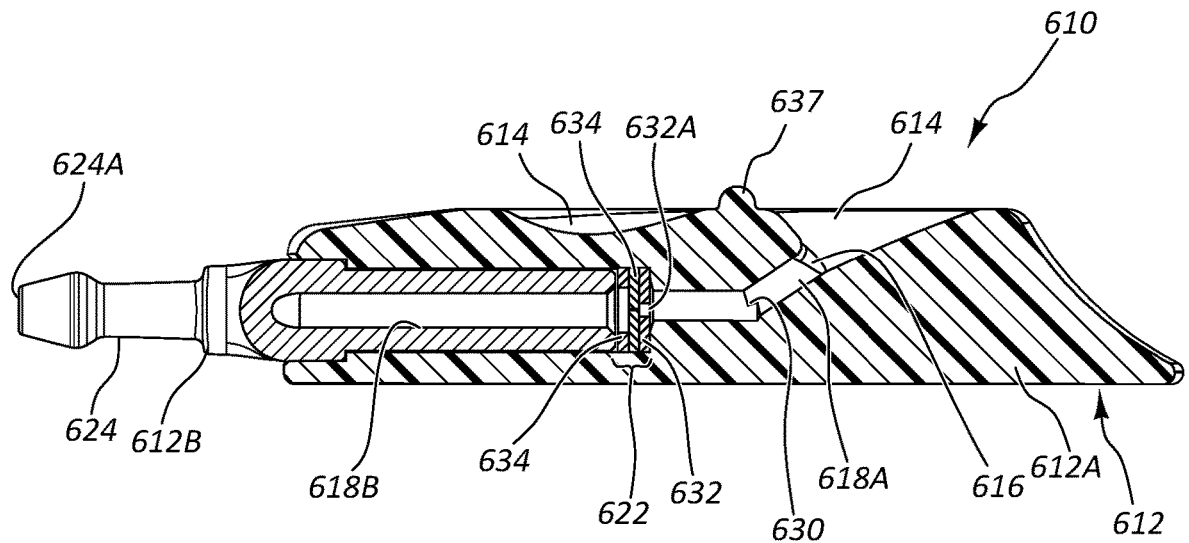
FIGS. 21A and 21B are cutaway views of the vascular access device of FIGS. 16A-16G.
Figure 21B:
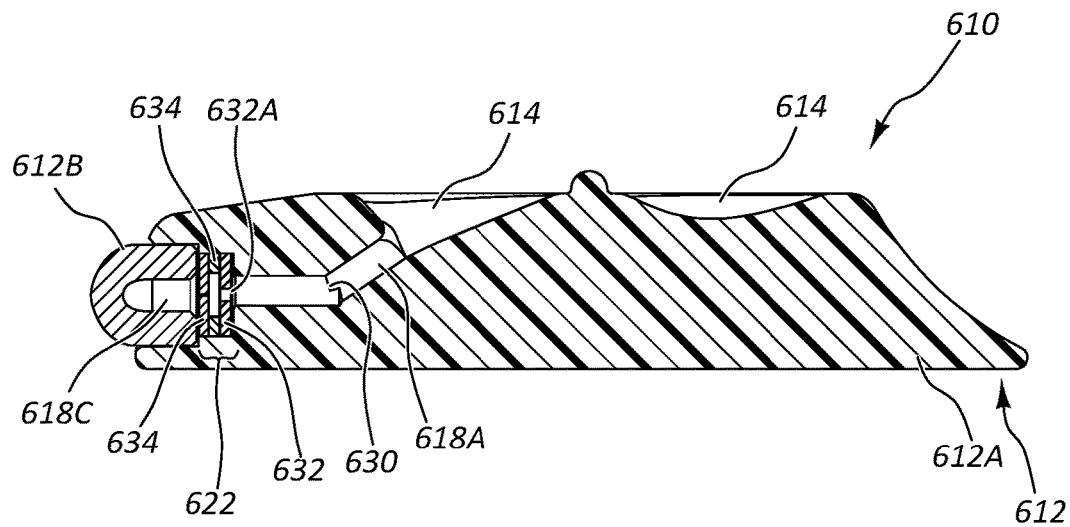

The conduit 618 for the relatively more distal receiving cup 614 extends from the cavity 620A to a third conduit portion 618C defined by the second portion 612A of the port body 612, as seen in FIG. 20, which extends through the second portion and the stem 624 until terminating at a respective one of the fluid outlets 624A. In this way, fluid pathways are defined for each receiving cup 614 from the inlet port 616 to the stem fluid outlet 624A, as depicted in FIGS. 21A and 21B. In the present embodiment the conduit 618 is sized so as to enable the catheter 40 (FIG. 14A) to pass therethrough past the cavity 620A.

As mentioned, the cavities 620A, each disposed in the fluid pathway defined by the various portions of the conduits 618, each define a space through which the conduit 618 passes and in which is housed a valve/seal assembly 622. In the present embodiment and as best seen in FIGS. 17A-18, each valve/seal assembly 622 includes a sealing element, or seal 632, which defines a central hole 632A (FIG. 21B) through which the catheter 40 (FIGS. 14A, 14D) can pass, and two adjacently placed slit valves 634, each slit valve including a single slit 634A (with the valves being arranged such that the slits are orthogonal to one another), through which the catheter also passes. The seal 632 and slit valves 634 are sandwiched together in one embodiment, with the seal disposed proximal to the slit valve, and secured in place within the correspondingly sized cavity 620A as shown in FIGS. 17A and 17B. In another embodiment, the valve/seal assembly includes a single seal and a single, dual-slit valve, as in previous embodiments.

In the present embodiment, the seal 632 and valves 634 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 632 and valves 634 to enhance lubricity and extend component life. In another embodiment, the silicone oil is infused into the silicone. Also, and as has been mentioned with other embodiments, other seal/valve configurations can also be employed in the port 610.

Reference is now made to FIGS. 22A-24, which show various details of a dual-lumen vascular access device, generally designated at 710, in accordance with one embodiment. As shown, the port 710 includes a body 712 that is defined in the present embodiment by a first portion 712A defining the majority of the external portion of the port body and a second portion 712B that is matable to the first portion. In the present embodiment the port body first and second portions 712A, 712B include a metal such as titanium, and as such, the second portion is press fit into engagement with the first portion to define the body 212, though it is appreciated that the port body can include a variety of other materials, including metals, thermoplastics, ceramics, etc., and can include other joining methods including adhesive, ultrasonic or other welding, interference fit, etc.

The port body first portion 712A defines in the present embodiment two substantially concavely-shaped receiving cups 714, side-by-side in a spaced-apart arrangement, for receiving and directing the catheter-bearing needle 42 (FIG. 14A) to operably connect with the port 710 in a manner similar to that already described above. In particular, the substantially concave shape of each receiving cup 714 is configured to direct the catheter-bearing needle 42 impinging thereon toward an inlet port 716 that serves as an opening for a respective conduit 718 defined by the port body 712.

Figure 22A:
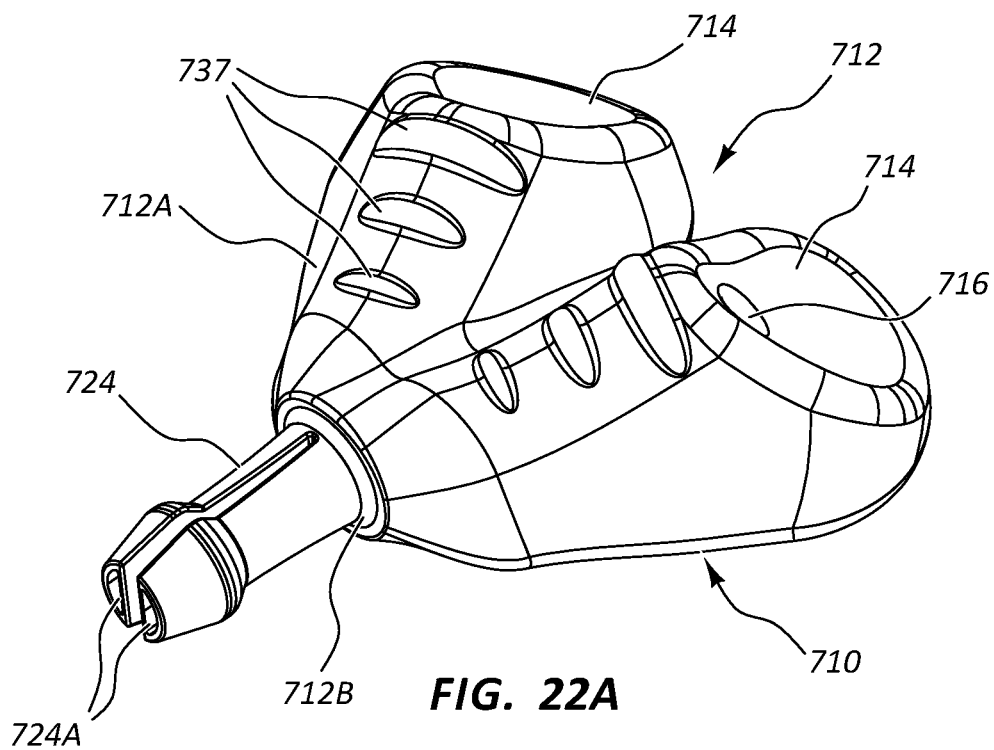
FIGS. 22A-22C depict various views of a low-profile vascular access device according to one embodiment.
Figure 22B:
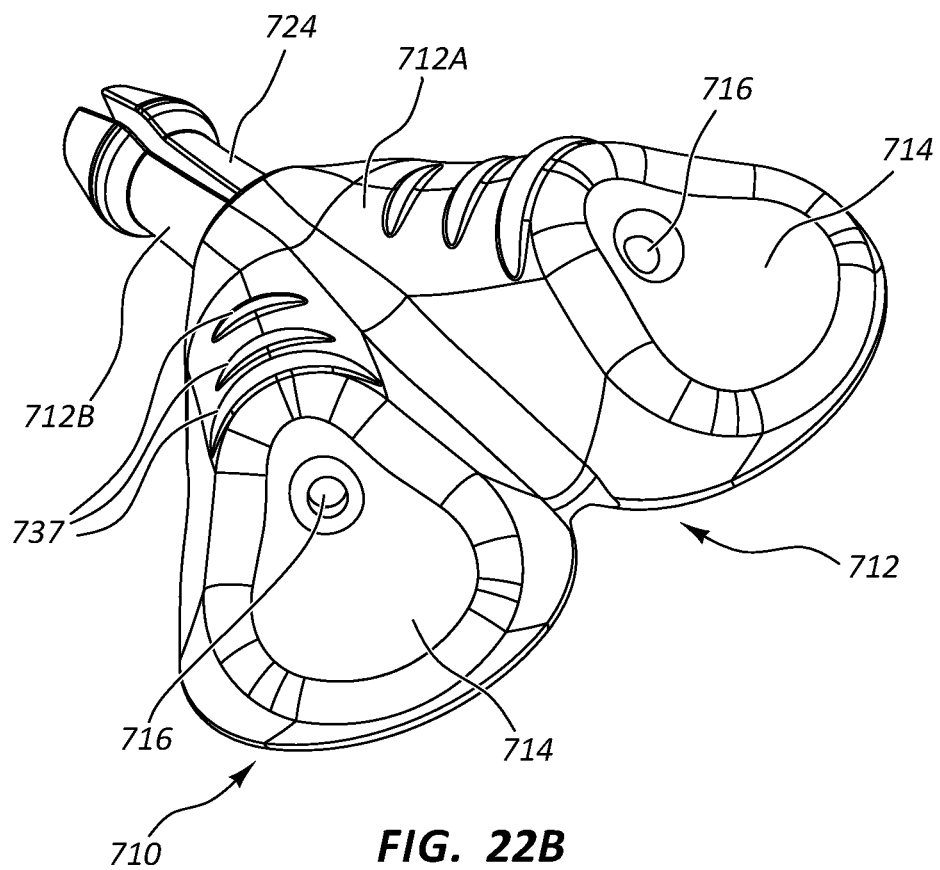
Figure 22C:
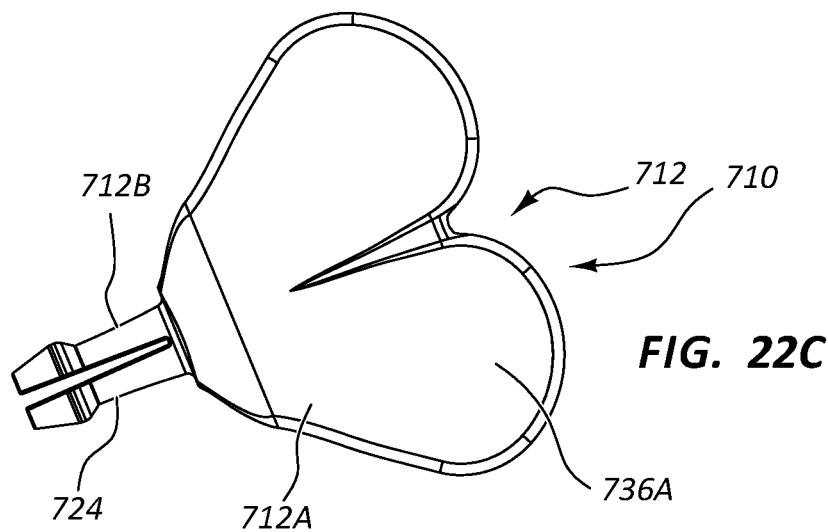

The open and shallow nature of each receiving cup 714, angled toward the skin surface of the patient enables the receiving cup to present a large, easily accessible target for the needle when introduced into the skin and directed toward the subcutaneously implanted access port 710. FIGS. 22A and 22B further show that the access port 710 defines a relatively low profile height, which enables relatively shorter needle lengths to be used for accessing the subcutaneous access port after implantation. FIG. 22C depicts details of a bottom portion of the port body 712. Note that in this and other embodiments, the receiving cups can define different surfaces, including funnel-shaped, concave-shaped, hemispherical, etc.

The port body 712 includes a plurality of palpation features 737, here implemented as ridges extending distally from the receiving cups 714, to assist a clinician to locate and/or identify the port 710 via finger palpation after implantation under the skin of the patient. Note that a variety of sizes, configurations, numbers, etc., of palpation features can be included on the port.

Figure 23:
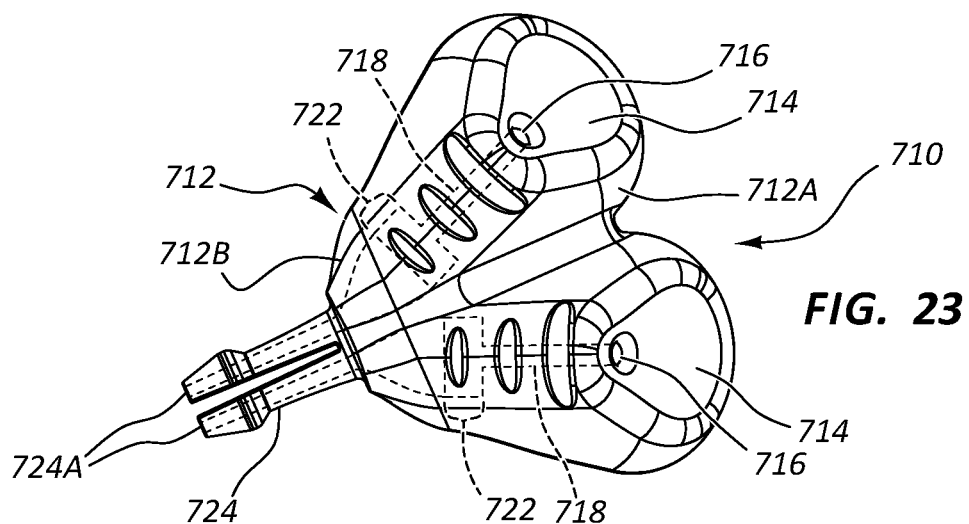
FIG. 23 is a partially transparent view of the vascular access device of FIGS. 22A-22C.
Figure 24:
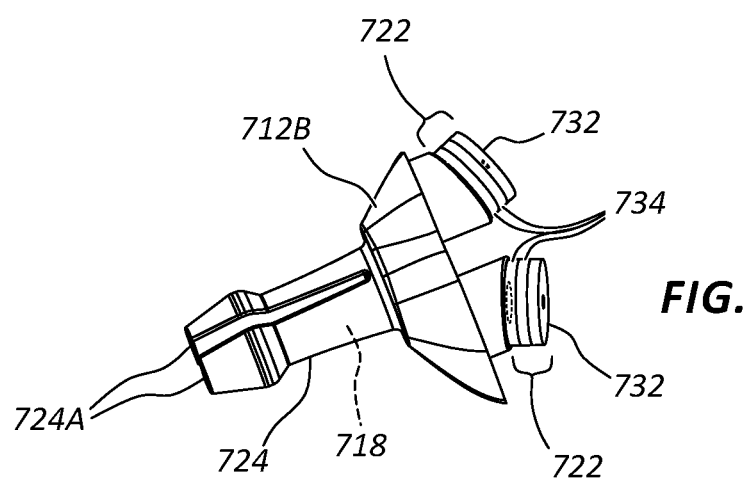
FIG. 24 is a partially transparent view of a portion of the vascular access port of FIGS. 22A-22C.

As best seen in FIGS. 23 and 24, the port body 712 further defines the two conduits 718, each conduit serving as a pathway into which a transcutaneously inserted catheter can be partially inserted so as to place the catheter in fluid communication both with the port 710 and an indwelling dual-lumen catheter operably attached to two fluid outlets 724A of a stem 724 of the port. As shown, each of the two conduits 718 of the port body first portion 712A is in fluid communication with its respective receiving cup 714 via the inlet port 716 and extends distally to a valve/seal assembly 722 disposed in a cavity cooperatively defined by the junction of the port body first portion 712A and the second portion 712B. As with other embodiments herein, each conduit 718 distally extends from the respective inlet port 716 in an angled downward direction from the perspective shown in FIG. 23 to a conduit bend before continuing to the cavity wherein is disposed the valve/seal assembly. Note that the conduit bend can desirably serve as a needle-stop feature, preventing the needle 42 from advancing along the conduit 718 past the bend. The conduits distally extend past the valve/seal assembly 722 and through the port body second portion 712B to the fluid outlets of the stem 724. In the present embodiment the conduit 718 is sized so as to enable the catheter 40 (FIG. 14A) to pass therethrough past the valve/seal assembly 722.

As mentioned, the cavities, each defined by the junction of the respective first portion 712A and the second portion 712B of the port body 712, each define a space through which the conduit 718 passes and in which is housed the valve/seal assembly 722. In the present embodiment and as best seen in FIGS. 23 and 24, each of the two valve/seal assemblies 722 includes a sealing element, or seal 732, which defines a central hole through which the catheter 40 (FIGS. 14A, 14D) can pass, and two slit valves 734, each including a single slit and positioned adjacent each other such that the slits are substantially orthogonal to one another, through which the catheter also passes. The seal 732 and the slit valves 734 are sandwiched together in one embodiment, with the seal disposed proximal to the slit valves, and secured in place within the correspondingly sized cavity as shown in FIGS. 23 and 24.

As mentioned, the slits of the slit valves 734 are orthogonally offset from one another by about 90 degrees in the present embodiment, though other relationships are possible, including the use of a single slit valve including two orthogonal slits. These and other modifications to this and the other valve/seal assembly embodiments herein are therefore contemplated.

As with previous embodiments, the seal 732 and slit valves 734 of the valve/seal assembly 722 cooperate to enable fluid-tight passage therethrough of the catheter 40 (see, e.g., FIG. 14A) while also preventing backflow of fluid through the valve/seal assembly. Indeed, in one embodiment the seals disclosed herein prevent fluid flow around the external portion of the catheter when the catheter is disposed through the seal 732, while the valve 734 is suitable for preventing fluid flow when no catheter passes through them. As such, when the catheter 40 is not inserted therethrough the valve/seal assembly 722 seals to prevent passage of air or fluid through the conduit 718. In the present embodiment, the seal 732 and valve 734 are composed of silicone, such as SILASTI$^C$® Q7-4850 liquid silicone rubber available from Dow Corning Corporation, though other suitably compliant materials can be employed. In one embodiment, silicone oil, such as NuSil Technology Med 400 silicone oil, is included with the seal 732 and valve 734 to enhance lubricity and extend component life. In another embodiment, the silicone oil is infused into the silicone.

Though not explicitly shown here, the port 710, as with other embodiments herein, can include radiopaque indicia configured to enable the port to be radiographically identified after implantation into the patient body. In one embodiment, the indicia include the letters "IV" and "CT" to indicate suitability of the port 710 to receive peripheral IV catheters and that the port is capable of power injection of fluids therethrough. Of course, a variety of other indicia, including letters, numbers, symbols, etc., may be used.

Though single and dual-port configurations have been described herein, it is appreciated that ports including more than two receiving cups are contemplated. Note also that certain of the receiving cups described herein are described as funnel shaped, while other receiving cups are described herein as concavely shaped. It is noted that that the receiving cups can interchangeably include aspects of one or the other, or both, of these receiving cup shapes, according to a particular embodiment.

Figure 27:
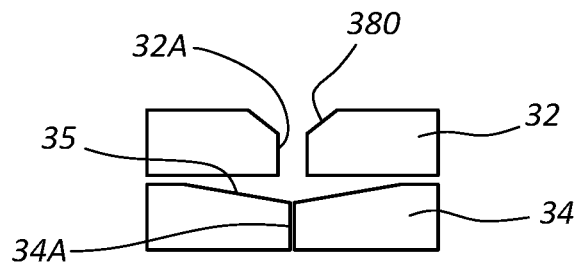
FIG. 27 is a cross-sectional view of a valve/seal configuration according to one embodiment.
Figure 28:
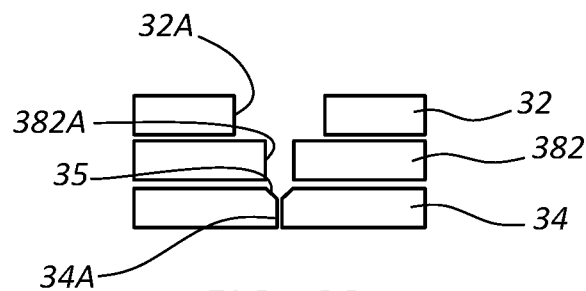
FIG. 28 is a cross-sectional view of a valve/seal configuration according to one embodiment.
Figure 29:
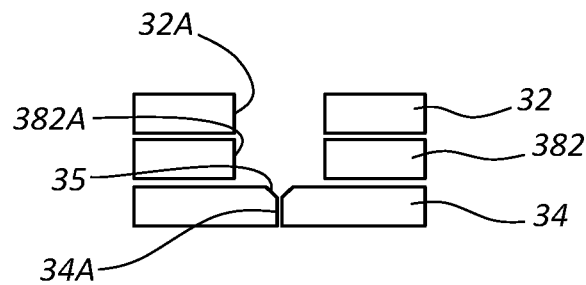
FIG. 29 is a cross-sectional view of a valve/seal configuration according to one embodiment.

FIGS. 27-30 depict details of various possible configurations for the valve/seal assembly, according to example embodiments. In FIG. 27, the seal 32 includes a central depression 380, similar but relatively steeper than the depression 35 of the valve 34. In FIG. 28, two seals are included—the seal 32 and a second seal 382 interposed between the seal 32 and the valve 34. The second seal 382 includes a central hole 382A that includes a diameter smaller relative to the hole 32A of the seal 32. FIG. 29 includes a similar configuration, but the hole 382A is similar in size to the hole 32A. A small central depression 35 is included on the valve 34 in both FIG. 28 and FIG. 29.

Figure 30:
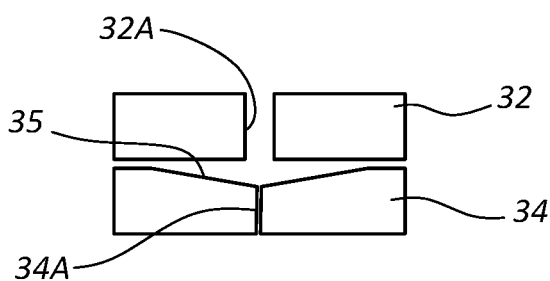
FIG. 30 is a cross-sectional view of a valve/seal configuration according to one embodiment.

In FIG. 30, the seal 32 includes a relatively small-diameter central hole 32A, and the valve 34 includes a relatively large central depression 35. Note that the valve/seal assemblies shown in FIGS. 27-30 are oriented in the figures such that the catheter pierces the seals and valves in a direction corresponding from the top of the page toward the bottom of the page.

Figure 32A:
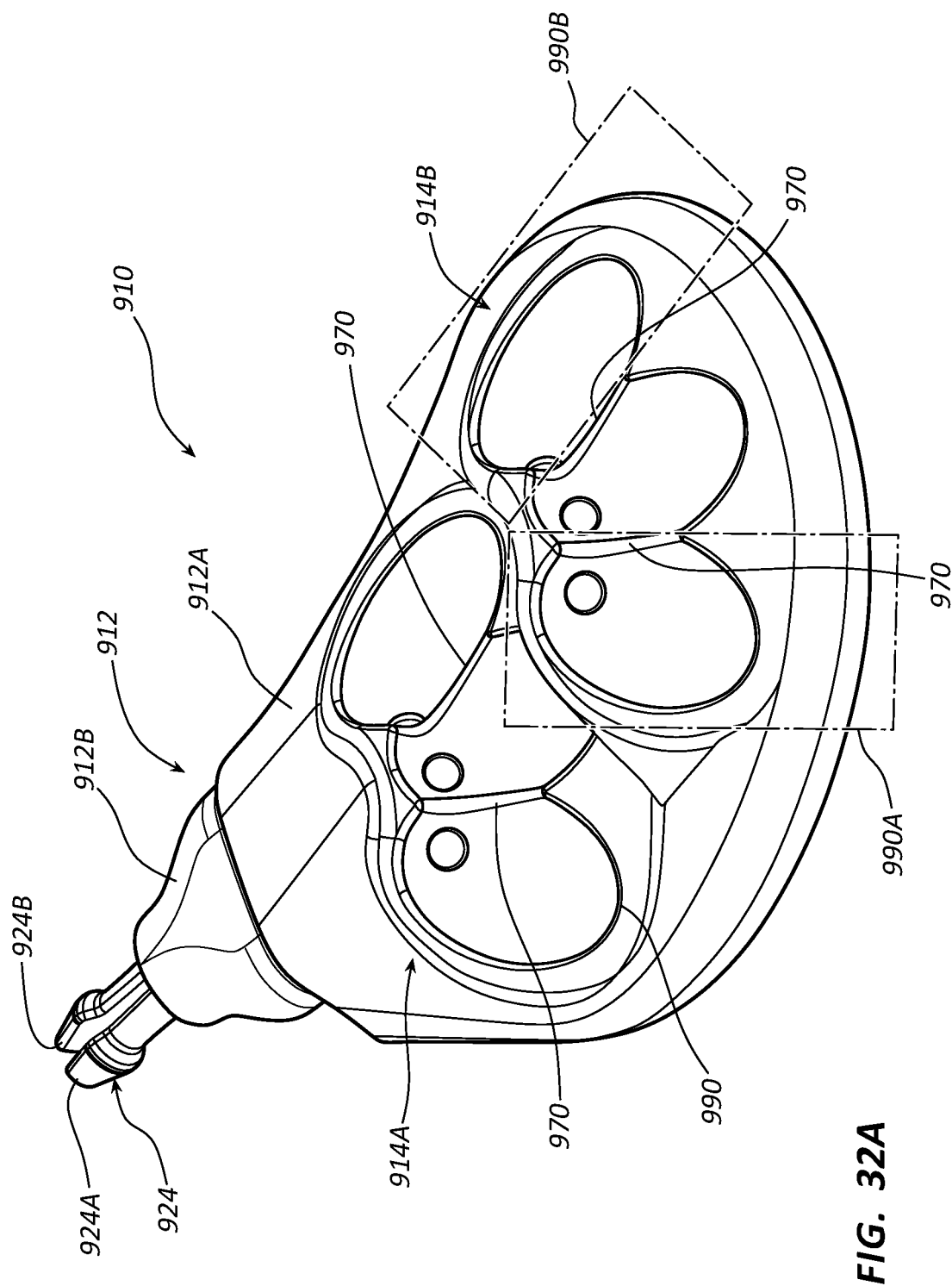
FIGS. 32A-32B depict perspective views of a low-profile vascular access device according to one embodiment.
Figure 32B:
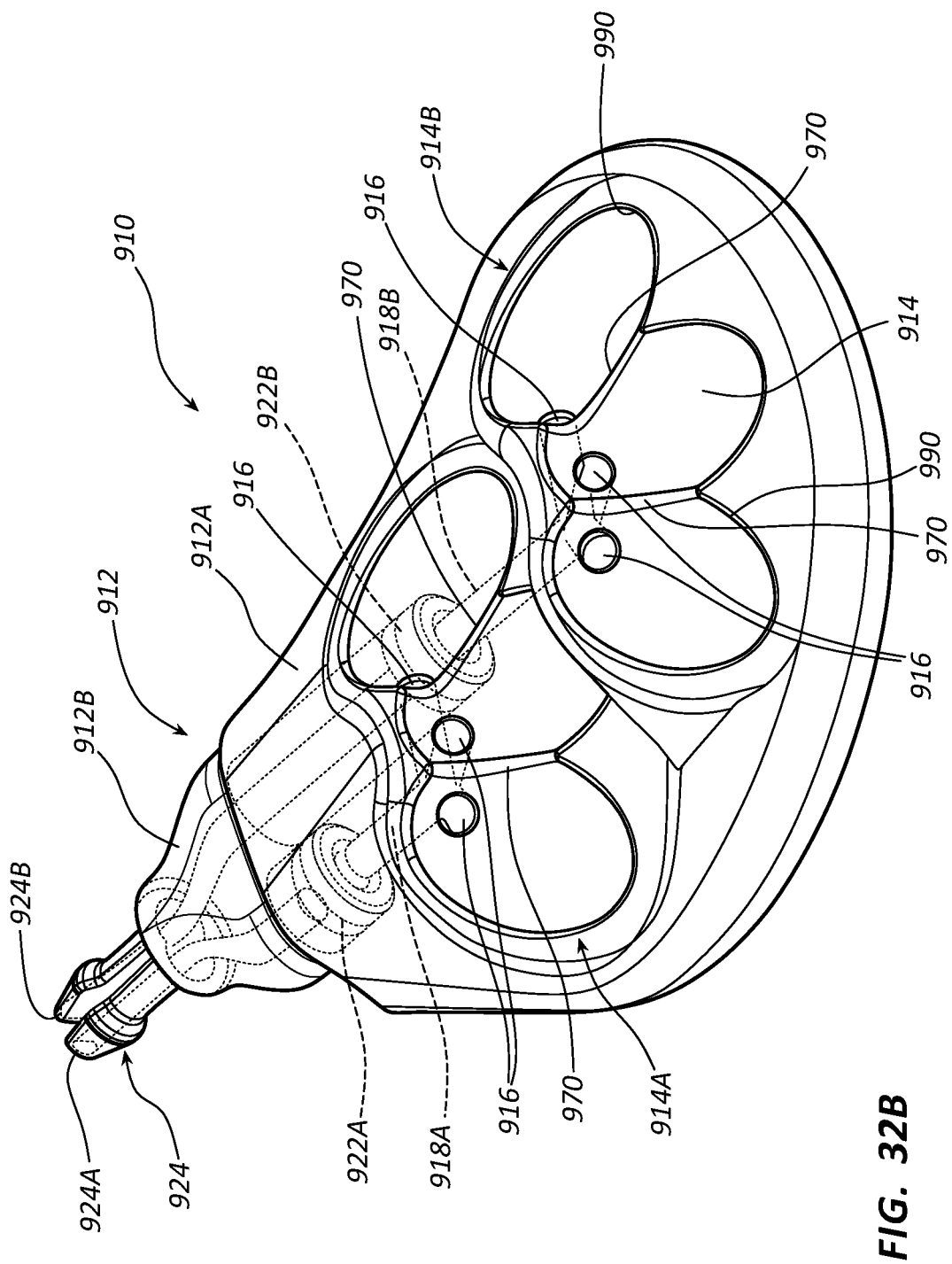

Reference is now made to FIGS. 32A-32B, which show various details of a multi-lumen vascular access device, generally designated at 910 in accordance with one embodiment. As shown, the port 910 includes a body 912 that is defined in the present embodiment by a first portion 912A and a relatively smaller second portion 912B that is partially received within the first portion 912A. In the present embodiment, the port body first and second portions 912A, 912B include a metal such as titanium, and as such, the second portion is press fit into engagement with the first portion to define the body 912. However, it will be appreciated that the port body can include a variety of other suitable materials, including metals, thermoplastics, ceramics, etc., and can include other joining methods including snap-fitted, adhesive, ultrasonic or other welding, interference fit, etc., as discussed herein.

The port body first portion 912A defines in the present embodiment a plurality of substantially funnel-shaped receiving cups 914 for receiving and directing the catheter-bearing needle 42 (FIG. 14A) to operably connect with the port 910 in a manner similar to that already described above. The receiving cups 914 in the present embodiment are disposed in sets, or groups, so as a first set of receiving cups 914A and second set of receiving cups 914B are substantially aligned along a longitudinal axis of the port 910, such that a first set 914A is proximal to second set of receiving cups 914B, though other positional arrangements for the receiving cups are possible, including side-by-side, spaced-apart, staggered, etc. As shown in FIG. 32B, each set of receiving cups 914A, 914B include three individual receiving cups 914, although it will be appreciated that a greater or fewer number of receiving cups 914 within each set 914A, 914B are contemplated and fall within the scope of the present invention.

In an embodiment, port body 912 includes sets of receiving cups 914A, 914B that include individually defined receiving cups 914 similar to those shown in FIG. 25A. In an embodiment, as shown in FIG. 32A, each of the receiving cups 914 within a set 914A, 914B can be joined to one another along cutouts 970. This enables the receiving cups 914 to reside relatively close to one another and provide port body 912 with a relatively slimmer profile than that of an embodiment where receiving cups 914 are individually defined. The receiving cups 914 of each set 914A, 914B can be joined to one another along the cutouts 970 via welding, adhesive, forming the welding cups together as a single component. In an embodiment each set of receiving cups 914A, 914B are formed as a single monolithic piece. In an embodiment, port body second portion 912B is formed as a single monolithic piece.

The substantially funneled-shape of each receiving cup 914 is configured to direct the catheter-bearing needle 42 impinging thereon toward a corresponding inlet port 916 for each cup 914. Each set of receiving cups 914A, 914B then communicates with a single conduit 918, i.e. conduit 918A, 918B respectively. The conduits 918A, 918B, in turn communicate with a corresponding stem fluid outlet 924A, 924B of port stem 924, as described herein. Further, each of the conduits 918 can include valve/seal assemblies 922, also as described herein. Accordingly, a given conduit, e.g. 918A or 918B, can accessed by any of the receiving cups within a corresponding set of receiving cups 914A, 914B. One embodiment of suitable internal inlet port 916/conduit 918 routing is disclosed in FIG. 32B.

Advantageously, this allows a user to access a conduit 918 via multiple needle entry points. Accordingly, the port 910 is suitable for implantation under the skin of a dialysis patient, or patient undergoing similar extracorporeal treatments that require infusion and removal of fluids from the vasculature. Multiple needle entry points can be used and can be alternately selected over the course of multiple dialysis treatments so that no single locus of the patient's skin needs to be consecutively penetrated by a needle in order to access a given conduit 918.

In an embodiment, each the receiving cups 914 within a set can be oriented along a similar plane, such that they are co-aligned. In an embodiment, each of the receiving cups 914 within a set are angled with respect to one another such that a perimeter 990 of a first receiving cup 914 lies in an imaginary plane 990A that is non-parallel the planes defined by the perimeters of the other receiving cups 914 within the set, for example plane 990B defined by a second receiving cup 914, as described herein (FIG. 31). Such a configuration results in each of the receiving cups 914 within a set 914A, 914B being angled away from one another. This, in turn, desirably results in a slightly lower height profile for the access port 910, and can also result in the needle 42 inserted therein residing relatively closer to the patient skin. Further, the angled receiving cups 914 provide a greater skin surface with which to access the port 910. Accordingly, repeated access can be achieved using a greater number of needle access points so that no single locus of the patient's skin needs to be consecutively penetrated by a needle, allowing previous sites to heal. Note that the receiving cups can be angled in various different configurations in addition to what is shown and described herein.

Although two sets of three receiving cups each are shown, it will be appreciated that any number of receiving cups, or number of sets thereof, fall within the scope of the present invention. Accordingly, in an embodiment, one set of receiving cups may be configured for blood withdrawal, and the other set configured for blood return.

Figure 33:
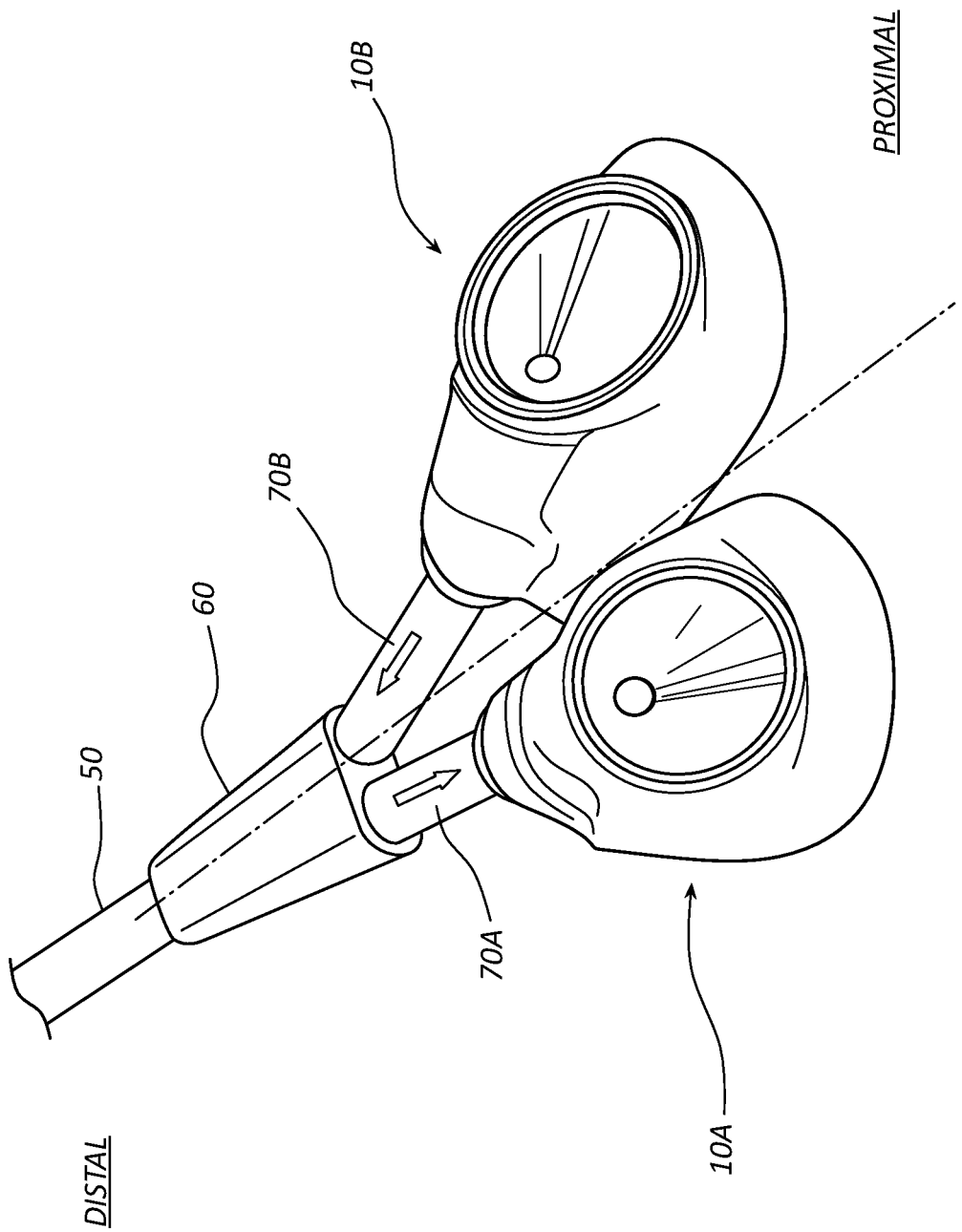
FIG. 33 depict a perspective view of a low-profile vascular access device according to one embodiment.

Reference is now made to FIG. 33 which illustrates an embodiment of a subcutaneous catheter assembly. The catheter assembly comprises a catheter 50, a bifurcation hub 60, an extension leg 70, such as extension legs 70A, 70B, and a port 10. The catheter 50 can be a multi-lumen catheter, such as a dual lumen dialysis catheter where each lumen is fluidly connected with an extension leg 70A, 70B. A port 10 is fluidly connected with a proximal end of the extension leg 70 and can be configured for receiving dialysis needles or large gauge over-the-needle intravenous catheters. Accordingly, a first port 10A can be accessed to fluid removal and a second port 10B can be access for fluid return. Each port 10 can include palpation features, indicia, guide grooves, radiopaque markers, or other features of other embodiments as disclosed herein.

Advantageously, the length and flexibility of the extension legs 70 allow an amount of variation in positioning of the ports 10A, 10B relative to each other. Accordingly, the ports can be positioned to alter the access locus on the patient's skin without having to reposition the entire device. Further, individual ports 10 can be replaced as needed without having to replace the entire device. It will be appreciated that alternate embodiments of port as disclosed herein can be used in place of port 10. Further, catheters with different numbers of lumens and gauge sizes can also be used and fall within the scope of the present invention.

Figure 34A:
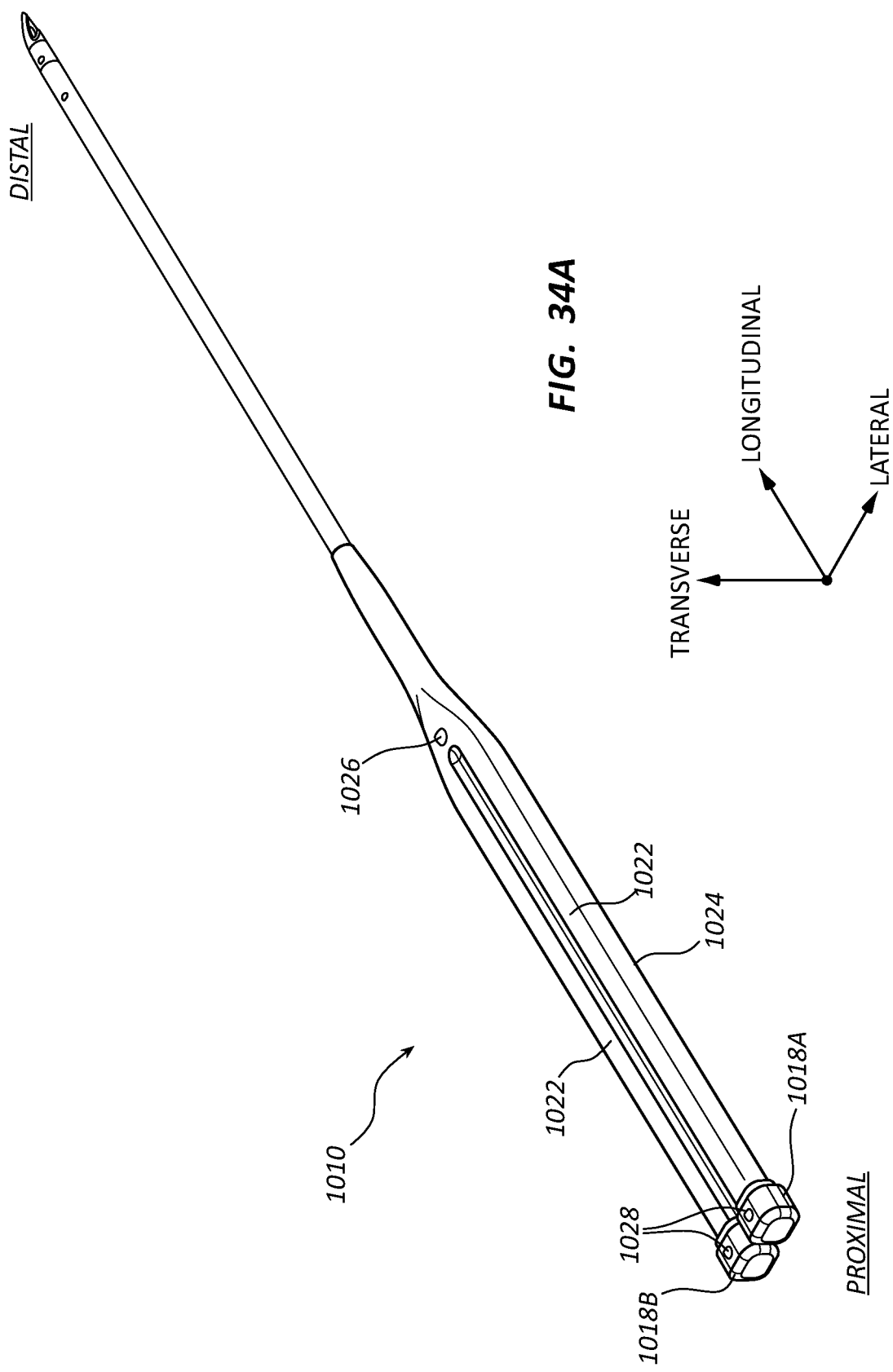
FIGS. 34A-34B depict perspective views of a low-profile vascular access device according to one embodiment.
Figure 34B:
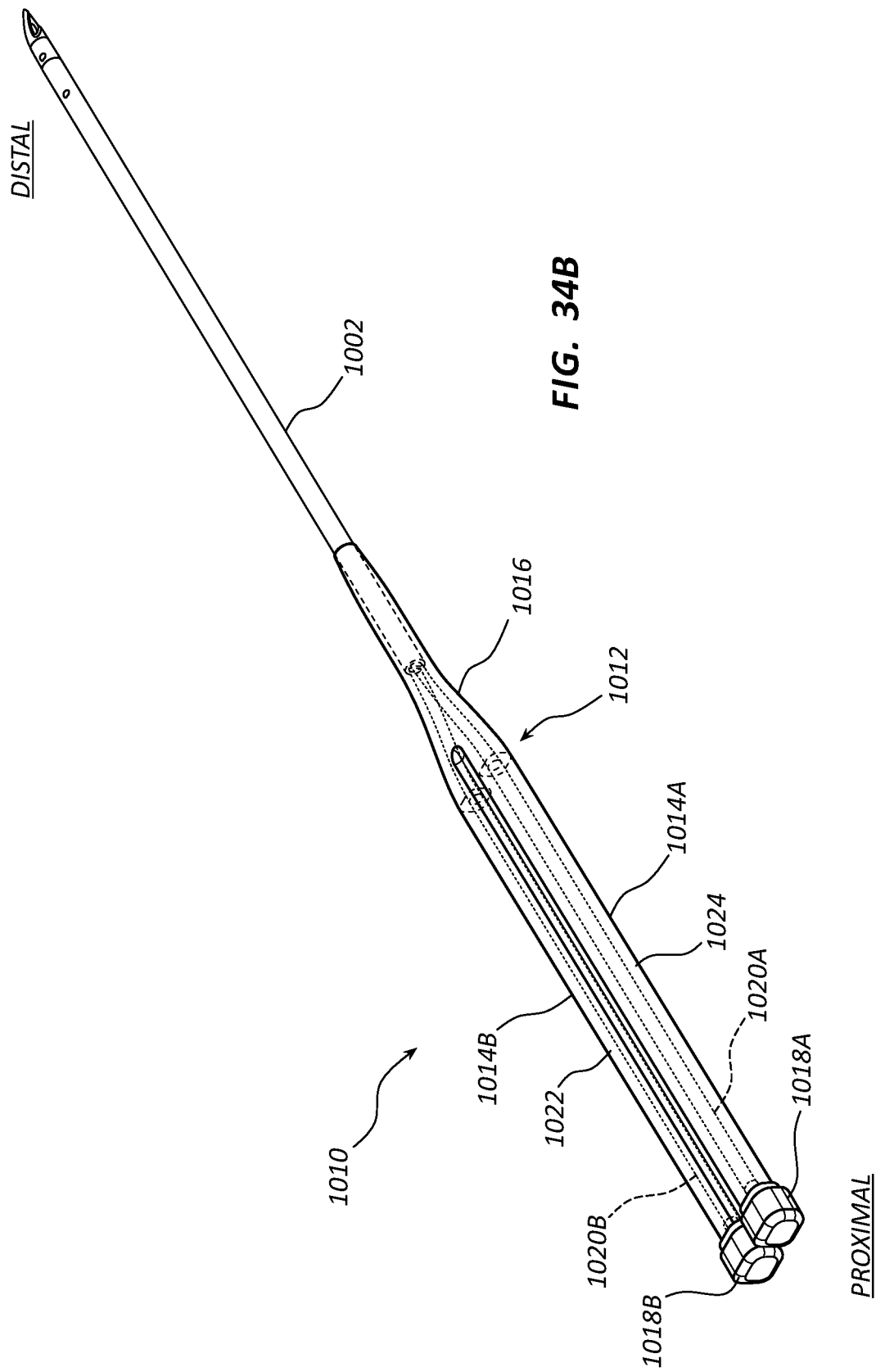
Figure 35J:
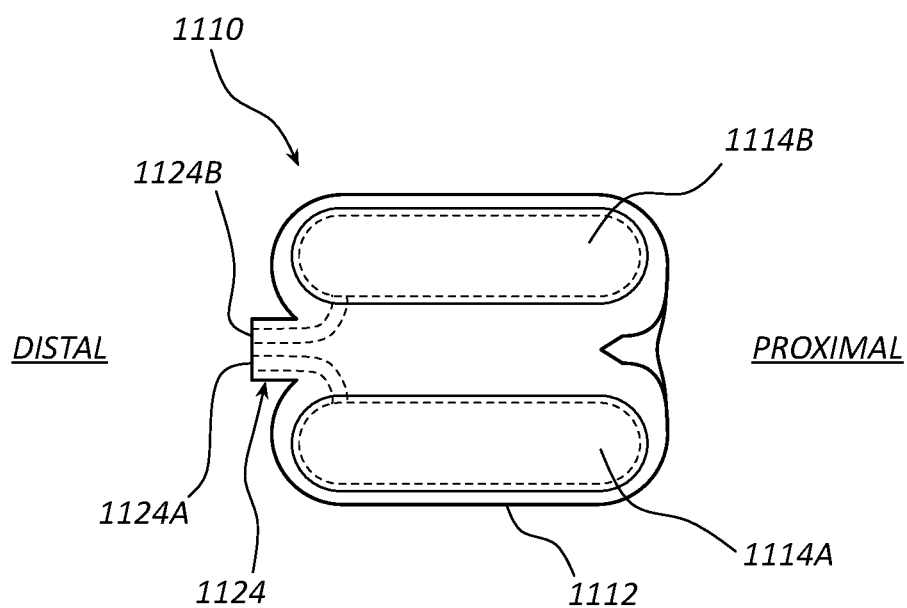
Figure 36A:
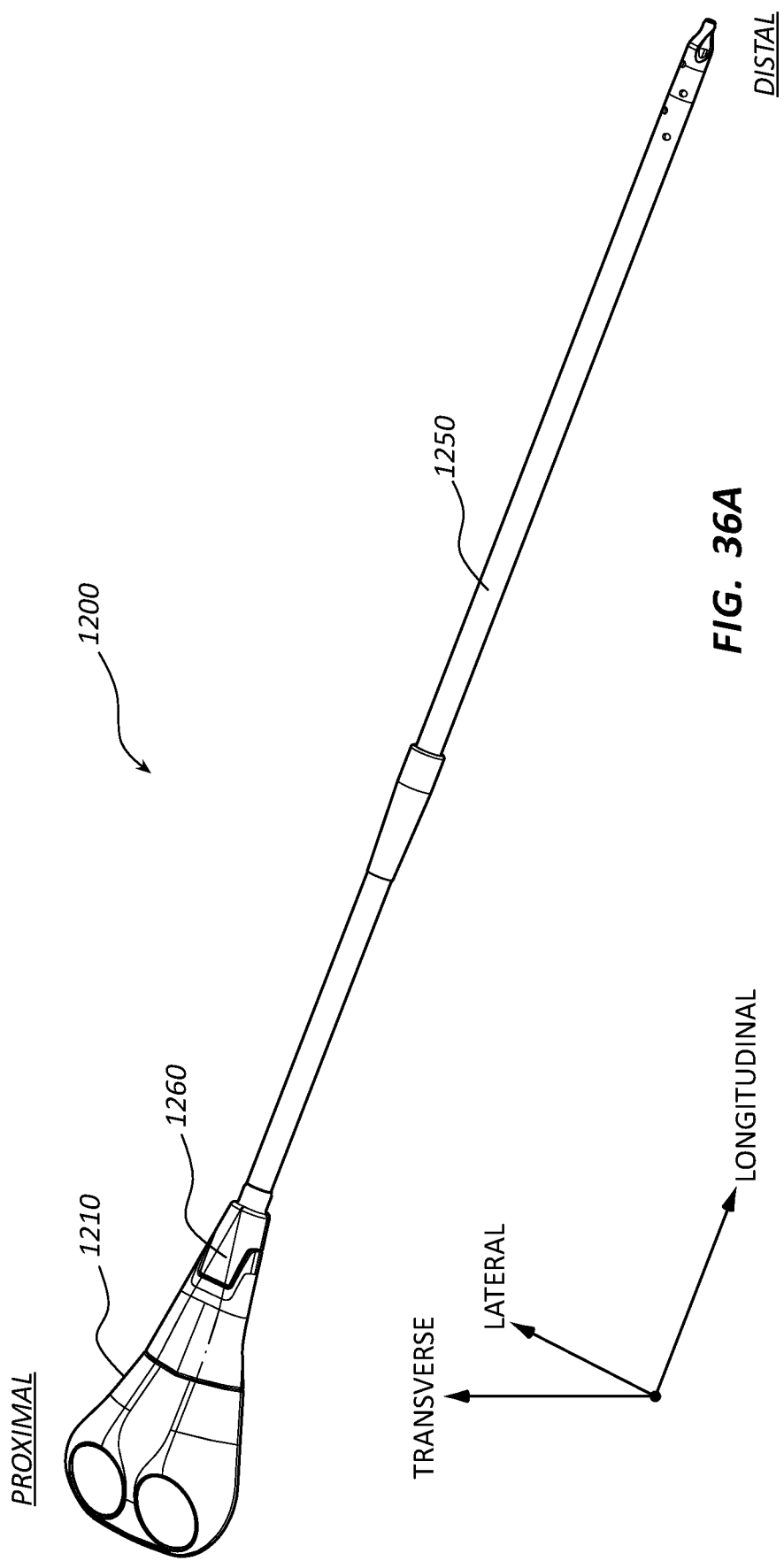
FIG. 36A depict a perspective view of a low-profile vascular access device according to one embodiment.
Figure 36B:
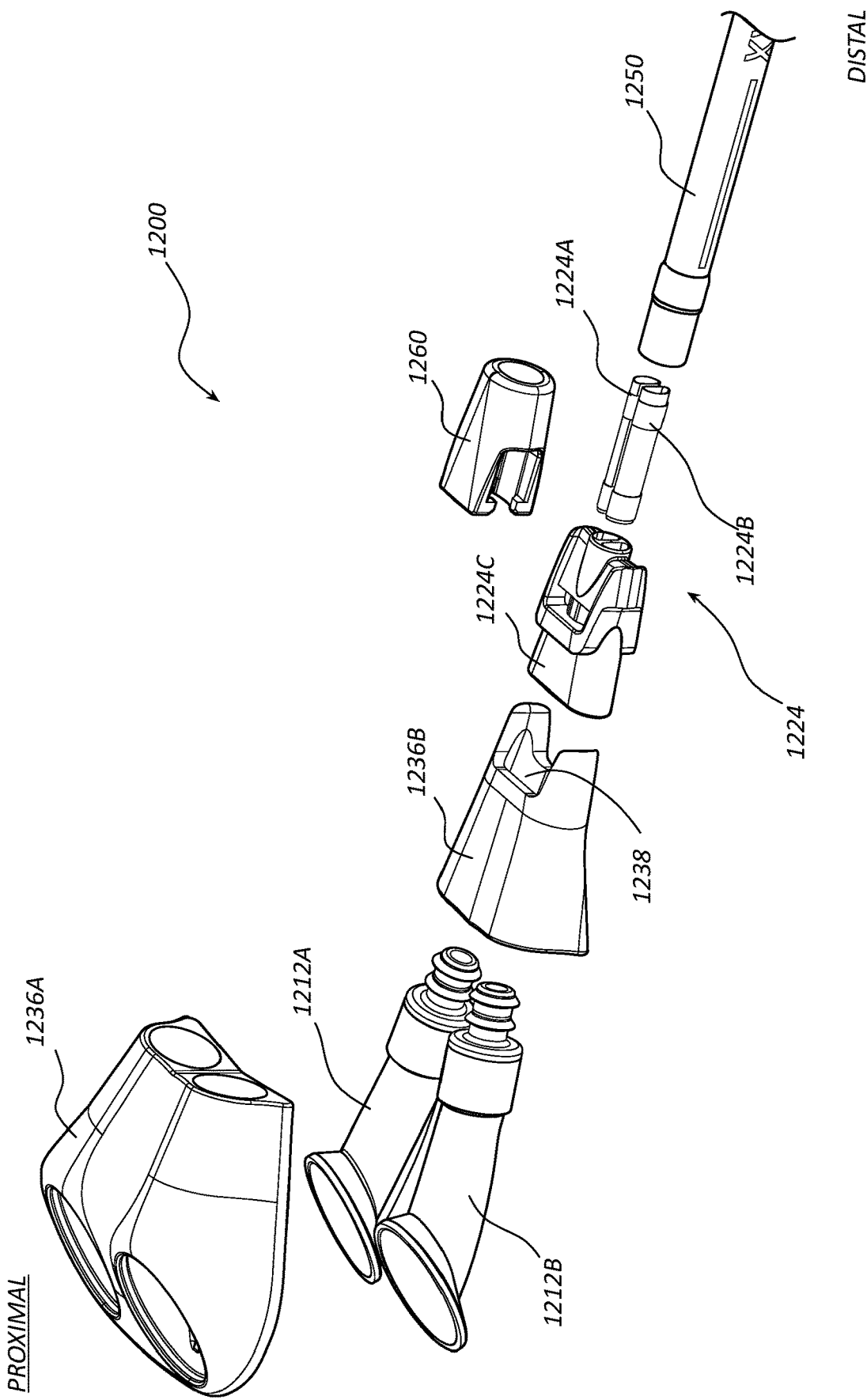
FIG. 36B depicts an exploded view of a low-profile vascular access device according to one embodiment.

Reference is now made to FIGS. 34A-34B, which show various details of a multi-lumen vascular access device, generally designated at 1010 in accordance with one embodiment. The port 1010 is configured to be surgically implanted under the skin of a patient, and includes a port body 1012 fluidly connected with an in-dwelling, multi-lumen catheter 1002 disposed within the vasculature of a patient. The port body 1012 comprises two elongate, compliant arms, 1014A, 1014B, each of which define a lumen 1020A, 1020B therein, which are fluidly connected with a lumen of the in-dwelling, multi-lumen catheter 1002, by way of a bifurcation hub 1016. The arms 1014, including the lumens 1020 disposed therein, extend proximally from a proximal end of the bifurcation hub 1016 along a longitudinal axis. Although FIGS. 34A-34B show two arms extending side by side along a longitudinal axis, other numbers of arms 1014 and configurations thereof are contemplated. For example, at least one arm 1014 can extend at an angle relative to the longitudinal axis. A proximal end of each of the arms 1014A, 1014B, terminates in an end cap 1018A, 1018B. The end cap 1018 can be formed of the same or of a different material from that of the arms and can be attached thereto using adhesive, welding, bonding, or similar suitable techniques. In an embodiment, the caps are formed monolithically with the arms 1014. The port 1010, or portions thereof, can be formed of any suitable biocompatible material, as discussed herein.

The port 1010, or portions thereof, can include palpation features 1026. For example, bifurcation hub 1016, end caps 1018, or combinations thereof can include palpation features that can indicate a position and/or orientation of the port body 1012, arms 1014, or the like, as discussed herein. Further, port 1010, portions thereof, or indicia included therewith, can include metals, such as titanium, that are radiopaque thus allowing the port 1010 to be located and identified using a suitable imaging modality, as discussed herein. For example, end cap 1018, arm 1014, bifurcation hub 1016, or combinations thereof, can include a radiopaque material to indicate a position and/or orientation of the port 1010, subsequent to subcutaneous implantation, using a suitable imaging modality, e.g. x-ray, CAT, PET, MRI, ultrasound, or the like. To note, the bifurcation hub 1016 and the end cap 1018 can include differently shaped palpation features 1026/radiopaque indicia to indicate to a user a flow direction. A needle 42 can then be inserted at an obtuse angle relative to the flow direction. It will be appreciated that the needle 42 can also be inserted substantially orthogonal to the longitudinal axis of the port 1010.

A portion of the arms 1014 can include a self-sealing, needle penetrable material, such as silicone, or the like. The self-sealing, needle penetrable material can be disposed in an upper wall 1022 of the arms 1014. Further, a lower wall 1024 of the arms can include a needle-impenetrable material, for example, plastic, metal, or the like. The upper and lower walls 1022, 1024 can be defined relative to the transverse axis. As noted the arms 1014 are compliant, this enables the arms to conform to the specific contours of the patient's body where it is subcutaneously implanted. Accordingly, while the material of the lower wall 1024 is needle impenetrable, the material is also sufficiently compliant to conform to the patient's body. In an embodiment, a portion of the inner surface of the lumen 1020 includes a needle impenetrable material, such as those discussed herein, that prevents the distal end of a needle from gouging the inner surface of the lumen when impinging thereon. This, in turn, prevents the undesirable creation of material flecks dug by the needle.

After locating the port 1010 via through-skin palpation or imaging, a clinician uses the catheter-bearing needle 42 to pierce a skin surface 44 and an upper wall of the port arm 1014, the latter including a needle-penetrable material. The needle 42 is inserted until a distal tip 42A thereof impinges on a lower wall 1024 of the arm 1014, which is formed of a needle-impenetrable material.

The needle 42 can then be proximally backed out a small distance, and the catheter 40 advanced over the needle such that the catheter bends and advances into the lumen 1020 of the arm 1014. Once the distal end 40A of the catheter 40 is in fluid communication with the arm lumen 1020, further advancement can cease and fluid transfer through the catheter 40 and port 1010 can commence, including infusion and/or aspiration through the stem 24. Once fluid transfer is completed, the catheter 40 can be withdrawn proximally and then withdrawn through the surface 44 of the skin and out of the patient.

Advantageously, the port 1010 provides a relatively large area with which a clinician can access the port while maintaining a low profile. This allows a clinician to access the dialysis device at different positions during the course of multiple dialysis treatments, by inserting the needle in different locations along the arms 1014.

Reference is now made to FIGS. 35A-35J, which show various details of a vascular access dialysis device, generally designated at 1110, in accordance with one embodiment.

The port 1110 is configured to be surgically implanted under the skin of a patient, and includes a port body 1112 fluidly connected at a distal end with an in-dwelling, multi-lumen catheter 1002 disposed within the vasculature of a patient. The port body 1112 defines an elongate chamber 1114, such as a first and second elongate chamber 1114A, 1114B. Each chamber is in fluid communication with a lumen of the in-dwelling catheter 1002 by way of conduit 1118, defined in port body 1112, which extends from chamber 1114 to a fluid outlet of stem 1124.

Each elongate chamber 1114 can extend longitudinally in a side by side arrangement. In an embodiment, as shown in FIG. 35F, each elongate chamber 1114 can be arranged in tandem such that one is more proximal than the other, as will be discussed in more detail herein. A lower surface of each chamber 1114 can be shaped as an elongate funnel shape so as to direct a needle impinging thereon towards an inlet 1116 of conduit 1118. In an embodiment, the chamber defines a substantially flat or even lower surface extending along the longitudinal axis. In an embodiment, the chamber defines a U-shaped cross sectional shape as shown in FIG. 35C.

Each chamber 1114 includes a septum 1140, formed of a self-sealing, needle-penetrating material, such as silicone. The port 1110 includes a needle guide 1142 disposed either above or below the septum 1140. The needle guide 1142 can be formed of a needle impenetrable material. In an embodiment, the needle guide 1142 can be formed either as a separate piece from that of port body 1112 or formed monolithically therewith. In an embodiment, the needle guide 1142 be formed as a separate piece from that of the septum 1140 and disposed either above or below the septum 1140. In an embodiment, the septum 1140 is overmolded onto the needle guide 1142 such that the needle guide is disposed within the septum 1140. In an embodiment, the needle guide 1142 includes a rail that longitudinally bisects the septum and laterally divide the septum into a plurality of distinct access areas, or openings.

The needle guide 1142 can guide the clinician to penetrate the septum at different positions, thereby avoiding repeated needle penetrations being concentrated at a single locus. The elongate wells 1114 and associated septa, provide a larger area with which to access the port while also maintaining a slim overall profile. The needle guide 1142 can guide a clinician to access the port at a different position, thus promoting tissue healing. For example, dialysis is performed every 2-3 days, the clinician can access the device at a first position 1144A proximate the proximal end of the needle guide 1142. During subsequent dialysis treatments, the clinician can use the needle guide 1142 to direct subsequent access points, or openings, at increasingly distal positions from the first 1144A, such as position 1144B. Accordingly, subsequent access points can migrate distally until the most distal position is reached 1144N. At which point the skin adjacent a first access point 1144A will have had a chance to heal and the clinician can re-access the initial access point 1144A. Further, the width of the wells 1114 and associated septa 1140 can allow some variation in needle access within a given position 1144 so that the septum is not traversed in exactly the same position each time, thus improving septum longevity.

In an embodiment, as shown in FIGS. 35D-I, each elongate chamber 1114 can be arranged in tandem such that a first chamber 1114A is more proximal than a second chamber 1114B. In such an example, the proximal most chamber 1114A can include a conduit 1118A, defined by the port body 1112, which extends past the more distal chamber 1114B and is fluidly connected with the stem 1124. FIG. 35F shows a first vertical cut away view of the port 1110 where a first chamber 1114A includes a first conduit 1118A extending through first side of the port 1110 and connecting with a first fluid outlet 1124A at the stem 1124. FIG. 35E shows a second vertical cut away view of the port 1110 where a second chamber 1114B includes a second conduit 1118B extending through second side of the port 1110 and connecting with a second fluid outlet 1124B at the stem 1124. In an exemplary embodiment, FIG. 35H shows a horizontal cutaway view of an internal chamber 1114/conduit 1118 routing. Advantageously, the tandem configuration allows for a wider septa 1140, providing more variation in injection sites at a given position. As such, a particular injection locus on a septum is not degraded from repeated needle penetrations, thereby promoting septa longevity.

It will be appreciated that the port body 1112 can be formed of a suitable biocompatible material, as discussed herein. The port body 1112 can be formed of a needle impenetrable material, optionally each chamber 1114 can include a needle impenetrable material lining an inner surface thereof, as discussed herein. As shown, port 1110 includes two wells 1114 formed in a port body 1112 as a single monolithic piece, although it will be appreciate that any number of wells can be formed in the port 1110 and fall within the scope of the present invention. In an embodiment, the port 1110 can include a single chamber 1114 formed in the port body 1110. In an embodiment, the port 1110 can include wells 1114 formed as separate structures that are each connect to a lumen of a multi-lumen catheter, or an extension leg of a bifurcated catheter. In an embodiment, each chamber can be designed with different characteristics for different purposes. For example, a first chamber can be designed for blood withdrawal and a second chamber for blood return, or they may be reversibly separable. As in other embodiments, one side may be used for blood withdrawal and the other side for blood return.

Reference is now made to FIG. 36A-37E, which shows details of an indwelling catheter assembly 1200, in accordance with one embodiment. The catheter assembly 1200 includes a port 1210 fluidly connected to a catheter 1250 by way of locking member 1260. FIG. 36B shows an exploded view of the catheter assembly 1200 including the port 1210, the locking member 1260 and a proximal end of the catheter 1250. The port 1210 includes a body 1212 that is defined by a similarly shaped first conduit 1212A and second conduit 1212B. A distal end of each of the first and second conduits 1212A, 1212B engages a distal portion 1236B of an outer shell 1236. The distal end of the outer shell 1236 includes a distal receiving slot 1238 which engages a proximal end of a stem assembly 1224. The stem assembly 1224 includes a housing 1224C which is configured to receive a first and second stem 1224A, B at a distal end thereof.

Each of the first and second conduits 1212A, B, outer shell portions 1236A, B, and stem assembly 1224, can be press fitted into engagement with each other. Further, the first and second conduits 1212A, 1212B, can include a metal, such as titanium. It will be appreciated that the port body 1212, or portions thereof, can include a variety of materials, including metals, thermoplastics, ceramics, etc., and can include other joining methods including snap-fitted, adhesive, ultrasonic or other welding, interference fit, etc. as discussed herein. In an embodiment, the port 1210 further includes a portion of the outer shell 1236 that is overmolded onto a portion of the port body 1212. For example, proximal portion 1236A of the outer shell 1236 is formed of a compliant material, such as silicone, or similar suitable material as discussed herein and is overmolded onto the port body 1212.

Figure 37A:
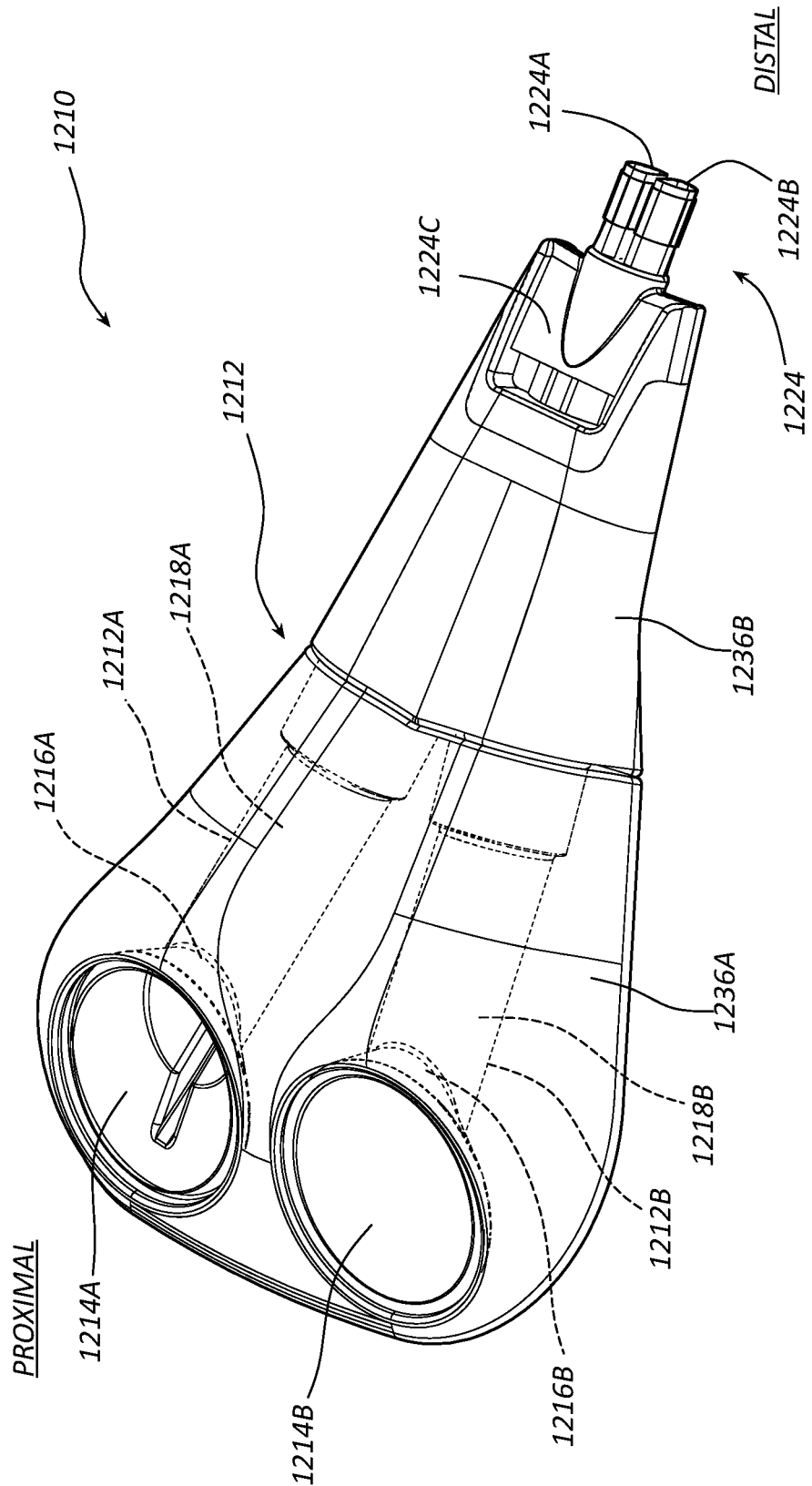
FIG. 37A depicts a perspective view of a port assembly of the device of FIG. 36A.
Figure 37B:
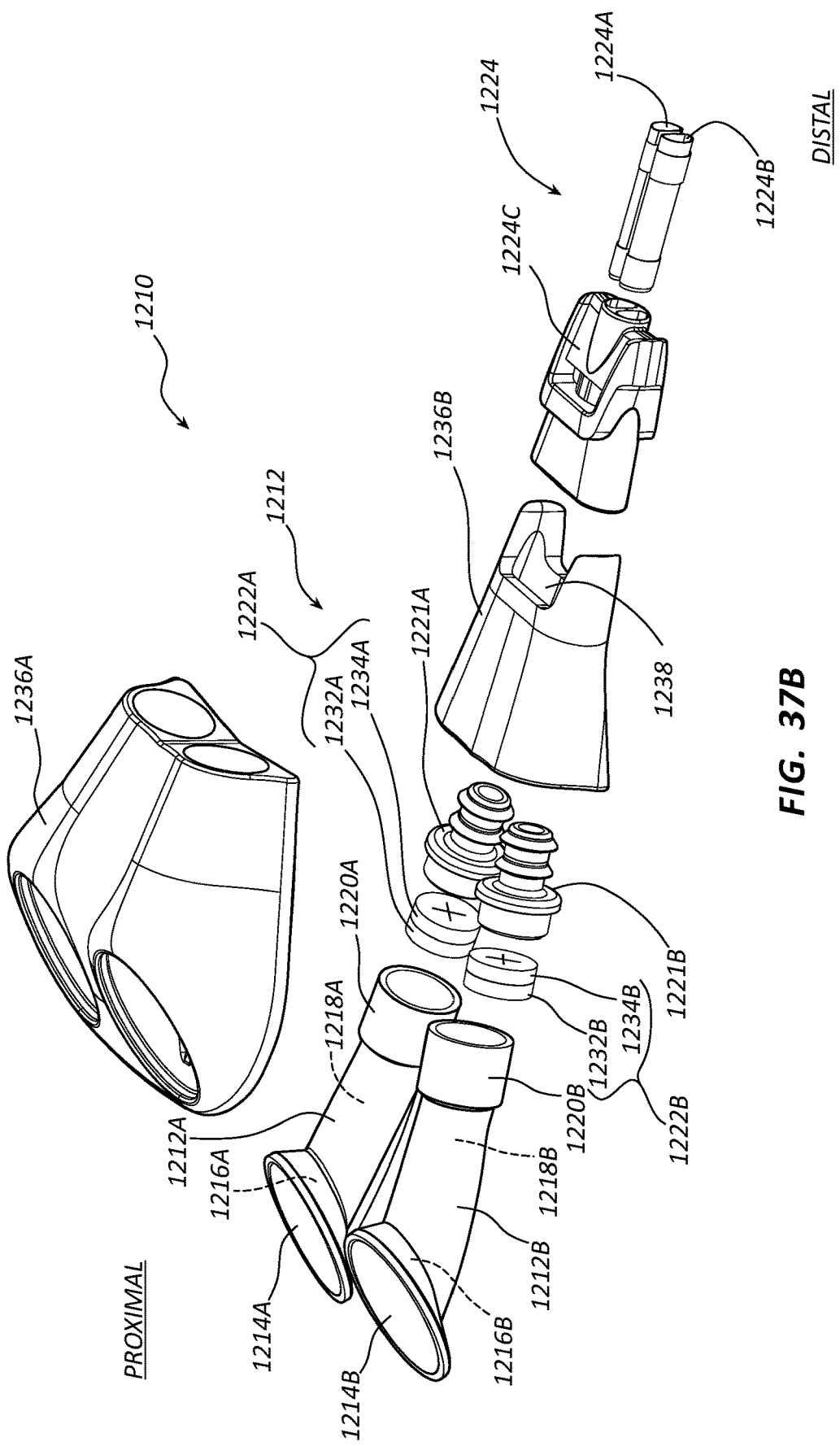
FIG. 37B depicts an exploded view of the port assembly of FIG. 37A.

FIGS. 37A-B show further details of the port 1210 of the catheter assembly 1200. Each of the first and second conduits 1212A, 1212B define a substantially funnel-shaped receiving cup 1214 for receiving and directing the catheter-bearing needle 42 (FIG. 14A) to operably connect with the port 1210 in a manner similar to that already described herein. In particular, the substantially funnel shape of each receiving cup 1214 is configured to direct the catheter-bearing needle 42 impinging thereon toward an inlet port 1216 that serves as an opening for a respective conduit 1212. The open and shallow nature of each receiving cup 1214, angled toward the skin surface of the patient enables the receiving cup to present a large, easily accessible target for the needle when introduced into the skin and directed toward the subcutaneously implanted access port 1210.

Each of the first and second conduits 1212A, 1212B further include a valve/seal assembly 1222, such as valve/seal assembly 1222A, 1222B. Each valve/seal assembly 1222 includes a seal 1232 and a valve 1234 disposed in a valve/seal housing 1220. Each valve seal housing 1220 is disposed at a distal end of the respective first and second conduits 1212A, 1212B and secured in place with a nozzle 1221, e.g. nozzle 1221A, B. A distal end of the nozzle 1221 is received within a proximal end of the outer shell distal portion 1236B. Accordingly, the port body 1212, including the respective valve/seal assemblies 1220, nozzles, 1221 and stem 1224 define lumen 1218A, 1218B that extend from an inlet port 1216A, 1216B to a respective outlet of stem 1224A, 1224B. Note that features of other embodiments described herein, for example palpation features, indicia, septa, guide grooves, valves, seals, etc., can be included with the port 1210.

FIG. 38A-38B shows details of an exemplary multi-lumen catheter 1250. The catheter 1250 includes an elongate tube extending from a proximal end to a distal end and can define at least one lumen. Although FIG. 38B shows a dual-lumen catheter it will be appreciated that catheters with greater or fewer lumens are contemplated to fall within the scope of the present invention. A proximal end 1252 is configured to fluidly communicate with stem assembly 1224. In an embodiment, a first stem 1224A communicates with a first lumen 1254A and a second stem 1224B communicates with a second lumen 1254B.

The catheter 1250 includes an annular collar 1256 disposed proximate a proximal end which co-operates with a locking member 1260, and will be discussed in more detail herein. The catheter 1250 also includes a cuff 1258. The cuff 1258 can be made of, for example DACRON™, or similar suitable material. The cuff 1258 serves as an ingrowth cuff to further secure the catheter upon implantation within the body.

Figure 39A:
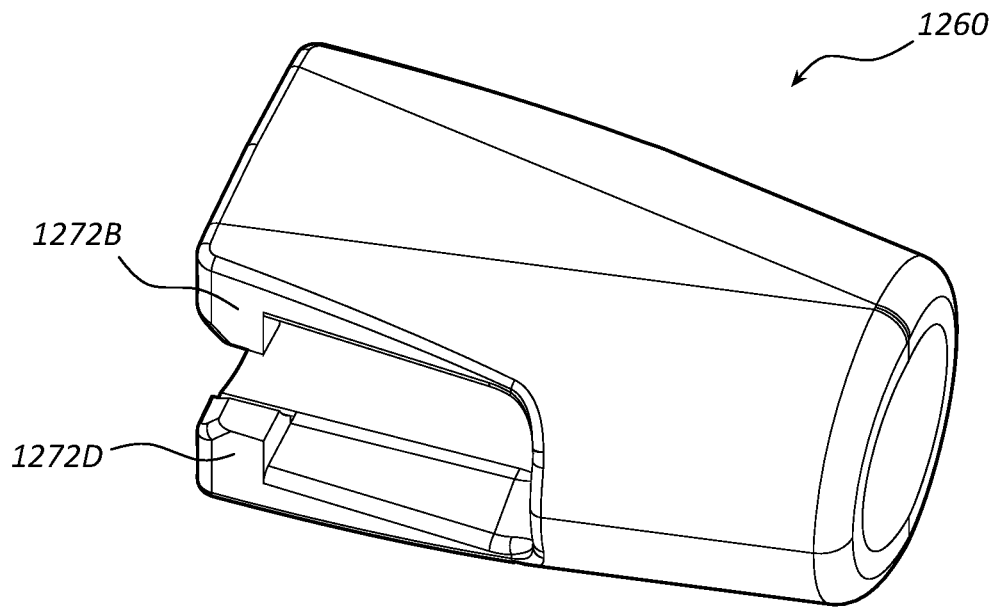
FIG. 39A-39C depict various views of the connector of the device of FIG. 36A.
Figure 39B:
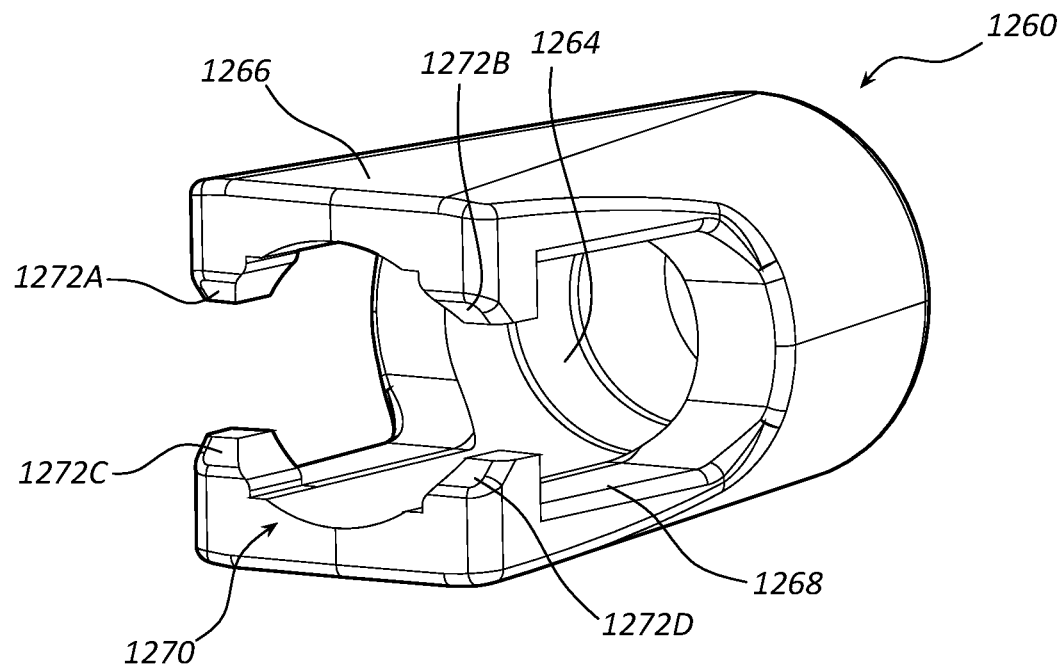
Figure 39C:
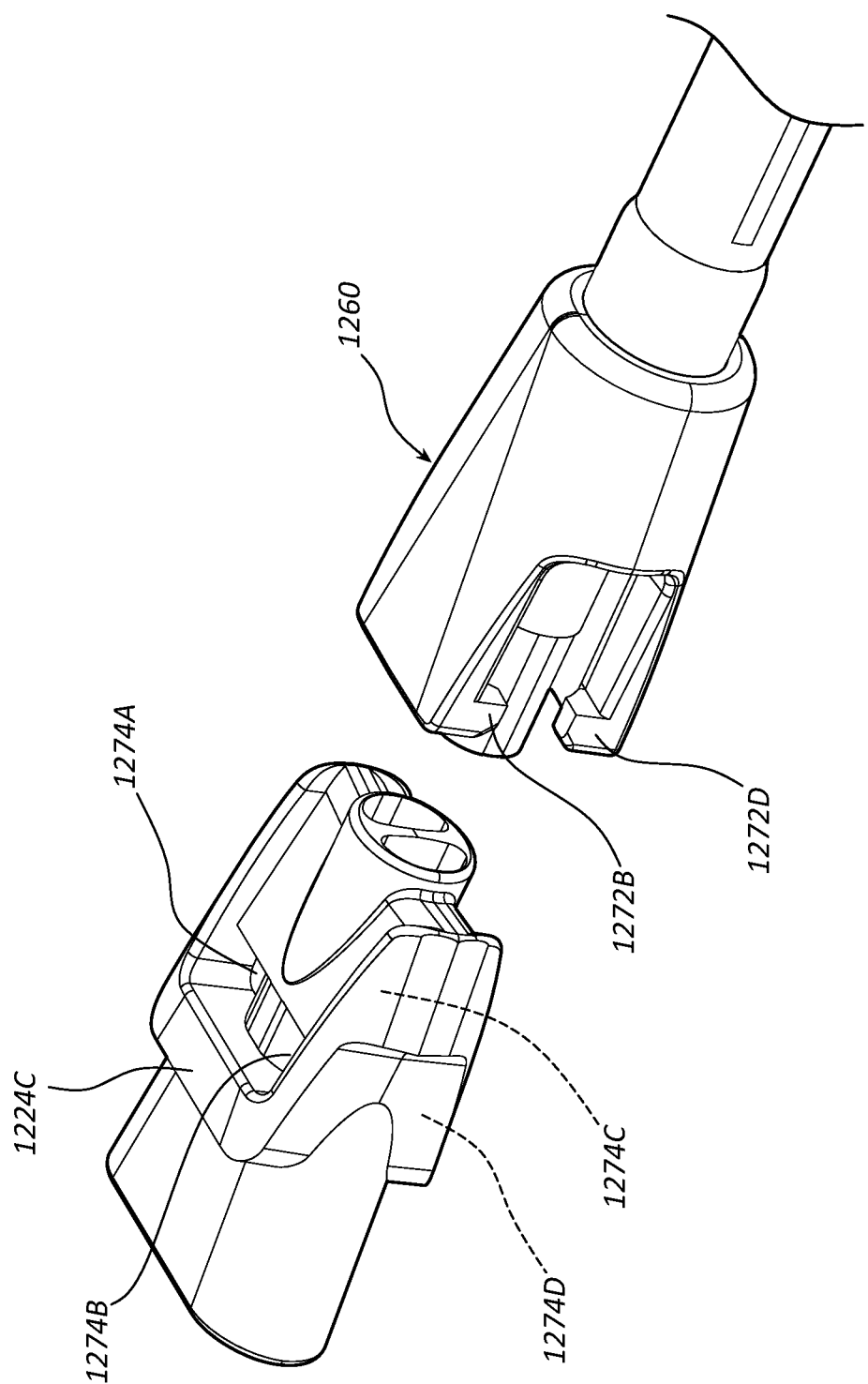

Referring to FIGS. 39A-39C, the catheter assembly 1200 further includes a locking member 1260 that fits over the catheter 1250 and engages the port body 1212, securing the catheter 1250 thereto. To note, FIG. 39C shows the stem assembly housing 1224C, locking member 1260 and catheter 1250, with the first and second stems 1224A, B removed for clarity. The locking member 1260 includes a channel 1262 extending from a proximal end to a distal end of the locking member 1260, and is designed to receive a catheter disposed therethrough. A circumference of the channel 1262 is sized to fit snugly about a circumference of the catheter 1250. The locking member 1260 includes an annular abutment 1264 disposed towards a distal end of the channel 1262 and extending radially inward. The annular abutment 1264 abuts against an annular collar 1256 of the catheter and inhibits longitudinal distal movement of the catheter relative to the locking member 1260.

The locking member 1260 includes an upper and lower portion 1266, 1268 that extend proximally to define an upper and lower surface of the locking member 1260, respectively. The upper and lower portions 1266, 1268 further define openings in the left and rights sides of the locking member 1260. The openings extend proximally, from a distal end, to a point that is proximal of the distal end and are configured to receive a portion of the stem assembly housing 1224C.

The locking member 1260 further includes protrusions 1272 disposed at a distal end of the locking member 1260 and extend transversely inwards. Protrusions 1272A, 1272B extend transversely downwards from a distal end of the upper portion 1266, and protrusions 1272C, 1272D extend transversely upwards from a distal end of the lower portion 1268. The protrusions 1272 co-operate with slots 1274 disposed in an upper and lower surface of the port housing 1224C, such that each protrusion 1272A-D engages a corresponding slot 1274A-D.

The locking member 1260 includes a resilient material such that an upper and lower portions 1266, 1268 are able to flex slightly. Accordingly, as the locking member 1260 is urged distally to engage the housing 1224C the upper and lower portions 1266, 1268 flex outward allowing the housing 1224C to be received within the space defined by the upper and lower portions 1266, 1268 of the connector. Further, the protrusions 1272 can include a chamfer to facilitate sliding over a distal portion of the housing 1224C and engage the slots 1274. Accordingly, the locking member can securely engage the housing 1224C and can align the catheter 1250 with the stem 1224.

Advantageously, the catheter assembly 1200 provides a modular construction where individual components can be press fitted or snap fitted into place, although other methods of attaching are also contemplated. Accordingly, this facilitates manufacture and assembly together with improved associated costs. Moreover, being formed of a modular construction allows individual components to be modified and changed to suit different specifications with minimal interference to the manufacturing process. For example, port body 1212 can be configured to receive different gauge needles, catheters, or the like by exchanging the body conduits 1212A, 1212B, nozzles, 1221, valve assemblies 1222, or the like. Similarly, the catheter 1250 and stem assemblies 1224 can be easily exchanged for catheters of different characteristics such as different gauges, thicknesses, physical characteristics (e.g. materials, durometers), lumens characteristics, tip characteristics, or the like.

The port 1210, locking member 1260 and catheter 1250 can also co-operate to define a substantially smooth outer profile to the catheter system 1200. This advantageously facilitates implantation within a tissue pocket and reduces patient discomfort once implanted. Further, a smooth outer profile allows any palpation features disposed there on to be more pronounced and therefore more easily discernable by a clinician.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A vascular access device for subcutaneous implantation, comprising:
    a catheter having a first lumen and a second lumen;
    an elongate body defining a first elongate chamber and a second elongate chamber, the first elongate chamber in fluid communication with the first lumen and the second elongate chamber in fluid communication with the second lumen;
    a needle penetrable septum disposed over an opening in an upper surface of the elongate body, the opening providing access to the first elongate chamber and the second elongate chamber; and
    a needle impenetrable guide disposed over the opening and the needle penetrable septum, the needle impenetrable guide including a plurality of first openings positioned over the first elongate chamber, and a plurality of second openings positioned over the second elongate chamber.

2. The vascular access device according to claim 1, wherein the elongate body has a length and a width, the length more than two times greater than the width.

3. The vascular access device according to claim 1, wherein the first elongate chamber and the second elongate chamber extend in a side-by-side arrangement relative to a longitudinal axis of the elongate body.

4. The vascular access device according to claim 1, wherein the first elongate chamber and the second elongate chamber are in a tandem arrangement relative to a longitudinal axis of the elongate body such that the first elongate chamber is proximal to the second elongate chamber.

5. The vascular access device according to claim 1, wherein the needle impenetrable guide is disposed at least partially within the needle penetrable septum.

6. The vascular access device according to claim 1, wherein the needle impenetrable guide does not penetrate the needle penetrable septum.

7. The vascular access device according to claim 1, wherein the plurality of first openings are parallel to the plurality of second openings.

\* \* \* \* \*